United States Patent
Seeley et al.

(10) Patent No.: US 8,530,404 B2
(45) Date of Patent: Sep. 10, 2013

(54) COMPOUNDS AND METHODS FOR TREATMENT OF CANCER

(75) Inventors: Todd W. Seeley, Moraga, CA (US); David Y. Liu, Palo Alto, CA (US); Stephen J. Klaus, San Francisco, CA (US)

(73) Assignee: FibroGen, Inc., San Francisco, CA (US)

( * ) Notice: Subject to any disclaimer, the term of this patent is extended or adjusted under 35 U.S.C. 154(b) by 192 days.

(21) Appl. No.: 11/455,199

(22) Filed: Jun. 15, 2006

(65) Prior Publication Data

US 2007/0004627 A1   Jan. 4, 2007

Related U.S. Application Data

(60) Provisional application No. 60/691,006, filed on Jun. 15, 2005.

(51) Int. Cl.
*A01N 61/00* (2006.01)

(52) U.S. Cl.
USPC .............................................. 514/1; 435/7.23

(58) Field of Classification Search
None
See application file for complete search history.

(56) References Cited

U.S. PATENT DOCUMENTS

| | | | |
|---|---|---|---|
| 5,942,434 A | 8/1999 | Ratcliffe et al. | |
| 6,124,131 A | 9/2000 | Semenza | |
| 6,432,927 B1 | 8/2002 | Gregory et al. | |
| 6,562,799 B1 | 5/2003 | Semenza | |
| 2003/0153503 A1* | 8/2003 | Klaus et al. | 514/12 |
| 2003/0176317 A1* | 9/2003 | Guenzler-Pukall et al. | 514/1 |

FOREIGN PATENT DOCUMENTS

| | | |
|---|---|---|
| WO | WO-00/69908 A1 | 11/2000 |
| WO | WO-02/074249 A3 | 9/2002 |
| WO | WO-02/074981 A2 | 9/2002 |
| WO | WO-03/045440 A1 | 6/2003 |
| WO | WO-03/049686 A3 | 6/2003 |
| WO | WO-03/053997 A2 | 7/2003 |
| WO | WO-03/100438 A1 | 12/2003 |
| WO | WO-2004/108121 A1 | 12/2004 |
| WO | WO-2004/108681 A1 | 12/2004 |
| WO | WO-2005/007192 A2 | 1/2005 |
| WO | WO-2006/010920 A1 | 2/2006 |

OTHER PUBLICATIONS

Eres et al, Cancer research, 2003, 63:8777-8783.*
Ben-Efraim, Tumor Biology 1999; 20: 1-24.*
Marincola et al, Trends in Immunology 2003; 24: 334-341.*
Frazer, I., Expert. Opin. Pharmacother. 2004; 5: 2427-2434.*
Volm et al, Anitcancer Res, 2000, 20:1527-1534.*
Koivunen et al, J Biol Chem, 2004, 279:9899-9904.*
Acker, Till, et al., "Genetic Evidence for a Tumor Suppressor Role of HIf-2a," Cancer Cell, vol. 8, Aug. 2005, pp. 131-141.
Belozerov, Vladimir E., et al., "Hypoxia Inducible Factor-1: A Novel Target for Cancer Therapy," Anti-Cancer Drugs, vol. 16, 2005, pp. 901-909.
Box, Adrian H., et al., "Cell Cycle Kinase Inhibitor Expression and Hypoxia-Induced Cell Cycle Arrest in Human Cancer Cell Lines," Carcinogenesis, vol. 25, No. 12, 2004, pp. 2325-2335.
Brugarolas, James, et al., "Regulation of mTOR Function in Response to Hypoxia by REDD1 and the TSC1/TSC2 Tumor Suppressor Complex," Genes Dev, vol. 18, 2004, pp. 2893-2904.
Carmeliet, Peter, et al., "Role of HIF-1a in Hypoxia-Mediated Apoptosis, Cell Proliferation and Tumour Angiogenesis," Nature, vol. 394, Jul. 1998, pp. 485-490.
Goda, Nobuhito, et al., "HIF-1 in Cell Cycle Regulation, Apoptosis and Tumor Progression," Antioxid Redox Signal, vol. 5, No. 4, 2003, pp. 467-473.
Mack, Fiona A., et al., "Decreased Growth of Vhl -/- Fibrosarcomas is Associated With Elevated Levels of Cyclin Kinase Inhibitors p21 and p27," Mol Cell Biol, vol. 25, No. 11, Jun. 2005, pp. 4565-4578.
Powis, Garth, et al., "Hypoxia Inducible Factor-1a as a Cancer Drug Target," Mol Cancer Ther, vol. 3, No. 5, 2004, pp. 647-654.
Savai, Rajkumar, et al., "HIF-1a Attenuates Tumor Growth in Spite of Augmented Vascularization in an A549 Adenocarcinoma Mouse Model," Int J Oncol, vol. 27, 2005, pp. 393-400.
Semenza, Gregg, "Involvement of Hypoxia-Inducible Factor 1 in Human Cancer," Internal Medicine, vol. 41, No. 2, Feb. 2002, pp. 79-83.
Wang, Yang, et al., "A Novel Cancer Therapy: Combined Liposomal Hypoxia Inducible Factor 1 Alpha Antisense Oligonucleotides and an Anticancer Drug," Biochemical Pharmacology, vol. 68, 2004, pp. 2031-2042.

* cited by examiner

*Primary Examiner* — Mark Halvorson
(74) *Attorney, Agent, or Firm* — Leanne C. Price, Esq.

(57) ABSTRACT

The invention relates to methods and compounds for treating or preventing cancer. Methods for treating or preventing cancer, for inhibiting tumor growth, reducing tumor volume, inhibiting tumor progression, inhibiting metastasis, and improving survival are provided herein.

12 Claims, 1 Drawing Sheet

COMPOUNDS AND METHODS FOR TREATMENT OF CANCER

This application claims the benefit of U.S. Provisional Application Ser. No. 60/691,006, filed on 15 Jun. 2005, which is incorporated by reference herein in its entirety.

FIELD OF THE INVENTION

The invention relates to methods and compounds for treating or preventing cancer. Methods for treating or preventing cancer, for inhibiting tumor growth, reducing tumor volume, inhibiting tumor progression, inhibiting metastasis, and improving survival are provided herein.

BACKGROUND OF THE INVENTION

Cancers are characterized by abnormal and uncontrolled cell growth. Cancer can involve any tissue in the body, and can spread outside the tissue of origin. Uncontrolled proliferation and other cellular abnormalities can lead to the formation of cancerous tumors. Tumors can disrupt the function of and destroy the tissues in which they originate, and, when cancer cells metastasize, secondary tumors can develop near to or disparate from the site of primary growth.

Available anti-cancer therapies include the administration of various chemotherapeutic agents, exposure to radiation, surgery, and immunotherapy, any of which can lead to debilitating and even life-threatening adverse effects. Therefore, there is a need in the art for additional therapeutic approaches for the treatment of cancer, and the prevention of its growth and progression. The present invention meets these needs by providing methods for treating or preventing cancer, for inhibiting tumor growth, reducing tumor volume, inhibiting tumor progression, inhibiting metastasis, and improving survival.

SUMMARY OF THE INVENTION

The present invention relates to the discovery that, contrary to the teachings in the art, methods and compounds relating to stabilization of HIFα are therapeutically effective in treating or preventing cancer and in inducing a number of anti-tumor effects.

Therefore, in one aspect, the present invention provides a method for treating or preventing cancer in a subject in need, the method comprising administering to the subject an effective amount of an agent that stabilizes HIFα. The invention further provides a method for treating or preventing cancer in a subject in need, the method comprising administering to the subject an effective amount of an agent that inhibits HIF hydroxylase activity.

Methods for inducing anti-tumor effects in a subject in need are also contemplated herein. In one aspect, the invention provides a method for inducing an anti-tumor effect in a subject in need, the method comprising administering to the subject an effective amount of an agent that stabilizes HIFα. In another aspect, the invention encompasses a method for inducing an anti-tumor effect in a subject in need, the method comprising administering to the subject an effective amount of an agent that inhibits HIF hydroxylase activity.

While medical applications with humans are clearly foreseen, veterinary applications are also encompassed herein. Therefore, in a preferred embodiment, the subject is a mammalian subject, and in a most preferred embodiment, the subject is a human subject.

In various embodiments, an agent for use in the present methods is selected from the group consisting of a 2-oxoglutarate mimetic, an iron chelator, and a proline analog. In certain embodiments, the agent used in the present methods is a compound selected from the group consisting of the compounds of Formula I, Formula II, Formula III, and Formula IV. Formula I includes, but is not limited to, compounds of Formulae Ia, Ib, Ic, Id, and Ie; compounds of Formula Ie include, but are not limited to, compounds of Formulae Ie(i), Ie(ii), Ie(iii), and Ie(iv). Formula III includes but is not limited to, the compounds of Formula IIIa.

In particular embodiments, an agent of the present invention is selected from the group consisting of a pyridine-2-carboxamide, a quinoline-2-carboxamide, an isoquinoline-3-carboxamide, a cinnoline-3-carboxamide, a beta-carboline-3-carboxamide, a 4-oxo-[1,10]-phenanthroline, and an arylsulfono-amino-hydroxamate.

In particular embodiments, an agent for use in the present methods is selected from the group consisting of: Compound A [(1 Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid.

Methods of inducing an anti-tumor effect are provided herein. In various aspects, the anti-tumor effect is selected from the group consisting of: reducing tumor volume in the subject; inhibiting tumor growth in the subject; inhibiting tumor progression in the subject; altering the metabolic activity of a tumor in the subject; inducing quiescence of a tumor in the subject; inhibiting or reducing metastasis in the subject; inhibiting or reducing tumor invasiveness in the subject; inhibiting or reducing tumor angiogenesis and tumor neovascularization in the subject; reducing tumor weight in the subject; and improving survival of the subject.

In some embodiments, the methods of the present invention further comprise administering to the subject one or more chemotherapeutics or chemotherapeutic agents. The administration of the one or more chemotherapeutics in combination with one or more compounds of the present may be simultaneous, separate, or sequential administration, and administration may be in any order. Chemotherapeutic agents suitable for use in the methods of the present invention include, for example, alkylating agents; nitrosoureas; antimetabolites; anthracyclines and related drugs; topoisomerase II inhibitors; mitotic inhibitors, corticosteroid hormones, microtubule poisons, and DNA alkylating agents, including, but not limited to: busulfan, cisplatin, carboplatin, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, the vinca alkaloids (vinblastine, vincristine and vinorelbine), corticosteroid hormones include prednisone and dexamethasone. Use of chemotherapeutic agents including L-asparaginase, dactinomycin, thalidomide, tretinoin, imatinib (Gleevec), gefitinib (Iressa), erlotinib (Tarceva), rituximab (Rituxan), bevacizumab (Avastin), anti-estrogens (tamoxifen, fulvestrant), aromatase inhibitors (anastrozole, exemestane, letrozole), progestins (megestrol acetate), anti-androgens (bicalutamide, flutamide) and LHRH agonists (leuprolide, goserelin) is also contemplated herein.

Pharmaceutical compositions or medicaments effective for treating or preventing cancer, or for inducing anti-tumor effects, are also provided herein. In various embodiments, the compositions comprise an effective amount of an agent that stabilizes HIFα and a carrier. In other embodiments, the invention provides compositions comprising an effective amount of an agent that inhibits HIF hydroxylase activity and a carrier.

In various embodiments of the present methods, the agent is administered orally, systemically, by injection, and intravenously.

DESCRIPTION OF THE INVENTION

Figure 1:
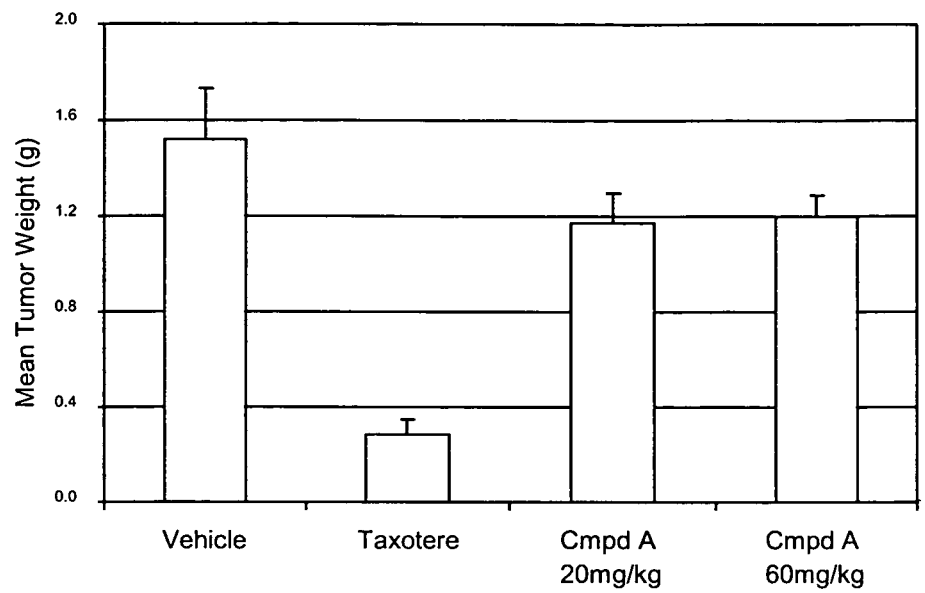
FIG. 1 sets forth data showing compounds and methods of the present invention reduced tumor weight in an animal xenograft model of orthotopically-implanted human breast tumors.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington's Pharmaceutical Sciences*, 18$^{th}$ ed., Mack Publishing Co.; Hardman, J. G., Limbird, L. E., and Gilman, A. G., eds. (2001) *The Pharmacological Basis of Therapeutics*, 10$^{th}$ ed., McGraw-Hill Co.; Colowick, S. et al., eds., *Methods In Enzgmology*, Academic Press, Inc.; Weir, D. M., and Blackwell, C. C., eds. (1986) *Handbook of Experimental Immunology*, Vols. I-IV, Blackwell Scientific Publications; Maniatis, T. et al., eds. (1989) *Molecular Cloning: A Laboratory Manual*, 2$^{nd}$ edition, Vols. I-III, Cold Spring Harbor Laboratory Press; Ausubel, F. M. et al., eds. (1999) *Short Protocols in Molecular Biology*, 4$^{th}$ edition, John Wiley & Sons; Ream et al., eds. (1998) *Molecular Biology Techniques: An Intensive Laboratory Course*, Academic Press; Newton, C. R., and Graham, A., eds. (1997) *PCR* (Introduction to Biotechniques Series), 2$^{nd}$ ed., Springer Verlag.

Invention

The present invention relates to the discovery by the present inventors that stabilization of HIFα is an effective anti-cancer therapy, leading to inhibition of tumor growth, reduced tumor volume, inhibition of tumor progression, reduced incidence or frequency of metastasis, and improved survival. This is contrary to the established art, which teaches that HIF stabilization leads to promotion of pro-angiogenic factors and would not be an effective anti-cancer therapy. (See, e.g., Powis and Kirkpatrick (2004) Mol Cancer Ther 3:647-654; Semenza (2002) Internal Medicine 41:79-83; and Belozerov and Van Meir (2005) Anti-Cancer Drugs 16:901-909.)

The invention relates to the identification of a group of compounds that have anti-tumor effects and can be administered to reduce tumor volume, inhibit tumor growth and progression, alter tumor metabolic activity, induce tumor quiescence, inhibit or reduce metastasis, inhibit or reduce tumor invasiveness, inhibit or reduce tumor angiogenesis and neovascularization, increase survival, and treat or prevent cancer in a subject in need. The invention further relates to the discovery that stabilization of the alpha subunit of hypoxia inducible factor (HIFα) provides anti-cancer effects, and that HIFα can be stabilized in a subject to reduce tumor volume, inhibit tumor progression and growth, alter tumor metabolic activity, induce tumor quiescence, inhibit or reduce metastasis, inhibit or reduce tumor invasiveness, and treat or prevent cancer.

Compounds of the invention having anti-tumor effects include agents selected from the group consisting of 2-oxoglutarate mimetics, iron chelators, and proline analogs. Exemplary compounds of the invention include Compound A (1-Chloro-4-hydroxy-isoquinoline-3-carbonyl)-amino]-acetic acid; Compound B (S)-2-[(4-Hydroxy-7-phenoxy-6,7-dihydro-isoquinoline-3-carbonyl)-amino]-propionic acid; Compound C {[4-Hydroxy-7-(4-methoxy-phenoxy)-isoquinoline-3-carbonyl]-amino}-acetic acid; Compound D [(4-Hydroxy-1-methyl-7-phenoxy-isoquinoline-3-carbonyl)-amino]-acetic acid, and Compound E [7-(4-Fluoro-phenoxy)-4-hydroxy-isoquinoline-3-carbonyl]-amino-acetic acid. Further exemplary compounds of the invention include Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-iso-quinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid.

In particular, it is demonstrated herein that HIF prolyl hydroxylase inhibitors effectively reduced tumor progression, reduced tumor growth, and reduced mean tumor volume in established xenograft models of human cancer. Xenograft models of human cancer are considered useful in predicting the clinical efficacy of cancer drugs. Human tumor xenografts implanted subcutaneously (s.c.) into immunosuppressed mice have played a significant role in preclinical anticancer drug development, and constitute a predictive indicator of clinical activity. Key considerations in the establishment of xenograft models include site of implantation, growth properties of the xenograft and size when treatment is initiated, agent formulation, scheduling, route of administration and dose, and the selected endpoint for assessing activity. In these models, a slowing of xenograft tumor growth (cytostatic effect) or of tumor shrinkage might be the major observed effect.

In recent years, orthotopic routes for xenografted tumor implantation have been developed to display properties improving the clinical relevance of these models. Xenografted tumors implanted into an anatomical site matching the tissue of origin (orthotopic implantation) will often metastasize in a similar manner and to similar locations as the same tumor type in human cancers. For these reasons, orthotopic implantation may constitute an improved predictive indicator of clinical activity, particularly with respect to treatments that affect metastasis.

The present invention provides methods and compounds useful for treatment and prevention of cancer in a subject. In various embodiments, the subject can be a cell, tissue, organ, organ system, or whole organism. In preferred embodiments, the subject is a human subject. It is specifically contemplated in certain embodiments that the subject is a subject having or at risk for developing a malignancy, a cancer, a tumor, or any neoplastic disease or disorder.

In one aspect, the invention provides a method for reducing tumor volume in a subject, the method comprising stabilizing HIFα in the subject. Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. In further aspects, HIFα is HIF1α, HIF2α, or HIF3α. In a preferred aspect, stabilizing HIFα comprises administering to the subject an effective amount of a compound that inhibits HIF hydroxylase activity.

In some aspects, the present invention contemplates that stabilizing HIFα comprises administering an agent that stabilizes HIFα. The agent can be composed of polynucleotides, e.g. antisense sequences; polypeptides; antibodies; other proteins; carbohydrates; fats; lipids; and organic and inorganic substances, e.g., small molecules, etc. In a preferred aspect, the present invention contemplates stabilizing HIFα, e.g., in a subject, by administering to the subject an agent that stabilizes HIFα wherein the agent is a compound, e.g., small molecule compound, etc., that stabilizes HIFα. In certain aspects, the agent is selected from the group consisting of 2-oxoglutarate mimetics, iron chelators, and proline analogs. In particular embodiments, the agent is selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

In another embodiment, the invention provides a method for reducing tumor volume in a subject, the method comprising inhibiting HIF hydroxylase activity in the subject. In certain embodiments, the HIF hydroxylase is selected from the group consisting of EGLN1, EGLN2, and EGLN3. In a preferred embodiment, the invention provides a method for reducing tumor volume, the method comprising inhibiting HIF prolyl hydroxylase activity in a subject. Inhibition of HIF prolyl hydroxylase can be accomplished by any of the methods available to and known by those of skill in the art. The inhibition can be direct or indirect, can be competitive or non-competitive, etc. In various embodiments, the invention provides a method for reducing tumor volume in a subject, the method comprising administering to the subject an agent that inhibits HIF prolyl hydroxylase. In one embodiment, the agent is selected from the group consisting of 2-oxoglutarate mimetics, iron chelators, and proline analogs. In another embodiment, the agent is selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

In one embodiment, the invention provides a method for inhibiting tumor growth in a subject, the method comprising stabilizing HIFα in the subject. In a further embodiment, the method for inhibiting tumor growth in a subject comprises administering to the subject an agent that stabilizes HIFα. In another embodiment, the invention provides a method for inhibiting tumor growth in a subject, the method comprising inhibiting HIF hydroxylase activity in the subject. In a preferred embodiment, the invention provides a method for inhibiting tumor growth in a subject, the method comprising inhibiting HIF prolyl hydroxylase activity in the subject. In another embodiment, the invention provides a method for inhibiting tumor growth in a subject by administering to the subject an agent selected from the group consisting of 2-oxoglutarate mimetics, iron chelators, and proline analogs. In another embodiment, methods are provided for inhibiting tumor growth in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

In one embodiment, the invention provides a method for inhibiting tumor progression in a subject, the method comprising stabilizing HIFα in the subject. In another embodiment, the method for inhibiting tumor progression in a subject comprises administering to the subject an agent that stabilizes HIFα. In another embodiment, the invention provides a method for inhibiting tumor progression in a subject, the method comprising inhibiting HIF hydroxylase activity in the subject. In a preferred embodiment, the invention provides a method for inhibiting tumor progression in a subject, the method comprising inhibiting HIF prolyl hydroxylase activity in the subject. In another embodiment, the invention provides a method for inhibiting tumor progression in a subject by administering to the subject an agent selected from the group consisting of 2-oxoglutarate mimetics, iron chelators, and proline analogs. In another embodiment, methods are provided for inhibiting tumor progression in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

In one embodiment, the invention provides a method for altering the metabolic activity of a tumor in a subject, the method comprising stabilizing HIFα in the subject. In one aspect, the method for altering the metabolic activity of a tumor in a subject comprises administering to the subject an agent that stabilizes HIFα. In another embodiment, the invention provides a method for altering the metabolic activity of a tumor in a subject, the method comprising inhibiting HIF hydroxylase activity in the subject. In a preferred embodiment, the invention provides a method for altering the metabolic activity of a tumor in a subject, the method comprising inhibiting HIF prolyl hydroxylase activity in the subject. In another embodiment, the invention provides a method for altering the metabolic activity of a tumor in a subject by administering to the subject an agent selected from the group consisting of 2-oxoglutarate mimetics, iron chelators, and proline analogs. In another embodiment, methods are provided for altering the metabolic activity of a tumor in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

In one embodiment, the invention provides a method for inducing quiescence of a tumor in a subject, the method comprising stabilizing HIFα in the subject. In another embodiment, the method for inducing quiescence of a tumor in a subject comprises administering to the subject an agent that stabilizes HIFα. In another embodiment, the invention provides a method for inducing quiescence of a tumor in a subject, the method comprising inhibiting HIF hydroxylase activity in the subject. In a preferred embodiment, the invention provides a method for inducing quiescence of a tumor in a subject, the method comprising inhibiting HIF prolyl hydroxylase activity in the subject. In another embodiment, the invention provides a method for inducing quiescence of a tumor in a subject by administering to the subject an agent selected from the group consisting of 2-oxoglutarate mimetics, iron chelators, and proline analogs. In another embodiment, methods are provided for inducing quiescence of a tumor in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

In one embodiment, the invention provides a method for inhibiting or reducing metastasis in a subject, the method comprising stabilizing HIFα in the subject. In another embodiment, the method for inhibiting or reducing metastasis in a subject comprises administering to the subject an agent that stabilizes HIFα. In another embodiment, the invention provides a method for inhibiting or reducing metastasis in a subject, the method comprising inhibiting HIF hydroxylase activity in the subject. In a preferred embodiment, the invention provides a method for inhibiting or reducing metastasis in a subject, the method comprising inhibiting HIF prolyl hydroxylase activity in the subject. In another embodiment, the invention provides a method for inhibiting or reducing metastasis in a subject by administering to the subject an agent selected from the group consisting of 2-oxoglutarate mimetics, iron chelators, and proline analogs. In another embodiment, methods are provided for inhibiting or reducing metastasis in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

In one embodiment, the invention provides a method for inhibiting or reducing tumor invasiveness in a subject, the method comprising stabilizing HIFα in the subject. In a further embodiment, the method for inhibiting or reducing tumor invasiveness in a subject comprises administering to the subject an agent that stabilizes HIFα. In another embodiment, the invention provides a method for inhibiting or reducing tumor invasiveness in a subject, the method comprising inhibiting HIF hydroxylase activity in the subject. In a preferred embodiment, the invention provides a method for inhibiting or reducing tumor invasiveness in a subject, the method comprising inhibiting HIF prolyl hydroxylase activity in the subject. In another embodiment, the invention provides a method for inhibiting or reducing tumor invasiveness in a subject by administering to the subject an agent selected from the group consisting of 2-oxoglutarate mimetics, iron chelators, and proline analogs. In another embodiment, methods are provided for inhibiting or reducing tumor invasiveness in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

Metastases are predominantly angiogenesis-dependent. Experimental animal models of tumor growth and metastasis have indicated that metastases are essentially nonexistent before tumors have become neovascularized. Various environmental and physiological conditions and factors are associated with tumor neovascularization, metastases, and invasion. Such conditions and factors include, for example, inflammation and various inflammatory cytokines.

Methods and compounds of the present invention overcome tumor angiogenesis and neovascularization associated with inflammation and inflammatory cytokines. In one aspect, the present invention demonstrates that HIFα stabilization overcomes tumor angiogenesis and neovascularization associated with inflammation and inflammatory cytokines. In another aspect, the present invention demonstrates that HIF prolyl hydroxylase inhibitors overcome tumor angiogenesis and neovascularization associated with inflammation and inflammatory cytokines.

In one embodiment, the invention provides a method for inhibiting or reducing tumor angiogenesis and tumor neovascularization in a subject, the method comprising stabilizing HIFα in the subject. In another embodiment, the method for inhibiting or reducing tumor angiogenesis and tumor neovascularization in a subject comprises administering to the subject an agent that stabilizes HIFα. In another embodiment, the invention provides a method for inhibiting or reducing tumor angiogenesis and tumor neovascularization in a subject, the method comprising inhibiting HIF hydroxylase activity in the subject. In a preferred embodiment, the invention provides a method for inhibiting or reducing tumor angiogenesis and tumor neovascularization in a subject, the method comprising inhibiting HIF prolyl hydroxylase activity in the subject. In another embodiment, the invention provides a method for inhibiting or reducing tumor angiogenesis and tumor neovascularization in a subject by administering to the subject an agent selected from the group consisting of 2-oxoglutarate mimetics, iron chelators, and proline analogs. In another embodiment, methods are provided for inhibiting or reducing tumor angiogenesis and tumor neovascularization in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

Cancers

The following are non-limiting examples of the cancers and tumor types treatable using the present methods and compounds.

In the methods of the present invention, the cancer may in particular be cancer of the lung, colon, or breast. However, other cancers are also envisaged in the methods of the present invention. For example, the cancer may be ovarian cancer, including advanced ovarian cancer. Stage I, II, III, or IV cancer may be treated according to the present invention. Any mammal, preferably a human, may be treated according to the present invention.

It is particularly contemplated that the cancer is associated with formation of solid tumors, including carcinomas, such as adenocarcinomas and epithelial carcinomas. Such cancers can include, but are not limited to, lung cancer, including non-small cell lung cancer, and large cell carcinoma types, as well as small cell lung cancer; colon cancer, including colon metastasized to liver and including colorectal cancers; breast cancer; and ovarian cancer, as mentioned above. Cancers that can be associated with solid tumors further include, but are not limited to, kidney or renal cancers, including, for example, renal cell carcinomas; cancer of the bladder; liver cancer, including, for example, hepatocellular carcinomas; cancer of the gastrointestinal tract, including rectal, esophageal, pancreatic, and stomach cancer; gynecological cancers, including cervical, uterine, and endometrial cancers; prostate cancer or testicular cancer; nasopharyngeal cancer; thyroid cancer, for example, thyroid papillary carcinoma; cancer of the head, neck, or brain; nervous system cancers, including neuroblastomas; skin cancers, including melanomas; and sarcomas (including, for example, osteosarcomas and Ewing's sarcomas). Carcinomas include, but are not limited to, adenocarcinomas and epithelial carcinomas.

Hematological malignancies are cancers that affect blood, bone marrow, and lymph nodes and include leukemia, lymphomas, and myeloma. Such malignancies are typically associated with formation of non-solid tumors or non-solid tumor masses. Underlying genetic alterations, particularly chromosomal translocations, are a common cause of hematological malignancy, affecting the approach to diagnosis and treatment of these disorders.

Leukemia is characterized by an abnormal proliferation of white blood cells (leukocytes) or myeloid precursors. Displacement of normal marrow with increasing numbers of malignant cells results in a lack of blood platelets (thrombocytopenia), which are important in blood clotting, and red blood cells, which provide oxygen to the tissues of the body. Thus, patients with leukemia may bruise easily, bleed excessively, and suffer from anemia. Additionally, the number of functional white blood cells is often reduced, making leukemia patients susceptible to infection. Types of leukemia include acute lymphoblastic leukemia (ALL), characterized by overproduction of malignant and immature white blood cells; chronic lymphocytic leukemia (CLL); acute and chronic myelogenous leukemia (AML and CML, respectively), characterized by increased myeloid precursors in the blood and bone marrow; hairy cell leukemia, a rare leukemia also known as leukemic reticuloendotheliosis; and myelogenous leukemia. Leukemias may originate from myeloid bone marrow or lymph nodes. Leukemias may be acute, exhibited by maturation arrest at a primitive stage of development, and chronic, exhibited by excess accrual of mature lymphoid or myeloid cells.

Lymphomas originate in cells, primarily lymphocytes, of the reticuloendothelial system, which includes the lymph nodes and lymphatic organs such as spleen, thymus, tonsils, etc. Lymphomas include Hodgkin's lymphoma, characterized by the presence of large, often binucleated malignant cells known as Reed-Sternberg cells; and non-Hodgkin lymphoma, which includes a variety of lymphomas in which Reed-Sternberg cells are absent.

Multiple myeloma (MM) is a cancer of post-germinal center B-lymphocytes, and can affect several organs due to proliferation of the cancer cells, deposition of antibody, and overproduction of cytokines. Common ailments associated with MM include renal failure, polyneuropathy, bone lesions, and anemia. The anemia is usually normocytic and normochromic, and results from replacement of normal bone marrow by infiltrating tumor cells and inhibition of normal red blood cell production by cytokines.

Treatment for aggressive or acute forms of hematological malignancy often involves one or more of chemotherapy, radiotherapy, immunotherapy, and bone marrow transplantation. Radiation therapy may be used to reduce disease burden or as part of the preparation for a bone marrow transplant. Although complete remission of some hematological malignancies may be obtained in newly diagnosed adults, only 20%-30% have remission-free long-term survival. While such therapies may provide some relief to certain patients, a substantial need remains for effective therapies for reducing the progress of and complications associated with hematological malignancies.

Accordingly, it is also contemplated herein with respect to the present methods that the cancer is a hematological malignancy. Hematological malignancies include, but are not limited to, leukemias, including, but not limited to, acute myeloid leukemia (AML), chronic myelogenous leukemia (CML), acute lymphoblastic or precursor lymphoblastic leukemia, chronic lymphocytic leukemia (CLL), and hairy cell leukemia; lymphomas, e.g., mature B cell neoplasms, mature T cell and natural killer (NK) cell neoplasms, Hodgkin's lymphoma, immunodeficiency-associated lymphoproliferative disorders, and histiocytic and dendritic cell neoplasms, etc.; and myelomas, such as multiple myelomas.

In one embodiment, the invention provides a method for treating or preventing cancer in a subject, the method comprising stabilizing HIFα in the subject. In one aspect, the method for treating or preventing cancer in a subject comprises administering to the subject an agent that stabilizes HIFα. In another embodiment, the invention provides a method for treating or preventing cancer in a subject, the method comprising inhibiting HIF hydroxylase activity in the subject. In a preferred embodiment, the invention provides a method for treating or preventing cancer in a subject, the method comprising inhibiting HIF prolyl hydroxylase activity in the subject. In another embodiment, the invention provides a method for treating or preventing cancer in a subject by administering to the subject an agent selected from the group consisting of 2-oxoglutarate mimetics, iron chelators, and proline analogs. In another embodiment, methods are provided for treating or preventing cancer in a subject by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

The invention further provides methods for increasing subject survival. In one aspect, the method for increasing subject survival comprises stabilizing HIFα in the subject. In another embodiment, the method for increasing subject survival comprises administering to the subject an agent that stabilizes HIFα. In another embodiment, the invention provides a method for increasing subject survival, the method comprising inhibiting HIF hydroxylase activity in the subject. In a preferred embodiment, the invention provides a method for increasing subject survival, the method comprising inhibiting HIF prolyl hydroxylase activity in the subject. In another embodiment, the invention provides a method for increasing subject survival by administering to the subject an agent selected from the group consisting of 2-oxoglutarate mimetics, iron chelators, and proline analogs. In another embodiment, methods are provided for increasing subject survival by administering to the subject an agent selected from the group consisting of Compound A, Compound B, Compound C, Compound D, and Compound E. Further exemplary compounds of the invention include Compound F, Compound G, Compound H, Compound I, Compound J, Compound K, Compound L, Compound M, and Compound N.

HIFα refers to the alpha subunit of hypoxia inducible factor protein. HIFα may be any human or other mammalian protein, or fragment thereof, including human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example by using all or part of a HIFα gene sequence described above as a probe to recover and determine the sequence of a HIFα gene in another species.

A HIF prolyl hydroxylase is any enzyme capable of hydroxylating a proline residue in the HIF protein. Preferably, the proline residue hydroxylated by HIF prolyl hydroxylase includes the proline found within the motif LXXLAP, e.g., as occurs in the human HIF-1α native sequence at $L_{397}$TLLAP and $L_{559}$EMLAP. HIF prolyl hydroxylase includes members of the Egl-Nine (EGLN) gene family described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). Examples of HIF prolyl hydroxylase enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF prolyl hydroxylase may include *Caenorhabditis elegans* EGL-9 (GenBank Accession No. AAD56365) and *Drosophila melanogaster* CG1114 gene product (GenBank Accession No. AAF52050). HIF prolyl hydroxylase also includes any fragment of the foregoing full-length proteins that retain at least one structural or functional characteristic.

A HIF hydroxylase inhibitor or an agent that inhibits HIF hydroxylase is any agent that reduces or otherwise modulates the activity of HIF prolyl hydroxylase enzyme. Compounds that can be used in the methods of the invention include, for example, iron chelators, 2-oxoglutarate mimetics, and modified amino acid, e.g., proline, analogs.

In particular embodiments, the present invention provides for use of structural mimetics of 2-oxoglutarate. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; and Majamaa et al. (1985) Biochem J 229:127-133.) Prolyl hydroxylase inhibitors specifically contemplated for use in the present methods are described, e.g., in Majamaa et al., supra; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19):812 815; Franklin et al. (2001) Biochem J 353:333-338; and International Publication Nos. WO 03/053977 and WO 03/049686, each incorporated by reference herein in its entirety. Exemplary HIF prolyl hydroxylase inhibitors, including (1-Chloro-4-hydroxy-isoquinoline-3-carbonyl)-amino]-acetic acid (compound A); (S)-2-[(4-Hydroxy-7-phenoxy-6,7-dihydro-isoquinoline-3-carbonyl)-amino]-propionic acid (compound B); {[4-Hydroxy-7-(4-methoxy-phenoxy)-isoquinoline-3-carbonyl]-amino}-acetic acid (compound C); [(4-Hydroxy-1-methyl-7-phenoxy-isoquinoline-3-carbonyl)-amino]-acetic acid (compound D); and [7-(4-Fluoro-phenoxy)-4-hydroxy-isoquinoline-3-carbonyl]-amino-acetic acid (compound E), are used in the present examples to demonstrate the methods of the invention described herein. Further exemplary HIF prolyl hydroxylase inhibitors used in the present examples to demonstrate the methods of the invention described herein include Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1, 7-diphenoxy-isoquinoline-3-carbonyl)-amino]-acetic acid], and Compound N [(4-hydroxy-7-phenylsulfanyl-isoquinoline-3-carbonyl)-amino]-acetic acid.

Methods

Various methods are provided herein. In one aspect, the methods comprise administering to a subject an agent that stabilizes HIFα. Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. (See, e.g., U.S. Pat. Nos. 6,562,799 and 6,124,131; and U.S. Pat. No. 6,432,927.) In other aspects, the present invention contemplates that stabilizing HIFα comprises administering an agent that stabilizes HIFα. The agent can be composed of polynucleotides, e.g. antisense sequences (see, e.g., International Publication No. WO 03/045440); polypeptides; antibodies; other proteins; carbohydrates; fats; lipids; and organic and inorganic substances, e.g., small molecules, etc. In a preferred embodiment, the present invention contemplates stabilizing HIFα, e.g., in a subject, by administering to the subject an agent that stabilizes HIFα wherein the agent is a compound, e.g., small molecule compound, etc., that stabilizes HIFα.

In other embodiments, the methods of the invention comprise stabilizing HIFα by inhibiting HIF hydroxylase activity. HIF hydroxylase activity can include, e.g., the activity of any enzyme selected from the group consisting of HIF prolyl hydroxylase, HIF asparaginyl hydroxylase, and HIF lysyl hydroxylase. In preferred embodiments, the enzyme is a HIF prolyl hydroxylase enzyme, e.g., EGLN-1, EGLN-2, EGLN-3, etc. (See, e.g., Taylor (2001) Gene 275:125-132; Epstein et al. (2001) Cell 107:43-54; and Bruick and McKnight (2001) Science 294:1337-1340.)

Compounds

In preferred methods, the present methods comprise administering to a subject an effective amount of a compound that stabilizes HIFα. Exemplary compounds are disclosed in, e.g., International Publication No. WO 03/049686, International Publication No. WO 03/053997, International Publication No. WO 04/108121, and International Publication No. WO 04/108681, each of which is incorporated herein by reference in their entireties.

For example, International Publication No. WO 03/049686, International Publication No. WO 03/053997, International Publication No. WO 04/108121, and International Publication No. WO 04/108681 disclose exemplary compounds according to Formula I, below. These compounds include, but are not limited to, compounds of Formulae Ia, Ib, Ic, and Id. Further exemplary compounds are according to Formula Ie, including, but not limited to, compounds of Formulae Ie(i), Ie(ii), Ie(iii), and Ie(iv), as described below. International Publication No. WO 03/049686 and International Publication No. WO 03/053997 disclose exemplary compounds according to Formula II, below. Exemplary compounds according to Formula III, shown below, are disclosed in International Publication No. WO 03/049686, International Publication No. WO 03/053997, and International Publication No. WO 04/108121. These compounds include, but are not limited to, compounds of Formula IIIa. Further exemplary compounds are according to Formula IV, as described below.

In certain embodiments, a compound of the invention is a compound that inhibits HIF hydroxylase activity. In various embodiments, the activity is due to a HIF prolyl hydroxylase, such as, for example, EGLN1, EGLN2, or EGLN3, etc. In other embodiments, the activity is due to a HIF asparaginyl hydroxylase, such as, for example, including, but not limited to, FIH. A preferred compound of the invention is a compound that inhibits HIF prolyl hydroxylase activity. The inhibition can be direct or indirect, can be competitive or noncompetitive, etc.

In one aspect, a compound of the invention is any compound that inhibits or otherwise modulates the activity of a 2-oxoglutarate dioxygenase enzyme. 2-oxoglutarate dioxygenase enzymes include, but are not limited to, hydroxylase enzymes. Hydroxylase enzymes hydroxylate target substrate residues and include, for example, prolyl, lysyl, asparaginyl (asparagyl, aspartyl) hydroxylases, etc. Hydroxylases are sometimes described by target substrate, e.g., HIF hydroxylases, procollagen hydroxylases, etc., and/or by targeted residues within the substrate, e.g., prolyl hydroxylases, lysyl hydroxylases, etc., or by both, e.g., HIF prolyl hydroxylases, procollagen prolyl hydroxylases, etc. Representative 2-oxoglutarate dioxygenase enzymes include, but are not limited to, HIF hydroxylases, including HIF prolyl hydroxylases, e.g., EGLN1, EGLN2, and EGLN3, HIF asparaginyl hydroxylases, e.g., factor inhibiting HIF (FIH), etc.; procollagen hydroxylases, e.g., procollagen lysyl hydroxylases, procollagen prolyl hydroxylases, e.g., procollagen prolyl 3-hydroxylase, procollagen prolyl 4-hydroxylase α(I) and α(II), etc.; thymine 7-hydroxylase; aspartyl (asparaginyl) β-hydroxylase; ε-N-trimethyllysine hydroxylase; γ-butyrobetaine hydroxylase, etc. Although enzymatic activity can include any activity associated with any 2-oxoglutarate dioxygenase, the hydroxylation of amino acid residues within a substrate is specifically contemplated. Although hydroxylation of proline and/or asparagine residues within a substrate is specifically included, hydroxylation of other amino acids is also contemplated.

In one aspect, a compound of the invention that shows inhibitory activity toward one or more 2-oxoglutarate dioxygenase enzyme may also show inhibitory activity toward one or more additional 2-oxoglutarate dioxygenase enzymes, e.g., a compound that inhibits the activity of a HIF hydroxylase may additionally inhibit the activity of a collagen prolyl hydroyxlase, a compound that inhibits the activity of a HIF prolyl hydroylxase may additionally inhibit the activity of a HIF asparaginyl hydroylxase, etc.

In some aspects, compounds of the present invention include, for example, structural mimetics of 2-oxoglutarate. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; and Majamaa et al. Biochem J 229:127-133.)

In certain embodiments, a compound of the present invention is a compound of Formula I. In particular embodiments, the 2-oxoglutarate mimetic is a pyridine-2-carboxamide including, but not limited to, compounds of Formula I. In particular embodiments, the 2-oxoglutarate mimetic is a quinoline-2-carboxamide including, but not limited to, compounds of Formula Ia. In other embodiments, the 2-oxoglutarate mimetic is an isoquinoline-3-carboxamide including, but not limited to, compounds of Formula Ib. In additional embodiments, the 2-oxoglutarate mimetic is a cinnoline-3-carboxamide including, but not limited to, compounds of Formula Ic, or is a beta-carboline-3-carboxamide including, but not limited to, compounds of Formula Id.

As stated above, in certain embodiments, a compounds of the present invention is a compound of Formula I

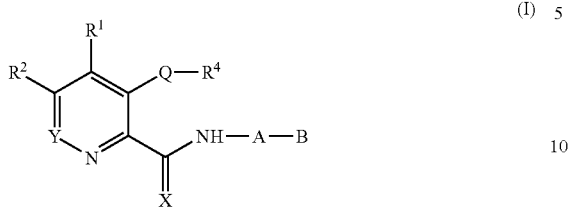

(I)

wherein

A is 1,2-arylidene, 1,3-arylidene, 1,4-arylidene; or ($C_1$-$C_4$)-alkylene, optionally substituted by one or two halogen, cyano, nitro, trifluoromethyl, ($C_1$-$C_6$)-alkyl, ($C_1$-$C_6$)-hydroxyalkyl, ($C_1$-$C_6$)-alkoxy, —O—[$CH_2$]$_x$—$C_fH_{(2f+1-g)}$Hal$_g$, ($C_1$-$C_6$)-fluoroalkoxy, ($C_1$-$C_8$)-fluoroalkenyloxy, ($C_1$-$C_8$)-fluoroalkynyloxy, —OCF$_2$Cl, —O—CF$_2$—CHFCl; ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, phenyl, benzyl, phenoxy, benzyloxy, anilino, N-methylanilino, phenylmercapto, phenylsulfonyl, phenylsulfinyl, sulfamoyl, N—($C_1$-$C_4$)-alkylsulfamoyl, N,N-di-($C_1$-$C_4$)-alkylsulfamoyl; or by a substituted ($C_6$-$C_{12}$)-aryloxy, ($C_7$-$C_{11}$)-aralkyloxy, ($C_6$-$C_{12}$)-aryl, ($C_7$-$C_{11}$)-aralkyl radical, which carries in the aryl moiety one to five identical or different substituents selected from halogen, cyano, nitro, trifluoromethyl, ($C_1$-$C_6$)-alkyl, ($C_1$-$C_6$)-alkoxy, —O—[$CH_2$]$_x$—$C_fH_{(2f+1-g)}$Hal$_g$, —OCF$_2$Cl, —O—CF$_2$—CHFCl, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, sulfamoyl, N—($C_1$-$C_4$)-alkylsulfamoyl, N,N-di-($C_1$-$C_4$)-alkylsulfamoyl; or wherein A is —CR$^5$R$^6$ and R$^5$ and R$^6$ are each independently selected from hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —CO$_2$H, —NH$_2$, —NHSO$_2$CF$_3$, tetrazolyl, imidazolyl, 3-hydroxyisoxazolyl, —CONHCOR''', —CONHSOR''', CONHSO$_2$R''', where R''' is aryl, heteroaryl, ($C_3$-$C_7$)-cycloalkyl, or ($C_1$-$C_4$)-alkyl, optionally monosubstituted by ($C_6$-$C_{12}$)-aryl, heteroaryl, OH, SH, ($C_1$-$C_4$)-alkyl, ($C_1$-$C_4$)-alkoxy, ($C_1$-$C_4$)-thioalkyl, ($C_1$-$C_4$)-sulfinyl, ($C_1$-$C_4$)-sulfonyl, CF$_3$, Cl, Br, F, I, NO2, —COOH, ($C_2$-$C_5$)-alkoxycarbonyl, NH$_2$, mono-($C_1$-$C_4$-alkyl)-amino, di-($C_1$-$C_4$-alkyl)-amino, or ($C_1$-$C_4$)-perfluoroalkyl;

or wherein B is a CO$_2$-G carboxyl radical, where G is a radical of an alcohol G-OH in which G is selected from ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical, where the alkenyl, cycloalkenyl, alkynyl, and alkenynyl radicals contain one or more multiple bonds; ($C_6$-$C_{16}$)-carbocyclic aryl radical, ($C_7$-$C_{16}$)-carbocyclic aralkyl radical, heteroaryl radical, or heteroaralkyl radical, wherein a heteroaryl radical or heteroaryl moiety of a heteroaralkyl radical contains 5 or 6 ring atoms; and wherein radicals defined for G are substituted by one or more hydroxyl, halogen, cyano, trifluoromethyl, nitro, carboxyl, ($C_1$-$C_{12}$)-alkyl, ($C_3$-$C_8$)-cycloalkyl, ($C_5$-$C_8$)-cycloalkenyl, ($C_6$-$C_{12}$)-aryl, ($C_7$-$C_{16}$)-aralkyl, ($C_2$-$C_{12}$)-alkenyl, ($C_2$-$C_{12}$)-alkynyl, ($C_1$-$C_{12}$)-alkoxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_6$-$C_{12}$)-aryloxy, ($C_7$-$C_{16}$)-aralkyloxy, ($C_1$-$C_8$)-hydroxyalkyl, —O—[$CH_2$]$_x$—$C_fH_{(2f+1-g)}$—F$_g$, —OCF$_2$Cl, —OCF$_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{12}$)-alkenylcarbonyl, ($C_2$-$C_{12}$)-alkynylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, acyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$) aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N.N-di($C_1$-$C_{12}$)-alkylcarbamoyl, N—($C_3$-$C_8$)-cycloalkyl-carbamoyl, N—($C_6$-$C_{16}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{10}$)-alkoxy-($C_1$-$C_{10}$)-alkyl)-carbamoyl, N—(($C_6$-$C_{12}$)-aryloxy-($C_1$-$C_{10}$)alkyl)-carbamoyl, N—(($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{16}$)-aryloxy-($C_1$-$C_{10}$)-alkyl)-carbamoyl, N—($C_1$-$C_{10}$)-alkyl-N—(($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N.N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxy, amino, ($C_1$-$C_{12}$)-alkylamino, di-($C_1$-$C_{12}$)-alkylamino, ($C_3$-$C_8$)-cycloalkylamino, ($C_2$-$C_{12}$)-alkenylamino, ($C_2$-$C_{12}$)-alkynylamino, N—($C_6$-$C_{12}$)-arylamino, N—($C$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkylcarbonylamino, ($C_3$-$C_8$)-cycloalkylcarbonylamino, ($C_6$-$C_{12}$) arylcarbonylamino, ($C_7$-$C_{16}$)-aralkylcarbonylamino, ($C_1$-$C_{12}$)-alkylcarbonyl-N—($C_1$-$C_{10}$)-alkylamino, ($C_3$-$C_8$)-cycloalkylcarbonyl-N—($C_1$-$C_{10}$)-alkylamino, ($C_6$-$C_{12}$)-arylcarbonyl-N—($C_1$-$C_{10}$)alkylamino, ($C_7$-$C_{11}$)-aralkylcarbonyl-N—($C_1$-$C_{10}$)-alkylamino, ($C_1$-$C_{12}$)-alkylcarbonylamino-($C_1$-$C_8$)-alkyl, ($C_3$-$C_8$)-cycloalkylcarbonylamino-($C_1$-$C_8$)alkyl, ($C_6$-$C_{12}$)-arylcarbonylamino-($C_1$-$C_8$)-alkyl, ($C_7$-$C_{12}$)-aralkylcarbonylamino-($C_1$-$C_8$)-alkyl, amino-($C_1$-$C_{10}$)-alkyl, N—($C_1$-$C_{10}$) alkylamino-($C_1$-$C_{10}$)-alkyl, N.N-di-($C_1$-$C_{10}$)-alkylamino-($C_1$-$C_{10}$)-alkyl, ($C_3$-$C_8$)

cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N.N-di($C_1$-$C_{10}$)-alkylsulfamoyl, ($C_3$-$C_8$)-cycloalkylsulfamoyl, N—($C_6$-$C_{12}$)-alkylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N—(($C_1$-$C_{10}$)-alkyl)-($C_1$-$C_{10}$)-alkylsulfonamido, ($C_7$-$C_{16}$)-aralkylsulfonamido, or N—(($C_1$-$C_{10}$)-alkyl-($C_7$-$C_{16}$)-aralkylsulfonamido; wherein radicals which are aryl or contain an aryl moiety, may be substituted on the aryl by one to five identical or different hydroxyl, halogen, cyano, trifluoromethyl, nitro, carboxyl, ($C_1$-$C_{12}$)-alkyl, ($C_3$-$C_8$)-cycloalkyl, ($C_6$-$C_{12}$)-aryl, ($C_7$-$C_{16}$)-aralkyl, ($C_1$-$C_{12}$)-alkoxy, ($C_1$-$C_{12}$)-alkoxy-($C_1$-$C_{12}$)alkyl, ($C_1$-$C_{12}$)-alkoxy-($C_1$-$C_{12}$) alkoxy, ($C_6$-$C_{12}$)-aryloxy, ($C_7$-$C_{16}$)-aralkyloxy, ($C_1$-$C_8$)-hydroxyalkl, ($C_1$-$C_{12}$)-alkylcarbonyl, ($C_3$-$C_8$)-cycloalkyl-carbonyl, ($C_6$-$C_{12}$)-arylcarbonyl, ($C_7$-$C_{16}$) aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N.N-di-($C_1$-$C_{12}$)-alkylcarbamoyl, N—($C_3$-$C_8$)-cycloalkylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{12}$)-arylcarbamoyl, N—($C_1$-$C_{10}$)-alkyl-N—($C_7$-$C_{16}$)-aralkylcarbamoyl, N—(($C_1$-$C_{10}$)-alkoxy-($C_1$-$C_{10}$)-alkyl)-carbamoyl, N—(($C_6$-$C_{12}$)-aryloxy-($C_1$-$C_{10}$)-alkyl)-carbamoyl, N—(($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{12}$)-aryloxy-($C_1$-$C_{10}$)-alkyl)-carbamoyl, N—($C_1$-$C_{10}$)-alkyl-N—(($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N.N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkylaralkylamino, N-alkylarylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkylcarbonylamino, ($C_3$-$C_8$)-cycloalkylcarbonylamino, ($C_6$-$C_{12}$)-arylcarbonylamino, ($C_7$-$C_{16}$)-alkylcarbonylamino, ($C_1$-$C_{12}$)-alkylcarbonyl-N—($C_1$-$C_{10}$)-alkylamino, ($C_3$-$C_8$)-cycloalkylcarbonyl-N—($C_1$-$C_{10}$)-alkylamino, ($C_6$-$C_{12}$)-arylcarbonyl-N—($C_1$-$C_{10}$)-alkylamino, ($C_7$-$C_{16}$)-aralkylcarbonyl-N—($C_1$-$C_{10}$)-alkylamino, ($C_1$-$C_{12}$)-alkylcarbonylamino-($C_1$-$C_8$)-alkyl, ($C_3$-$C_8$)-cycloalkylcarbonylamino-($C_1$-$C_8$)-alkyl, ($C_6$-$C_{12}$)-arylcarbonylamino-($C_1$-$C_8$)-alkyl, ($C_7$-$C_{16}$)-aralkylcarbonylamino-($C_1$-$C_8$)-alkyl, amino-($C_1$-$C_{10}$)-alkyl, N—($C_1$-$C_{10}$)-alkylamino-($C_1$-$C_{10}$)alkyl, N.N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

X is O or S;

Q is O, S, NR', or a bond;

where, if Q is a bond, $R^4$ is halogen, nitrile, or trifluoromethyl;

or where, if Q is O, S, or NR', $R^4$ is hydrogen, ($C_1$-$C_{10}$)-alkyl radical, ($C_2$-$C_{10}$)-alkenyl radical, ($C_2$-$C_{10}$)-alkynyl radical, wherein alkenyl or alkynyl radical contains one or two C—C multiple bonds; unsubstituted fluoroalkyl radical of the formula

—[$CH_2$]$_x$—$C_fH_{(2f+1-g)}$—$F_g$, ($C_1$-$C_8$)-alkoxy-($C_1$-$C_6$)-alkyl radical, ($C_1$-$C_6$)-alkoxy-($C_1$-$C_4$)-alkoxy-($C_1$-$C_4$)-alkyl radical, aryl radical, heteroaryl radical, ($C_7$-$C_{11}$)-aralkyl radical, or a radical of the Formula Z —[$CH_2$]$_v$—[O]$_w$—[$CH_2$]$_t$-E  (Z)

where

E is a heteroaryl radical, a ($C_3$-$C_8$)-cycloalkyl radical, or a phenyl radical of the Formula F

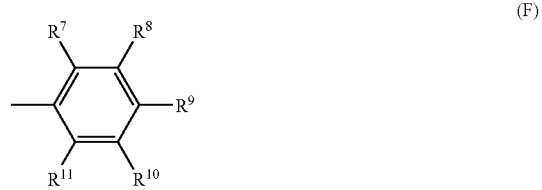

v is 0-6, w is 0 or 1, t is 0-3, and $R^7$, $R^8$, $R^9$, $R^{10}$, and $R^{11}$ are identical or different and are hydrogen, halogen, cyano, nitro, trifluoromethyl, ($C_1$-$C_6$)-alkyl, ($C_3$-$C_8$)-cycloalkyl, ($C_1$-$C_6$)-alkoxy, —O—[$CH_2$]$_x$—$C_fH_{(2f+1-g)}$—$F_g$, —$OCF_2$—Cl, —O—$CF_2$—CHFCl, ($C_1$-$C_6$)-alkylmercapto, ($C_1$-$C_6$)-hydroxyalkyl, ($C_1$-$C_6$)-alkoxy-($C_1$-$C_6$)-alkoxy, ($C_1$-$C_6$)-alkoxy-($C_1$-$C_6$)-alkyl, ($C_1$-$C_6$)-alkylsulfinyl, ($C_1$-$C_6$)-alkylsulfonyl, ($C_1$-$C_6$)-alkylcarbonyl, ($C_1$-$C_8$)-alkoxycarbonyl, carbamoyl, N—($C_1$-$C_8$)-alkylcarbamoyl, N,N-di-($C_1$-$C_8$)-alkylcarbamoyl, or ($C_7$-$C_{11}$)-aralkylcarbamoyl, optionally substituted by fluorine, chlorine, bromine, trifluoromethyl, ($C_1$-$C_6$)-alkoxy, N—($C_3$-$C_8$)-cycloalkylcarbamoyl, N—($C_3$-$C_8$)-cycloalkyl-($C_1$-$C_4$)-alkylcarbamoyl, ($C_1$-$C_6$)-alkylcarbonyloxy, phenyl, benzyl, phenoxy, benzyloxy, $NR^yR^z$ wherein $R^y$ and $R^z$ are independently selected from hydrogen, ($C_1$-$C_{12}$)- alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_3-C_{10})$-cycloalkyl, $(C_3-C_{12})$-alkenyl, $(C_3-C_{12})$-alkynyl, $(C_6-C_{12})$-aryl, $(C_7-C_{11})$-aralkyl, $(C_1-C_{12})$-alkoxy, $(C_7-C_{12})$aralkoxy, $(C_1-C_{12})$-alkylcarbonyl, $(C_3-C_8)$-cycloalkylcarbonyl, $(C_6-C_{12})$ arylcarbonyl, $(C_7-C_{16})$-aralkylcarbonyl; or further wherein $R^y$ and $R^z$ together are —[CH2]$_n$, in which a $CH_2$ group can be replaced by O, S, N—$(C_1-C_4)$-alkylcarbonylimino, or N—$(C_1-C_4)$-alkoxycarbonylimino; phenylmercapto, phenylsulfonyl, phenylsulfinyl, sulfamoyl, N—$(C_1-C_8)$-alkylsulfamoyl, or N, N-di-$(C_1-C_8)$-alkylsulfamoyl; or alternatively $R^7$ and $R^8$, $R^8$ and $R^9$, $R^9$ and $R^{10}$, or $R^{10}$ and $R^{11}$, together are a chain selected from —[CH$_2$]$_n$— or —CH═CH—CH═CH—, where a $CH_2$ group of the chain is optionally replaced by O, S, SO, SO$_2$, or NR$^Y$; and n is 3, 4, or 5; and if E is a heteroaryl radical, said radical can carry 1-3 substituents selected from those defined for $R^7-R^{11}$, or if E is a cycloalkyl radical, the radical can carry one substituent selected from those defined for $R^7-R^{11}$;

or where, if Q is NR', $R^4$ is alternatively R", where R' and R" are identical or different and are hydrogen, $(C_6-C_{12})$-aryl, $(C_7-C_{11})$-aralkyl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkylcarbonyl, optionally substituted $(C_7-C_{16})$-aralkylcarbonyl, or optionally substituted $C_6-C_{12}$)-arylcarbonyl; or R' and R" together are —[CH$_2$]$_h$, in which a $CH_2$ group can be replaced by O, S, N-acylimino, or N—$(C_1-C_{10})$-alkoxycarbonylimino, and h is 3 to 7.

Y is N or CR$^3$;

$R^1$, $R^2$ and $R^3$ are identical or different and are hydrogen, hydroxyl, halogen, cyano, trifluoromethyl, nitro, carboxyl, $(C_1-C_{20})$-alkyl, $(C_3-C_8)$-cycloalkyl, $(C_3-C_8)$cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_1-C_{20})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_{16})$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, $(C_2-C_{20})$-alkenyloxy-$(C_1-C_6)$-alkyl, $(C_2-C_{20})$-alkynyloxy-$(C_1-C_6)$-alkyl, retinyloxy-$(C_1-C_6)$-alkyl, —O—[CH$_2$]$_x$CfH$_{(2f+1-g)}$F$_g$, —OCF$_2$Cl, —OCF$_2$—CHFCl, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)-carbamoyl, N—$(C_1-C_6)$-alkyl-N—$((C_3-C_8)$-cycloalkyl-$(C_1-C_6)$-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, N—$((C_1-C_{18})$-alkoxy-$(C_1-C_{10})$-alkyl)-carbamoyl, N—$((C_6-C_{16})$-aryloxy-$(C_1-C_{10})$-alkyl)-carbamoyl, N—$((C_7-C_{16})$-aralkyloxy-$(C_1-C_{10})$-alkyl)-carbamoyl, N—$(C_1-C_{10})$-alkyl-N—$((C_1-C_{10})$-alkoxy-$(C_1-C_{10})$-alkyl)-carbamoyl, N—$(C_1-C_{10})$-alkyl-N—$((C_6-C_{12})$-aryloxy-$(C_1-C_{10})$-alkyl)-carbamoyl, N—$(C_1-C_{10})$-alkyl-N—$((C_7-C_{16})$-aralkyloxy-$(C_1-C_{10})$-alkyl)-carbamoyl; CON(CH$_2$)$_h$, in which a $CH_2$ group can be replaced by O, S, N—$(C_1-C_8)$-alkylimino, N—$(C_3-C_8)$-cycloalkylimino, N—$(C_3-C_8)$-cycloalkyl-$(C_1-C_4)$-alkylimino, N—$(C_6-C_{12})$-arylimino, N—$(C_7-C_{16})$-aralkylimino, N—$(C_1-C_4)$-alkoxy-$(C_1-C_6)$-alkylimino, and h is from 3 to 7; a carbamoyl radical of the Formula R

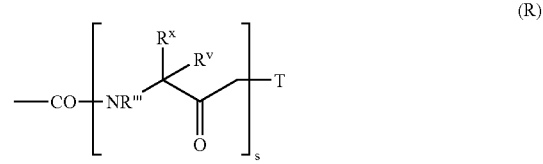

(R)

in which $R^x$ and $R^v$ are each independently selected from hydrogen, $(C_1-C_6)$-alkyl, $(C_3-C_7)$-cycloalkyl, aryl, or the substituent of an α-carbon of an α-amino acid, to which the L- and D-amino acids belong, s is 1-5, T is OH, or NR*R**, and R*, R and R* are identical or different and are selected from hydrogen, $(C_6-C_{12})$-aryl, $(C_7-C_{11})$-aralkyl, $(C_1-C_8)$-alkyl, $(C_3-C_8)$-cycloalkyl, (+)-dehydroabietyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl, optionally substituted $(C_6-C_{12})$-aroyl; or R* and R** together are —[CH$_2$]$_h$, in which a $CH_2$ group can be replaced by O, S, SO, SO$_2$, N-acylamino, N—$(C_1-C_{10})$-alkoxycarbonylimino, N—$(C_1-C_8)$-alkylimino, N—$(C_3-C_8)$-cycloalkylimino, N—$(C_3-C_8)$-cycloalkyl-$(C_1-C_4)$-alkylimino, N—$(C_6-C_{12})$-arylimino, N—$(C_7-C_{16})$-aralkylimino, N—$(C_1-C_4)$-alkoxy-$(C_1-C_6)$-alkylimino, and h is from 3 to 7;

carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di($C_1$-$C_{10}$)-alkylamino-($C_1$-$C_{10}$)-alkyl, ($C_3$-$C_8$)-cycloalkylamino($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, ($C_1$-$C_{12}$)-alkylmercapto-($C_1$-$C_6$)-alkyl, ($C_1$-$C_{12}$)-alkylsulfinyl-($C_1$-$C_6$)-alkyl, ($C_1$-$C_{12}$)-alkylsulfonyl-($C_1$-$C_6$)-alkyl, ($C_6$-$C_{12}$)-arylmercapto-($C_1$-$C_6$)-alkyl, ($C_6$-$C_{12}$)-arylsulfinyl-($C_1$-$C_6$)-alkyl, ($C_6$-$C_{12}$)-arylsulfonyl-($C_1$-$C_6$)-alkyl, ($C_7$-$C_{16}$)-aralkylmercapto-($C_1$-$C_6$)-alkyl, ($C_7$-$C_{16}$)-aralkylsulfinyl-($C_1$-$C_6$)-alkyl, ($C_7$-$C_{16}$)-aralkylsulfonyl-($C_1$-$C_6$)-alkyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N—(($C_1$-$C_{10}$)-alkyl)-($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido;
where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, $C_1$-$C_8$)-hydroxyalkyl, ($C_6$-$C_{12}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, —O—[$CH_2$]$_x$$C_f$$H_{(2f+1-g)}$$F_g$, —$OCF_2Cl$, —$OCF_2$—$CHFCl$, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynylcarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, $CON(CH_2)_h$, in which a $CH_2$ group can be replaced by, O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{16}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)carbamoyloxy, N—(($C_6$-$C_{12}$)-aryloxy-($C_1$-$C_{10}$)-alkyl)carbamoyloxy, N—(($C_7$-$C_{16}$)-aralkyloxy-($C_1$-$C_{10}$)-alkyl)carbamoyloxy, N—($C_1$-$C_{10}$)-alkyl-N—(($C_1$-$C_{10}$)-alkoxy-($C_1$-$C_{10}$)-alkyl)carbamoyloxy, N—($C_1$-$C_{10}$)-alkyl-N—(($C_6$-$C_{12}$)-aryloxy-($C_1$-$C_{10}$)-alkyl)carbamoyloxy, N—($C_1$-$C_{10}$)-alkyl-N—(($C_7$-$C_{16}$)-aralkyloxy-($C_1$-$C_{10}$)-alkyl)carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)- aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{12})$-aroylamino-$(C_1-C_8)$-alkyl, $(C_7-C_{16})$-aralkanoylamino-$(C_1-C_8)$-alkyl, amino-$(C_1-C_{10})$-alkyl, N—$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, or $(C_7-C_{16})$-aralkylsulfonyl;

or wherein $R^1$ and $R^2$, or $R^2$ and $R^3$ form a chain $[CH_2]_o$, which is saturated or unsaturated by a C=C double bond, in which 1 or 2 $CH_2$ groups are optionally replaced by O, S, SO, $SO_2$, or NR', and R' is hydrogen, $(C_6-C_{12})$-aryl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl, or optionally substituted $(C_6-C_{12})$-aroyl; and o is 3, 4 or 5;

or wherein the radicals $R^1$ and $R^2$, or $R^2$ and $R^3$, together with the pyridine or pyridazine carrying them, form a 5,6,7,8-tetrahydroisoquinoline ring, a 5,6,7,8-tetrahydroquinoline ring, or a 5,6,7,8-tetrahydrocinnoline ring;

or wherein $R^1$ and $R^2$, or $R^2$ and $R^3$ form a carbocyclic or heterocyclic 5- or 6-membered aromatic ring;

or where $R^1$ and $R^2$, or $R^2$ and $R^3$, together with the pyridine or pyridazine carrying them, form an optionally substituted heterocyclic ring systems selected from thienopyridines, furanopyridines, pyridopyridines, pyrimidinopyridines, imidazopyridines, thiazolopyridines, oxazolopyridines, quinoline, isoquinoline, and cinnoline; where quinoline, isoquinoline or cinnoline preferably satisfy the Formulae Ia, Ib and Ic:

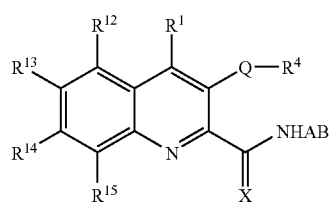

(Ia)

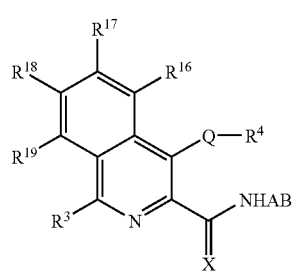

(Ib)

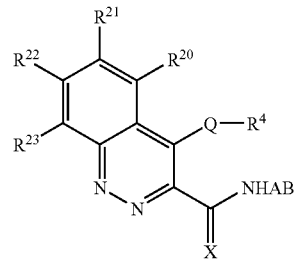

(Ic)

and the substituents $R^{12}$ to $R^{23}$ in each case independently of each other have the meaning of $R^1$, $R^2$ and $R^3$;

or wherein the radicals $R^1$ and $R^2$, together with the pyridine carrying them, form a compound of Formula Id:

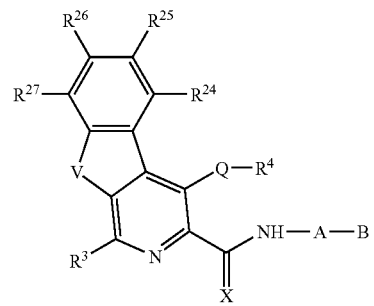

(Id)

where

V is S, O, or $NR^k$, and $R^k$ is selected from hydrogen, $(C_1-C_6)$-alkyl, aryl, or benzyl; where an aryl radical may be optionally substituted by 1 to 5 substituents as defined above; and $R^{24}$, $R^{25}$, $R^{26}$, and $R^{27}$ in each case independently of each other have the meaning of $R^1$, $R^2$ and $R^3$;

f is 1 to 8;

g is 0 or 1 to (2f+1);

x is 0 to 3; and h is 3 to 7;

including the physiologically active salts, esters, and prodrugs derived therefrom.

Exemplary compounds according to Formula I are described in European Patent Nos. EP0650960 and EP0650961. All compounds listed in EP0650960 and EP0650961, in particular, those listed in the compound claims and the final products of the working examples, are hereby incorporated into the present application by reference herein. Additionally, exemplary compounds according to Formula I are described in U.S. Pat. No. 5,658,933. All compounds listed in U.S. Pat. No. 5,658,933, in particular, those listed in the compound claims and the final products of the working examples, are hereby incorporated into the present application by reference herein.

Additional compounds according to Formula I are substituted heterocyclic carboxyamides described in U.S. Pat. No. 5,620,995; 3-hydroxypyridine-2-carboxamidoesters described in U.S. Pat. No. 6,020,350; sulfonamidocarbonylpyridine-2-carboxamides described in U.S. Pat. No. 5,607,954; and sulfonamidocarbonyl-pyridine-2-carboxamides and sulfonamidocarbonyl-pyridine-2-carboxamide esters described in U.S. Pat. Nos. 5,610,172 and 5,620,996. All compounds listed in these patents, in particular, those compounds listed in the compound claims and the final products of the working examples, are hereby incorporated into the present application by reference herein.

Exemplary compounds according to Formula Ia are described in U.S. Pat. Nos. 5,719,164 and 5,726,305. All compounds listed in the foregoing patents, in particular, those listed in the compound claims and the final products of the working examples, are hereby incorporated into the present application by reference herein. Exemplary compounds according to Formula Ib are described in U.S. Pat. No. 6,093,730. All compounds listed in U.S. Pat. No. 6,093,730, in particular, those listed in the compound claims and the final products of the working examples, are hereby incorporated into the present application by reference herein In certain embodiments, compounds of the invention are pyridine-2-carboxamides. In one embodiment, the compound is selected from a compound of the Formula I, wherein A is $-CR^5R^6-$, and $R^5$ and $R^6$ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is $-CO_2H$ or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;

X is O;

Q is O;

$R^4$ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C—C multiple bonds; unsubstituted fluoroalkyl radical of the formula $-[CH_2]_x-C_fH_{(2f+1-g)}-F_g$, aryl, heteroaryl, and ($C_7$-$C_{11}$)-aralkyl;

Y is $CR^3$;

$R^1$, $R^2$ and $R^3$ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, $-O-[CH_2]_xC_fH_{(2f+1-g)}F_g$, $-OCF_2Cl$, $-OCF_2-CHFCl$, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, $-O-[CH_2]_xC_fH_{(2f+1-g)}F_g$, $-OCF_2Cl$, and $-OCF_2-CHFCl$;

x is 0 to 3;

f is 1 to 8; and g is 0 or 1 to (2f+1);

including the physiologically active salts, esters, and prodrugs derived therefrom.

Pyridine-2-carboxamides of Formula I include, but are not limited to, [(3-methoxy-pyridine-2-carbonyl)-amino]-acetic acid, 3-methoxypyridine-2-carboxylic acid N-(((hexadecyloxy)-carbonyl)-methyl)-amide hydrochloride, 3-methoxypyridine-2-carboxylic acid N-(((1-octyloxy)-carbonyl)-methyl)-amide, 3-methoxypyridine-2-carboxylic acid N-(((hexyloxy)-carbonyl)-methyl)-amide, 3-methoxypyridine-2-carboxylic acid N-(((butyloxy)-carbonyl)-methyl)- amide, 3-methoxypyridine-2-carboxylic acid N-(((2-nonyloxy)-carbonyl)-methyl)-amide racemate, 3-methoxypyridine-2-carboxylic acid N-(((heptyloxy)-carbonyl)-methyl)-amide, 3-benzyloxypyridine-2-carboxylic acid N-(((octyloxy)-carbonyl)-methyl)-amide, 3-benzyloxypyridine-2-carboxylic acid N-(((butyloxy)-carbonyl)-methyl)-amide, 5-(((3-(1-butyloxy)-propyl)-amino)-carbonyl)-3-methoxypyridine-2-carboxylic acid N-((benzyloxycarbonyl)-methyl)-amide, 5-(((3-(1-butyloxy)-propyl)-amino)-carbonyl)-3-methoxypyridine-2-carboxylic acid N-(((1-butyloxy)-carbonyl)-methyl)-amide, 5-(((3-lauryloxy)-propyl)amino)-carbonyl)-3-methoxypyridine-2-carboxylic acid N-(((benzyloxy)-carbonyl)-methyl)-amide, [(3-hydroxy-pyridine-2-carbonyl)-amino]-acetic acid, and [(3-methoxy-pyridine-2-carbonyl)-amino]-acetic acid.

In certain embodiments, compounds of the invention are quinoline-2-carboxamides. In one embodiment, the compound is selected from a compound of the Formula Ia wherein A is —$CR^5R^6$—, and $R^5$ and $R^6$ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;

X is O;

Q is O;

$R^4$ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and ($C_7$-$C_{11}$)-aralkyl;

$R^1$, $R^{12}$, $R^{13}$, $R^{14}$ and $R^{15}$ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, —O—$[CH_2]_xCfH_{(2f+1-g)}F_g$, —$OCF_2Cl$, —$OCF_2$—$CHFCl$, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—$[CH_2]_xC_fH_{(2f+1-g)}F_g$, —$OCF_2Cl$, and —$OCF_2$—$CHFCl$;

x is 0 to 3;

f is 1 to 8; and g is 0 or 1 to (2f+1);

including the physiologically active salts, esters, and prodrugs derived therefrom.

Quinoline-2-carboxamides of Formula Ia include, but are not limited to, N-((3-Hydroxy-6-isopropoxy-quinoline-2-carbonyl)-amino)-acetic acid, N-((6-(1-butyloxy)-3-hydroxyquinolin-2-yl)-carbonyl)-glycine, [(3-hydroxy-6-trifluoromethoxy-quinoline-2-carbonyl)-amino]-acetic acid, [(7-Chloro-3-hydroxy-quinoline-2-carbonyl)-amino]-acetic acid] (Compound H), and [(6-chloro-3-hydroxy-quinoline-2-carbonyl)-amino]-acetic acid.

In certain embodiments, compounds of the invention are isoquinoline-3-carboxamides. In one embodiment, the compound is selected from a compound of the Formula Ib wherein A is —$CR^5R^6$—, and $R^5$ and $R^6$ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;

X is O;

Q is O;

$R^4$ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C=C multiple bonds; unsubstituted fluoroalkyl radical of the formula —[$CH_2$]$_x$—$C_fH_{(2f+1-g)}$—$F_g$, aryl, heteroaryl, and ($C_7$-$C_{11}$)-aralkyl;

$R^3$, $R^{16}$, $R^{17}$, $R^{18}$ and $R^{19}$ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, —O—[$CH_2$]$_x$$C_fH_{(2f+1-g)}$$F_g$, —$OCF_2C$, —$OCF_2$—CHFCl, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—[$CH_2$]$_x$$C_fH_{(2f+1-g)}$$F_g$, —$OCF_2Cl$, and —$OCF_2$—CHFCl;

x is 0 to 3;

f is 1 to 8; and g is 0 or 1 to (2f+1);

including the physiologically active salts, esters, and prodrugs derived therefrom.

In another embodiment, compounds of the invention are isoquinoline-3-carboxamides, such as disclosed in WO 2004/108681, represented by Formula Ie

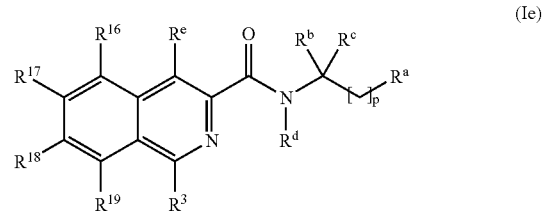

(Ie)

wherein p is zero or one;

$R^a$ is —COOH or —$WR^{50}$; provided that when $R^a$ is —COOH then p is zero and when $R^a$ is —$WR^{50}$ then p is one;

W is selected from the group consisting of oxygen, —S(O)$_n$— and —$NR^{51}$— where n is zero, one or two, $R^{51}$ is selected from the group consisting of hydrogen, alkyl, substituted alkyl, acyl, aryl, substituted aryl, heteroaryl, substituted heteroaryl, heterocyclic and substituted heterocyclic and $R^{50}$ is selected from the group consisting of hydrogen, alkyl, substituted alkyl, aryl, substituted aryl, heteroaryl, substituted heteroaryl, heterocyclic and substituted heterocyclic, or when W is —$NR^9$— then $R^{50}$ and $R^{51}$, together with the nitrogen atom to which they are bound, can be joined to form a heterocyclic or a substituted heterocyclic group, provided that when W is —S(O)$_n$— and n is one or two, then $R^{50}$ is not hydrogen;

$R^3$ is selected from the group consisting of hydrogen, alkyl, substituted alkyl, alkoxy, substituted alkoxy, amino, substituted amino, aminoacyl, aryl, substituted aryl, halo, heteroaryl, substituted heteroaryl, heterocyclic, substituted heterocyclic, and —$XR^{60}$ where X is oxygen, —S(O)$_n$— or —$NR^{70}$ where n is zero, one or two; $R^{60}$ is selected from the group consisting of alkyl, substituted alkyl, aryl, substituted aryl, heteroaryl, substituted heteroaryl, heterocyclic and substituted heterocyclic; and $R^{70}$ is hydrogen, alkyl or aryl; or, when X is —$NR^{70}$, then $R^{60}$ and $R^{70}$, together with the nitrogen atom to which they are bound, can be joined to form a heterocyclic or substituted heterocyclic group;

$R^{17}$ and $R^{18}$ are independently selected from the group consisting of hydrogen, alkyl, substituted alkyl, aryl, substituted aryl, heteroaryl, substituted heteroaryl, halo, hydroxy, cyano, —S(O)$_n$—N(R$^{80}$)—R$^{80}$ where n is 0, 1, or 2, —NR$^{80}$C(O)NR$^{80}$R$^{80}$, —XR$^{80}$ where X is oxygen, —S(O)$_n$— or —NR$^{90}$— where n is zero, one or two, each R$^{80}$ is independently selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic provided that when X is —SO— or —SO$_2$—, then R$^{80}$ is not hydrogen, and R$^{90}$ is selected from the group consisting of hydrogen, alkyl, aryl, or R$^{17}$, R$^{18}$ together with the carbon atom pendent thereto, form an aryl substituted aryl, heteroaryl, or substituted heteroaryl;

$R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —XR$^{60}$ where X is oxygen, —S(O)$_n$— or —NR$^{70}$— where n is zero, one or two, R$^{60}$ is selected from the group consisting of alkyl, substituted alkyl, aryl, substituted aryl, heteroaryl, substituted heteroaryl, heterocyclic and substituted heterocyclic, and R$^{70}$ is hydrogen, alkyl or aryl or, when X is —NR$^{70}$, then R$^{70}$ and R$^{60}$, together with the nitrogen atom to which they are bound, can be joined to form a heterocyclic or substituted heterocyclic group;

$R^b$ is selected from the group consisting of hydrogen, deuterium and methyl;

$R^c$ is selected from the group consisting of hydrogen, deuterium, alkyl and substituted alkyl; alternatively, $R^b$ and $R^c$ and the carbon pendent thereto can be joined to form cycloalkyl, substituted cycloalkyl, heterocyclic or substituted heterocyclic group;

$R^d$ is selected from the group consisting of hydrogen and alkyl or $R^d$ together with $R^e$ and the nitrogen pendent thereto can be joined to form a heterocyclic or substituted heterocyclic group; and $R^e$ is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, aryl, —S(O)$_n$—R$^{95}$ wherein R$^{95}$ is selected from the group consisting of alkyl, substituted alkyl, cycloalkyl, substituted cycloalkyl, aryl, substituted aryl, heteroaryl and substituted heteroaryl and n is zero, one or two;

and pharmaceutically acceptable salts, esters, and prodrugs thereof.

In one embodiment, the compounds of Formula Ie are represented by Formula Ie(i)

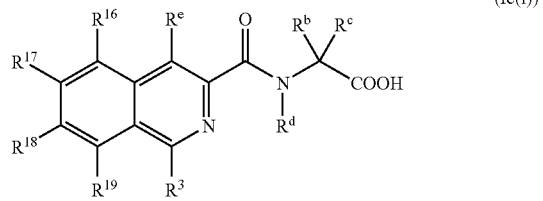

(Ie(i))

wherein $R^3$, $R^{16}$, $R^{17}$, $R^{18}$, $R^{19}$, $R^b$, $R^c$, $R^d$, and $R^e$ are as defined above in the discussion for Formula Ie; and pharmaceutically acceptable salts, esters, and prodrugs thereof.

In particular embodiments, the invention is directed to compounds of Formula Ie(i) wherein $R^3$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —XR$^{60}$ where X is oxygen, —S(O)$_n$— or —NR$^{70}$— where n is zero, one or two, R$^{60}$ is selected from the group consisting of alkyl, substituted alkyl, aryl, substituted aryl, heteroaryl, substituted heteroaryl, heterocyclic and substituted heterocyclic, and R$^{70}$ is hydrogen, alkyl or aryl;

$R^{17}$ and $R^{18}$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —XR$^{80}$ where X is oxygen, —S(O)$_n$— or —NR$^{90}$— where n is zero, one or two, R$^{80}$ is selected from the group consisting of alkyl, substituted alkyl, aryl, substituted aryl, heteroaryl, substituted heteroaryl, heterocyclic and substituted heterocyclic, and R$^{90}$ is hydrogen, alkyl or aryl;

$R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —XR$^{60}$ where X is oxygen, —S(O)$_n$— or —NR$^{70}$ where n is zero, one or two, R$^{60}$ is selected from the group consisting of alkyl, substituted alkyl, aryl, substituted aryl, heteroaryl, substituted heteroaryl, heterocyclic and substituted heterocyclic, and R$^{70}$ is hydrogen, alkyl or aryl;

$R^b$ is selected from the group consisting of hydrogen and methyl;

$R^c$ is selected from the group consisting of alkyl and substituted alkyl; or $R^a$ and $R^b$ may be joined to form a cycloalkyl, substituted cycloalkyl, heterocyclic or substituted heterocyclic; and $R^d$ is selected from the group consisting of hydrogen and alkyl or $R^d$ together with $R^c$ and the nitrogen pendent thereto forms a heterocyclic or substituted heterocyclic group; and $R^e$ is hydroxy;

and pharmaceutically acceptable salts, esters, and prodrugs thereof.

In another embodiment, the compounds of Formula Ie are represented by the Formula Ie(ii)

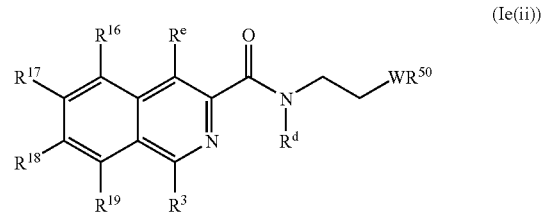

(Ie(ii))

wherein $R^3$, $R^{16}$, $R^{17}$, $R^{18}$, $R^{19}$, $R^d$, $R^e$, and WR$^{50}$ are as defined above in the discussion for Formula Ie; and pharmaceutically acceptable salts, esters, and prodrugs thereof.

In particular embodiments, the invention is directed to compounds of Formula Ie(ii) wherein W is selected from the group consisting of oxygen, —S(O)$_n$— and —NR$^{51}$— where n is zero, one or two, R$^{51}$ is selected from the group consisting of hydrogen, alkyl, substituted alkyl, acyl, aryl, substituted aryl, heteroaryl, substituted heteroaryl, heterocyclic and substituted heterocyclic;

$R^{50}$ is selected from the group consisting of hydrogen, alkyl, substituted alkyl, aryl, substituted aryl, heteroaryl, substituted heteroaryl, heterocyclic and substituted heterocyclic;

$R^d$ is selected from hydrogen and alkyl;

$R^e$ is hydroxy;

$R^{17}$ and $R^{18}$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —$XR^{80}$ where X is oxygen, —$S(O)_n$— or —$NR^{90}$— where n is zero, one or two, $R^{80}$ is selected from the group consisting of alkyl, substituted alkyl, aryl, substituted aryl, heteroaryl, substituted heteroaryl, heterocyclic and substituted heterocyclic, and $R^{90}$ is hydrogen, alkyl or aryl; and $R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —$XR^{60}$ where X is oxygen, —$S(O)_n$— or —$NR^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl or aryl;

and pharmaceutically acceptable salts, esters, and prodrugs thereof.

In another embodiment, the compounds of Formula Ie are represented by the Formula Ie(iii)

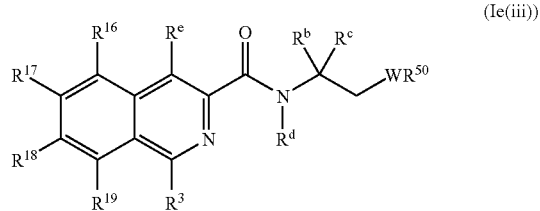

(Ie(iii))

wherein $R^3$, $R^{16}$, $R^{17}$, $R^{18}$, $R^{19}$, $R^b$, $R^c$, $R^d$, $R^e$, and $WR^{50}$ are as defined above in the discussion for Formula Ie; and pharmaceutically acceptable salts, esters, and prodrugs thereof.

In particular embodiments, the invention is directed to compounds of Formula Ie(iii) wherein W is selected from the group consisting of oxygen, —S(O)$_n$— and —$NR^{51}$— where n is zero, one or two, $R^{51}$ is selected from the group consisting of hydrogen, alkyl, substituted alkyl, aryl, substituted aryl, heteroaryl, substituted heteroaryl, heterocyclic and substituted heterocyclic;

$R^{50}$ is selected from the group consisting of hydrogen, alkyl, substituted alkyl, aryl, substituted aryl, heteroaryl, substituted heteroaryl, heterocyclic and substituted heterocyclic;

$R^3$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —$XR^{60}$ where X is oxygen, —$S(O)_n$— or —$NR^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl, or aryl;

$R^{17}$ and $R^{18}$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —$XR^{80}$ where X is oxygen, —$S(O)_n$— or —$NR^{90}$— where n is zero, one or two, $R^{80}$ is selected from the group consisting of alkyl, substituted alkyl, aryl, substituted aryl, heteroaryl, substituted heteroaryl, heterocyclic and substituted heterocyclic, and $R^{90}$ is hydrogen, alkyl, or aryl;

$R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —$XR^{60}$ where X is oxygen, —$S(O)_n$— or —$NR^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl, or aryl;

$R^b$ is selected from the group consisting of hydrogen and methyl;

$R^c$ is selected from the group consisting of alkyl and substituted alkyl; or $R^b$ and $R^c$ can be joined to form cycloalkyl, substituted cycloalkyl, heterocyclic or substituted heterocyclic $R^d$ is selected from the group consisting of hydrogen and alkyl or $R^d$ together with $R^c$ and the nitrogen pendent thereto forms a heterocyclic or substituted heterocyclic group; and $R^e$ is hydroxy;

and pharmaceutically acceptable salts, esters, and prodrugs thereof.

In another embodiment, the compounds of Formula Ie are represented by the Formula Ie(iv)

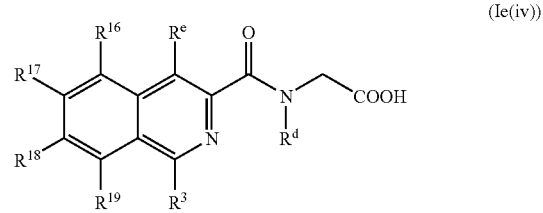

(Ie(iv))

wherein $R^3$, $R^{16}$, $R^{17}$, $R^{18}$, $R^{19}$, $R^d$, and $R^e$ are as defined above in the discussion for Formula Ie; and pharmaceutically acceptable salts, esters, and prodrugs thereof.

In one particular embodiment, the invention is directed to compounds of Formula Ie(iv) wherein $R^d$ is selected from hydrogen and alkyl;

$R^e$ is hydroxy;

$R^3$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —$XR^{60}$ where X is oxygen, —$S(O)_n$— or —$NR^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl or aryl;

$R^{17}$ and $R^{18}$ are independently selected from the group consisting of hydrogen, alkyl, substituted alkyl, aryl, substituted aryl, heteroaryl, substituted heteroaryl, halo, hydroxy, cyano, —$XR^{80}$ where X is oxygen, —$S(O)_n$— or —$NR^{90}$— where n is zero, one or two, $R^{80}$ is selected from the group consisting of alkyl, substituted alkyl, aryl, substituted aryl, heteroaryl, substituted heteroaryl, heterocyclic and substituted heterocyclic, and $R^{90}$ is hydrogen, alkyl or aryl; and $R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —$XR^{60}$ where X is oxygen, —$S(O)_n$— or —$NR^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl or aryl;

and pharmaceutically acceptable salts, esters, and prodrugs thereof.

In certain embodiments of compounds of Formula Ie including, but not limited to, certain compounds of Formulae Ie(i), Ie(ii), Ie(iii), and Ie(iv), $R^3$ is selected from the group consisting of hydrogen, alkyl, substituted alkyl, halo, alkoxy, aryloxy, substituted aryloxy, substituted aryl, alcylthio, aminoacyl, aryl, substituted amino, heteroaryl, heteroaryloxy, —$S(O)_n$-aryl, —$S(O)_n$-substituted aryl, —$S(O)_n$-heteroaryl, and —$S(O)_n$-substituted heteroaryl, where n is zero, one or two. In particular embodiments, $R^3$ is selected from the group consisting of (3-methoxyphenyl)sulfanyl; (4-chlorophenyl) sulfanyl; (4-methylphenyl)sulfanyl; 2-fluorophenoxy; 2-methoxyphenoxy; (2-methoxyphenyl)sulfanyl 3-fluorophenoxy; 3-methoxyphenoxy; 4-(methylcarbonylamino) phenoxy; 4-(methylsulfonamido)phenoxy; 4-fluorophenoxy; 4-methoxyphenoxy; 4-methoxyphenylsulfanyl; 4-methylphenyl; bromo; chloro; dimethylaminomethyl; ethoxy; ethylsulfanyl; hydrogen; isopropyl; methoxy; methoxymethyl; methyl; N,N-dimethylaminocarbonyl; naphth-2-yloxy; naphthylsulfanyl; phenoxy; phenyl; phenylamino; phenylsulfinyl; phenylsulfanyl; pyridin-2-yloxy; pyridin-2-yl; and pyridin-2-ylsulfanyl.

In certain embodiments of compounds of Formula Ie including, but not limited to, certain compounds of Formulae Ie(i), Ie(ii), Ie(iii), and Ie(iv), $R^{16}$ is hydrogen or phenyl.

In certain embodiments of compounds of Formula Ie including, but not limited to, certain compounds of Formulae Ie(i), Ie(ii), Ie(iii), and Ie(iv), $R^{17}$ is selected from the group consisting of: substituted aryloxy, substituted alkoxy, alkoxy, substituted alkyl, alkyl, amino, cycloalkyloxy, hydrogen, halo, aryl, —$S(O)_n$-aryl, —$S(O)_n$-substituted aryl, —$S(O)_n$-heteroaryl, and —$S(O)_n$-substituted heteroaryl, where n is zero, one or two, aminocarbonylamino, and heteroaryloxy. In particular embodiments, $R^{17}$ is selected from the group consisting of amino; (4-methyl)phenyl-sulfonylaminophenoxy; 3,4-difluorophenoxy; 3,5-difluorophenoxy; 3-fluoro-5-methoxy-phenoxy; 3-chloro-4-fluorophenoxy 4-$CF_3$—O-phenoxy; 4-$CF_3$-phenoxy; 4-chlorophenoxy; 4-fluorophenoxy; 4-(4-fluorophenoxy)phenoxy; 4-methoxyphenoxy; benzyloxy; bromo; butoxy; $CF_3$; chloro; cyclohexyloxy; hydrogen; iodo; isopropoxy; phenoxy; phenyl; phenylsulfanyl; phenylsulfonyl; phenylsulfinyl; phenylurea; pyridin-1-ylsulfanyl; pyridin-3-yloxy; and pyridin-4-ylsulfanyl.

In certain embodiments of compounds of Formula Ie including, but not limited to, certain compounds of Formulae Ie(i), Ie(ii), Ie(iii), and Ie(iv), $R^{18}$ is selected from the group consisting of substituted amino, aryloxy, substituted aryloxy, alkoxy, substituted alkoxy, halo, hydrogen, alkyl, substituted alkyl, aryl, —$S(O)_n$-aryl, —$S(O)_n$-substituted aryl, —$S(O)_n$-Cycloalkyl, where n is zero, one or two, aminocarbonylamino, heteroarylamino, and cycloalkyloxy. In particular embodiments, $R^{18}$ is selected from the group consisting of (4-methoxy)phenylsulfonylamino; 2,6-dimethylphenoxy; 3,4-difluorophenoxy; 3,5-difluorophenoxy; 3-chloro-4-fluorophenoxy; 3-methoxy-4-fluorophenoxy; 3-methoxy-5-fluorophenoxy; 4-(methylsulfonamido)phenoxy; 4-(phenylsulfonamido)phenoxy; 4-$CF_3$—O-phenoxy; 4-$CF_3$-phenoxy; 4-chlorophenoxy; 4-fluorophenoxy; 4-(4-fluorophenoxy) phenoxy; 4-methoxyphenoxy; 4-nitrophenoxy; benzyloxy; bromo; butoxy; $CF_3$; chloro; cyclohexyloxy; cyclohexylsulfanyl; cyclohexylsulfonyl; fluoro; hydrogen; iodo; isopropoxy; methyl; phenoxy; phenyl; phenylsulfanyl; phenylsulfinyl; phenylsulfonyl; phenylurea; pyridin-1-ylsulfanyl; pyridin-3-yloxy; and pyridin-4-ylsulfanyl.

Alternatively, $R^{17}$ and $R^{18}$, combined with the carbon atoms pendent thereto, are joined to form an aryl group. In a particular embodiment, the aryl group is phenyl.

In certain embodiments of compounds of Formula Ie including, but not limited to, certain compounds of Formulae Ie(i), Ie(ii), Ie(iii), and Ie(iv), $R^{19}$ is selected from the group consisting of: substituted arylthio, halo, hydrogen, substituted alkyl and aryl. In particular embodiments, $R^{19}$ is selected from the group consisting of 4-chlorophenyl sulfanyl; chloro; hydrogen; methoxymethyl; and phenyl.

In certain embodiments of compounds of Formulae Ie, including but not limited to, certain compounds of Formulae Ie(i) and Ie(iii), $R^b$ is selected from the group consisting of hydrogen, deuterium, aryl and alkyl. In particular embodiments, $R^b$ is selected from the group consisting of phenyl, hydrogen, deuterium and methyl.

In certain embodiments of compounds of Formula Ie including, but not limited to, certain compounds of Formulae Ie(i) and Ie(iii), $R^c$ is selected from the group consisting of preferably hydrogen, deuterium, alkyl, substituted alkyl, and substituted amino. In particular embodiments, $R^c$ is selected from the group consisting of 4-aminobutyl; 4-hydroxybenzyl; benzyl; carboxylmethyl; deuterium; hydroxymethyl; imidazol-4-ylmethyl; isopropyl; methyl; and propyl.

Alternatively, $R^b$, $R^c$, and the carbon atom pendent thereto join to form a cycloalkyl and more preferably cyclopropyl.

In certain embodiments of compounds of Formula Ie including, but not limited to, certain compounds of Formulae Ie(i) and Ie(iii), $R^d$ is hydrogen, alkyl or substituted alkyl. In particular embodiments, $R^d$ is hydrogen, methyl or carboxylmethyl (—$CH_2C(O)OH$). Alternatively, $R^c$, $R^d$, and the carbon atom and nitrogen atom respectively pendent thereto join to form a heterocyclic group and more preferably pyrrolidinyl.

In certain embodiments of compounds of Formula Ie including, but not limited to, certain compounds of Formulae Ie(i), Ie(ii), Ie(iii) and Ie(iv), $R^e$ is selected from the group consisting of hydrogen, hydroxy, alkoxy, substituted alkoxy, cycloalkoxy, substituted cycloalkoxy, thiol, acyloxy and aryl. In particular embodiments, $R^e$ is selected from the group consisting of hydroxy; benzyloxy; ethoxy; thiol; methoxy; methylcarbonyloxy; and phenyl.

In certain embodiments of compounds of Formulae Ie including, but not limited to, certain compounds of Formulae Ie(ii) and Ie(iii), $WR^{50}$ is selected from the group consisting of amino, substituted amino, aminoacyl, hydroxy, and alkoxy. In particular embodiments, $WR^{50}$ is selected from the group consisting of amino; dimethylamino; hydroxy; methoxy; and methylcarbonylamino.

Isoquinoline-3-carboxamides of Formula Ib and Formula Ie include, but are not limited to, N-((1-chloro-4-hydroxy-7-(2-propyloxy) isoquinolin-3-yl)-carbonyl)-glycine, N-((1-chloro-4-hydroxy-6-(2-propyloxy) isoquinolin-3-yl)-carbonyl)-glycine, N-((1-chloro-4-hydroxy-isoquinoline-3-carbonyl)-amino)-acetic acid (Compound A), [[(1-chloro-4-hydroxy-7-methoxy-isoquinoline-3-carbonyl)-amino]- acetic acid] (Compound I), N-((1-chloro-4-hydroxy-6-methoxyisoquinolin-3-yl)-carbonyl)-glycine, N-((7-butyloxy)-1-chloro-4-hydroxyisoquinolin-3-yl)-carbonyl)-glycine, N-((6-benzyloxy-1-chloro-4-hydroxy-isoquinoline-3-carbonyl)-amino)-acetic acid, ((7-benzyloxy-1-chloro-4-hydroxy-isoquinoline-3-carbonyl)-amino)-acetic acid methyl ester, N-((7-benzyloxy-1-chloro-4-hydroxy-isoquinoline-3-carbonyl)-amino)-acetic acid, N-((8-chloro-4-hydroxyisoquinolin-3-yl)-carbonyl)-glycine, N-((7-butoxy-4-hydroxy-isoquinoline-3-carbonyl)-amino)-acetic acid (M), [(1,7-dichloro-4-hydroxy-isoquinoline-3-carbonyl)-amino]-acetic acid, [[(6,7-dichloro-4-hydroxy-isoquinoline-3-carbonyl)-amino]-acetic acid] (compound J), {[4-hydroxy-1-(naphthalen-2-yloxy)-isoquinoline-3-carbonyl]-amino}-acetic acid, {[4-hydroxy-1-(4-methoxy-phenoxy)-isoquinoline-3-carbonyl]-amino}-acetic acid, {[4-hydroxy-1-(3-methoxy-phenoxy)-isoquinoline-3-carbonyl]-amino}-acetic acid, {[1-(3-fluoro-phenoxy)-4-hydroxy-isoquinoline-3-carbonyl]-amino}-acetic acid, {[1-(4-fluoro-phenoxy)-4-hydroxy-isoquinoline-3-carbonyl]-amino}-acetic acid, {[1-(2-fluoro-phenoxy)-4-hydroxy-isoquinoline-3-carbonyl]-amino}-acetic acid, {[4-hydroxy-1-(2-methoxy-phenoxy)-isoquinoline-3-carbonyl]-amino}-acetic acid, [(4-hydroxy-1-phenylamino-isoquinoline-3-carbonyl)-amino]-acetic acid, [(1-chloro-4-methoxy-isoquinoline-3-carbonyl)-amino]-acetic acid, [(1-chloro-4-ethoxy-isoquinoline-3-carbonyl)-amino]-acetic acid, [(4-hydroxy-1-methoxy-isoquinoline-3-carbonyl)-amino]-acetic acid, [(1-ethoxy-4-hydroxy-isoquinoline-3-carbonyl)-amino]-acetic acid, [(4-hydroxy-1-phenyl-isoquinoline-3-carbonyl)-amino]-acetic acid, [(4-hydroxy-1-methyl-isoquinoline-3-carbonyl)-amino]-acetic acid, [(4-hydroxy-1-methoxymethyl-isoquinoline-3-carbonyl)-amino]-acetic acid, [(1-dimethylcarbamoyl-4-hydroxy-isoquinoline-3-carbonyl)-amino]-acetic acid, [(4-hydroxy-1-methyl-6-phenoxy-isoquinoline-3-carbonyl)-amino]-acetic acid, [(4-hydroxy-1-methyl-7-phenoxy-isoquinoline-3-carbonyl)-amino]-acetic acid (Compound D), [(4-benzyloxy-1-methyl-7-phenoxy-isoquinoline-3-carbonyl)-amino]-acetic acid, [(4-ethoxy-1-methyl-7-phenoxy-isoquinoline-3-carbonyl)-amino]-acetic acid, [(1-dimethylcarbamoyl-4-hydroxy-7-phenoxy-isoquinoline-3-carbonyl)-amino]-acetic acid, [(4-hydroxy-1-methoxymethyl-7-phenoxy-isoquinoline-3-carbonyl)-amino]-acetic acid, [(4-hydroxy-1-p-tolyl-isoquinoline-3-carbonyl)-amino]-acetic acid, {[7-(4-fluoro-phenoxy)-4-hydroxy-1-methyl-isoquinoline-3-carbonyl]-amino}-acetic acid, {[1-chloro-4-hydroxy-7-(4-methoxy-phenoxy)-isoquinoline-3-carbonyl]-amino}-acetic acid, {[4-hydroxy-7-(4-methoxy-phenoxy)-isoquinoline-3-carbonyl]-amino}-acetic acid (Compound C), {[1-chloro-4-hydroxy-6-(4-methoxy-phenoxy)-isoquinoline-3-carbonyl]-amino}-acetic acid, {[4-hydroxy-6-(4-methoxy-phenoxy)-isoquinoline-3-carbonyl]-amino}-acetic acid, {[1-chloro-4-hydroxy-7-(4-trifluoromethyl-phenoxy)-isoquinoline-3-carbonyl]-amino}-acetic acid, {[4-hydroxy-7-(4-trifluoromethyl-phenoxy)-isoquinoline-3-carbonyl]-amino}-acetic acid, {[1-chloro-4-hydroxy-6-(4-trifluoromethyl-phenoxy)-isoquinoline-3-carbonyl]-amino}-acetic acid, {[4-hydroxy-6-(4-trifluoromethyl-phenoxy)-isoquinoline-3-carbonyl]-amino}-acetic acid, {[1-chloro-7-(4-fluoro-phenoxy)-4-hydroxy-isoquinoline-3-carbonyl]-amino}-acetic acid, {[7-(4-fluoro-phenoxy)-4-hydroxy-isoquinoline-3-carbonyl]-amino}-acetic acid (Compound E), {[1-chloro-6-(4-fluoro-phenoxy)-4-hydroxy-isoquinoline-3-carbonyl]-amino}-acetic acid, {[6-(4-fluoro-phenoxy)-4-hydroxy-isoquinoline-3-carbonyl]-amino}-acetic acid, [(7-benzenesulfinyl-4-hydroxy-isoquinoline-3-carbonyl)-amino]-acetic acid, [(7-benzenesulfonyl-4-hydroxy-isoquinoline-3-carbonyl)-amino]-acetic acid, [(6-benzenesulfinyl-4-hydroxy-isoquinoline-3-carbonyl)-amino]-acetic acid, [(6-benzenesulfonyl-4-hydroxy-isoquinoline-3-carbonyl)-amino]-acetic acid, {[4-hydroxy-7-(4-methoxy-benzenesulfonylamino)-isoquinoline-3-carbonyl]-amino}-acetic acid, [(4-hydroxy-1-phenylsulfanyl-isoquinoline-3-carbonyl)-amino]-acetic acid, {[1-(4-chloro-phenylsulfanyl)-4-hydroxy-isoquinoline-3-carbonyl]-amino}-acetic acid, [(4-hydroxy-1-p-tolylsulfanyl-isoquinoline-3-carbonyl)-amino]-acetic acid, {[4-hydroxy-1-(3-methoxy-phenylsulfanyl)-isoquinoline-3-carbonyl]-amino}-acetic acid, {[4-hydroxy-1-(2-methoxy-phenylsulfanyl)-isoquinoline-3-carbonyl]-amino}-acetic acid, {[4-hydroxy-1-(naphthalen-2-ylsulfanyl)-isoquinoline-3-carbonyl]-amino}-acetic acid, [(1-benzenesulfinyl-4-hydroxy-isoquinoline-3-carbonyl)-amino]-acetic acid, [(1-benzenesulfonyl-4-hydroxy-isoquinoline-3-carbonyl)-amino]-acetic acid, [(1-chloro-4-hydroxy-6,7-diphenoxy-isoquinoline-3-carbonyl)-amino]-acetic acid, [[(4-Hydroxy-1,7-diphenoxy-isoquinoline-3-carbonyl)-amino]-acetic acid] (Compound M), [(4-hydroxy-6,7-diphenoxy-isoquinoline-3-carbonyl)-amino]-acetic acid, {[4-hydroxy-7-(4-nitro-phenoxy)-isoquinoline-3-carbonyl]-amino}-acetic acid, [(4-mercapto-7-phenoxy-isoquinoline-3-carbonyl)-amino]-acetic acid, [(4-mercapto-7-trifluoromethyl-isoquinoline-3-carbonyl)-amino]-acetic acid, {[7-(4-chloro-phenoxy)-4-hydroxy-isoquinoline-3-carbonyl]-amino}-acetic acid, {[6-(4-chloro-phenoxy)-4-hydroxy-isoquinoline-3-carbonyl]-amino}-acetic acid, {[6-(3-fluoro-5-methoxy-phenoxy)-4-hydroxy-isoquinoline-3-carbonyl]-amino}-acetic acid, {[7-(3-fluoro-5-methoxy-phenoxy)-4-hydroxy-isoquinoline-3-carbonyl]-amino}-acetic acid, {[7-(3,4-difluoro-phenoxy)-4-hydroxy-isoquinoline-3-carbonyl]-amino}-acetic acid, {[6-(3,4-difluoro-phenoxy)-4-hydroxy-isoquinoline-3-carbonyl]-amino}-acetic acid, {[4-hydroxy-7-(4-trifluoromethoxy-phenoxy)-isoquinoline-3-carbonyl]-amino}-acetic acid, {[4-hydroxy-6-(4-trifluoromethoxy-phenoxy)-isoquinoline-3-carbonyl]-amino}-acetic acid, 2-(S)-{[7-(4-chloro-phenoxy)-4-hydroxy-isoquinoline-3-carbonyl]-amino}-propionic acid, 2-(S)-{[6-(4-chloro-phenoxy)-4-hydroxy-isoquinoline-3-carbonyl]-amino}-propionic acid, 2-{[7-(3,4-difluoro-phenoxy)-4-hydroxy-isoquinoline-3-carbonyl]-amino}-propionic acid, 2-(S)-[(4-hydroxy-7-phenylsulfanyl-isoquinoline-3-carbonyl)-amino]-propionic acid (Compound L), 2-(R)-[(4-hydroxy-7-phenylsulfanyl-isoquinoline-3-carbonyl)-amino]-propionic acid, 2-(R)-[(4-hydroxy-7-phenoxy-isoquinoline-3-carbonyl)-amino]-propionic acid, (S)-2-[(4-Hydroxy-7-phenoxy-isoquinoline-3-carbonyl)-amino]-propionic acid (Compound B), 2-(S)-{[4-hydroxy-7-(4-methoxy-phenoxy)-isoquinoline-3-carbonyl]-amino}-propionic acid, 2-(S)-[(7-benzenesulfonyl-4-hydroxy-isoquinoline-3-carbonyl)-amino]-propionic acid, (R)-2-[(4-hydroxy-1-methoxymethyl-7-phenoxy-isoquinoline-3-carbonyl)-amino]-propionic acid, (S)-2-[(4-hydroxy-1-methoxymethyl-7-phenoxy-isoquinoline-3-carbonyl)-amino]-propionic acid, (S)-2-[(4-mercapto-7-phenoxy-isoquinoline-3-carbonyl)-amino]-propionic acid, (S)-2-{[1-(4-chloro-phenylsulfanyl)-4-hydroxy-isoquinoline-3-carbonyl]-amino}-propionic acid, (R)-2-{[1-(4-chloro-phenylsulfanyl)-4-hydroxy-isoquinoline-3-carbonyl]-amino}-propionic acid, [(4-hydroxy-7-phenylsulfanyl-isoquinoline-3-carbonyl)-amino]-acetic acid (Compound N), [(4-hydroxy-6-phenylsulfanyl-isoquinoline-3-carbonyl)-amino]-acetic acid, [(1-chloro-4-hydroxy-7-phenylsulfanyl-isoquinoline-3-carbonyl)-amino]-acetic acid, [(1-chloro-4- hydroxy-6-phenylsulfanyl-isoquinoline-3-carbonyl)-amino]-acetic acid, [(1-bromo-4-hydroxy-7-phenylsulfanyl-isoquinoline-3-carbonyl)-amino]-acetic acid, [(1-bromo-4-hydroxy-6-phenylsulfanyl-isoquinoline-3-carbonyl)-amino]-acetic acid, [(4-hydroxy-7-phenoxy-isoquinoline-3-carbonyl)-amino]-acetic acid (Compound K), [(4-hydroxy-6-phenoxy-isoquinoline-3-carbonyl)-amino]-acetic acid, [(1-chloro-4-hydroxy-7-phenoxy-isoquinoline-3-carbonyl)-amino]-acetic acid, [(1-chloro-4-hydroxy-6-phenoxy-isoquinoline-3-carbonyl)-amino]-acetic acid, [(1-bromo-4-hydroxy-7-phenoxy-isoquinoline-3-carbonyl)-amino]-acetic acid, [(1-bromo-4-hydroxy-6-phenoxy-isoquinoline-3-carbonyl)-amino]-acetic acid, {[7-(2,6-dimethyl-phenoxy)-4-hydroxy-isoquinoline-3-carbonyl]-amino}-acetic acid, {[1-chloro-7-(2,6-dimethyl-phenoxy)-4-hydroxy-isoquinoline-3-carbonyl]-amino}-acetic acid, {[1-bromo-7-(2,6-dimethyl-phenoxy)-4-hydroxy-isoquinoline-3-carbonyl]-amino}-acetic acid, [(1-bromo-7-chloro-4-hydroxy-isoquinoline-3-carbonyl)-amino]-acetic acid, [(1-bromo-6-chloro-4-hydroxy-isoquinoline-3-carbonyl)-amino]-acetic acid, [(1-bromo-4-hydroxy-7-trifluoromethyl-isoquinoline-3-carbonyl)-amino]-acetic acid, [(1-bromo-4-hydroxy-6-trifluoromethyl-isoquinoline-3-carbonyl)-amino]-acetic acid, [(4-hydroxy-1-phenoxy-isoquinoline-3-carbonyl)-amino]-acetic acid, [(1,7-dibromo-4-hydroxy-isoquinoline-3-carbonyl)-amino]-acetic acid, [(7-bromo-1-chloro-4-hydroxy-isoquinoline-3-carbonyl)-amino]-acetic acid, [(6-bromo-4-hydroxy-isoquinoline-3-carbonyl)-amino]-acetic acid, [(1-bromo-7-fluoro-4-hydroxy-isoquinoline-3-carbonyl)-amino]-acetic acid, [(7-fluoro-4-hydroxy-isoquinoline-3-carbonyl)-amino]-acetic acid, [(1-chloro-7-fluoro-4-hydroxy-isoquinoline-3-carbonyl)-amino]-acetic acid, [(1-bromo-4-hydroxy-isoquinoline-3-carbonyl)-amino]-acetic acid, [(4-hydroxy-6-phenyl-isoquinoline-3-carbonyl)-amino]-acetic acid, [(4-hydroxy-7-phenyl-isoquinoline-3-carbonyl)-amino]-acetic acid, [(1-chloro-4-hydroxy-6-phenyl-isoquinoline-3-carbonyl)-amino]-acetic acid, [(1-chloro-4-hydroxy-7-phenyl-isoquinoline-3-carbonyl)-amino]-acetic acid, [(1-bromo-4-hydroxy-6-phenyl-isoquinoline-3-carbonyl)-amino]-acetic acid, [(1-bromo-4-hydroxy-7-phenyl-isoquinoline-3-carbonyl)-amino]-acetic acid, [(4-hydroxy-5-phenyl-isoquinoline-3-carbonyl)-amino]-acetic acid, [(4-hydroxy-8-phenyl-isoquinoline-3-carbonyl)-amino]-acetic acid, [(1-chloro-4-hydroxy-5-phenyl-isoquinoline-3-carbonyl)-amino]-acetic acid, [(1-chloro-4-hydroxy-8-phenyl-isoquinoline-3-carbonyl)-amino]-acetic acid, [(1-bromo-4-hydroxy-5-phenyl-isoquinoline-3-carbonyl)-amino]-acetic acid, [(1-bromo-4-hydroxy-8-phenyl-isoquinoline-3-carbonyl)-amino]-acetic acid, [(1-ethylsulfanyl-4-hydroxy-isoquinoline-3-carbonyl)-amino]-acetic acid, {[4-hydroxy-1-(4-methoxy-phenylsulfanyl)-isoquinoline-3-carbonyl]-amino}-acetic acid, [(1-chloro-4-hydroxy-7-iodo-isoquinoline-3-carbonyl)-amino]-acetic acid, [(1-chloro-4-hydroxy-6-iodo-isoquinoline-3-carbonyl)-amino]-acetic acid, [(4-hydroxy-7-iodo-isoquinoline-3-carbonyl)-amino]-acetic acid, [(1-bromo-4-hydroxy-7-methyl-isoquinoline-3-carbonyl)-amino]-acetic acid, [(1-bromo-7-butoxy-4-hydroxy-isoquinoline-3-carbonyl)-amino]-acetic acid, [(1-bromo-6-butoxy-4-hydroxy-isoquinoline-3-carbonyl)-amino]-acetic acid, [carboxymethyl-(1-chloro-4-hydroxy-isoquinoline-3-carbonyl)-amino]-acetic acid; [carboxymethyl-(1-chloro-4-hydroxy-6-isopropoxy-isoquinoline-3-carbonyl)-amino]-acetic acid; 1-chloro-4-hydroxy-isoquinoline-3-carboxylic acid (2-amino-ethyl)-amide (trifluoro-acetic acid salt); 1-chloro-4-hydroxy-isoquinoline-3-carboxylic acid (2-methoxy-ethyl)-amide; 1-chloro-4-hydroxy-isoquinoline-3-carboxylic acid (2-hydroxy-ethyl)-amide; 1-chloro-4-hydroxy-isoquinoline-3-carboxylic acid (2-dimethylamino-ethyl)-amide; 1-chloro-4-hydroxy-isoquinoline-3-carboxylic acid (2-acetylamino-ethyl)-amide; 1-chloro-4-hydroxy-6-isopropoxy-isoquinoline-3-carboxylic acid (2-hydroxy-ethyl)-amide; 1-chloro-4-hydroxy-6-isopropoxy-isoquinoline-3-carboxylic acid (2-methoxy-ethyl)-amide; 1-chloro-4-hydroxy-6-isopropoxy-isoquinoline-3-carboxylic acid (2-amino-ethyl)-amide (trifluoro-acetic acid salt); 1-chloro-4-hydroxy-6-isopropoxy-isoquinoline-3-carboxylic acid (2-dimethylamino-ethyl)-amide; 1-chloro-4-hydroxy-7-isopropoxy-isoquinoline-3-carboxylic acid (2-amino-ethyl)-amide (trifluoro-acetic acid salt); 1-chloro-4-hydroxy-7-isopropoxy-isoquinoline-3-carboxylic acid (2-methoxy-ethyl)-amide; 1-chloro-4-hydroxy-7-isopropoxy-isoquinoline-3-carboxylic acid (2-dimethylamino-ethyl)-amide; 1-chloro-4-hydroxy-7-isopropoxy-isoquinoline-3-carboxylic acid (2-hydroxy-ethyl)-amide; (R)-2-[(1-chloro-4-hydroxy-isoquinoline-3-carbonyl)-amino]-3-hydroxy-propionic acid, (S)-2-[(1-chloro-4-hydroxy-isoquinoline-3-carbonyl)-amino]-3-hydroxy-propionic acid, (R)-2-[(1-chloro-4-hydroxy-6-isopropoxy-isoquinoline-3-carbonyl)-amino]-3-hydroxy-propionic acid, (S)-2-[(1-chloro-4-hydroxy-6-isopropoxy-isoquinoline-3-carbonyl)-amino]-3-hydroxy-propionic acid, (R)-2-[(1-chloro-4-hydroxy-7-isopropoxy-isoquinoline-3-carbonyl)-amino]-3-hydroxy-propionic acid, (S)-2-[(1-chloro-4-hydroxy-7-isopropoxy-isoquinoline-3-carbonyl)-amino]-3-hydroxy-propionic acid, 2-[(1-chloro-4-hydroxy-isoquinoline-3-carbonyl)-amino]-2-methyl-propionic acid, 2-[(1-chloro-4-hydroxy-6-isopropoxy-isoquinoline-3-carbonyl)-amino]-2-methyl-propionic acid, (R)-2-[(1-chloro-4-hydroxy-isoquinoline-3-carbonyl)-amino]-3-(1h-imidazol-4-yl)-propionic acid (trifluoro-acetic acid salt), (S)-2-[(1-chloro-4-hydroxy-isoquinoline-3-carbonyl)-amino]-3-(1h-imidazol-4-yl)-propionic acid (trifluoro-acetic acid salt), (R)-2-[(1-chloro-4-hydroxy-isoquinoline-3-carbonyl)-amino]-3-methyl-butyric acid, (S)-2-[(1-chloro-4-hydroxy-isoquinoline-3-carbonyl)-amino]-3-methyl-butyric acid, (R)-2-[(1-chloro-4-hydroxy-6-isopropoxy-isoquinoline-3-carbonyl)-amino]-3-methyl-butyric acid, (S)-2-[(1-chloro-4-hydroxy-6-isopropoxy-isoquinoline-3-carbonyl)-amino]-3-methyl-butyric acid, (R)-2-[(1-chloro-4-hydroxy-7-isopropoxy-isoquinoline-3-carbonyl)-amino]-3-methyl-butyric acid, (S)-2-[(1-chloro-4-hydroxy-7-isopropoxy-isoquinoline-3-carbonyl)-amino]-3-methyl-butyric acid, (S)-2-[(6-benzyloxy-1-chloro-4-hydroxy-isoquinoline-3-carbonyl)-amino]-3-methyl-butyric acid, (R)-2-[(1-chloro-4-hydroxy-isoquinoline-3-carbonyl)-amino]-3-phenyl-propionic acid, (S)-2-[(1-chloro-4-hydroxy-isoquinoline-3-carbonyl)-amino]-3-phenyl-propionic acid, (R)-2-[(1-chloro-4-hydroxy-6-isopropoxy-isoquinoline-3-carbonyl)-amino]-3-phenyl-propionic acid, (S)-2-[(1-chloro-4-hydroxy-6-isopropoxy-isoquinoline-3-carbonyl)-amino]-3-phenyl-propionic acid, (R)-2-[(1-chloro-4-hydroxy-7-isopropoxy-isoquinoline-3-carbonyl)-amino]-3-phenyl-propionic acid, (S)-2-[(1-chloro-4-hydroxy-7-isopropoxy-isoquinoline-3-carbonyl)-amino]-3-phenyl-propionic acid, (R)-2-[(1-chloro-4-hydroxy-isoquinoline-3-carbonyl)-amino]-3-(4-hydroxy-phenyl)-propionic acid, (S)-2-[(1-chloro-4-hydroxy-isoquinoline-3-carbonyl)-amino]-3-(4-hydroxy-phenyl)-propionic acid, (R)-2-[(1-chloro-4-hydroxy-6-isopropoxy-isoquinoline-3-carbonyl)-amino]-3-(4-hydroxy-phenyl)-propionic acid, (S)-2-[(1-chloro-4-hydroxy-6-isopropoxy-isoquinoline-3-carbonyl)-amino]-3-(4-hydroxy-phenyl)-propionic acid, (R)-2-[(1-chloro-4-hydroxy-7-isopropoxy-isoquinoline-3-carbonyl)-amino]-3-(4-hydroxy-phenyl)-propionic acid, (S)-2-[(1-chloro-4- hydroxy-7-isopropoxy-isoquinoline-3-carbonyl)-amino]-3-(4-hydroxy-phenyl)-propionic acid, (R)-2-[(1-chloro-4-hydroxy-6-isopropoxy-isoquinoline-3-carbonyl)-amino]-pentanoic acid, (S)-2-[(1-chloro-4-hydroxy-6-isopropoxy-isoquinoline-3-carbonyl)-amino]-pentanoic acid, (R)-1-(1-chloro-4-hydroxy-isoquinoline-3-carbonyl)-pyrrolidine-2-carboxylic acid, (S)-1-(1-chloro-4-hydroxy-isoquinoline-3-carbonyl)-pyrrolidine-2-carboxylic acid, (R)-1-(1-chloro-4-hydroxy-6-isopropoxy-isoquinoline-3-carbonyl)-pyrrolidine-2-carboxylic acid, (S)-1-(1-chloro-4-hydroxy-6-isopropoxy-isoquinoline-3-carbonyl)-pyrrolidine-2-carboxylic acid, (R)-6-amino-2-[(1-chloro-4-hydroxy-isoquinoline-3-carbonyl)-amino]-hexanoic acid (trifluoro-acetic acid salt), (S)-6-amino-2-[(1-chloro-4-hydroxy-isoquinoline-3-carbonyl)-amino]-hexanoic acid (trifluoro-acetic acid salt), (R)-6-amino-2-[(1-chloro-4-hydroxy-6-isopropoxy-isoquinoline-3-carbonyl)-amino]-hexanoic acid, trifluoroacetic acid salt, (S)-6-amino-2-[(1-chloro-4-hydroxy-6-isopropoxy-isoquinoline-3-carbonyl)-amino]-hexanoic acid (trifluoro-acetic acid salt), (R)-6-amino-2-[(1-chloro-4-hydroxy-7-isopropoxy-isoquinoline-3-carbonyl)-amino]-hexanoic acid, trifluoroacetic acid salt, (S)-6-amino-2-[(1-chloro-4-hydroxy-7-isopropoxy-isoquinoline-3-carbonyl)-amino]-hexanoic acid (trifluoro-acetic acid salt), (R)-2-[(1-chloro-4-hydroxy-isoquinoline-3-carbonyl)-amino]-succinic acid, (S)-2-[(1-chloro-4-hydroxy-isoquinoline-3-carbonyl)-amino]-succinic acid, (R)-2-[(1-chloro-4-hydroxy-6-isopropoxy-isoquinoline-3-carbonyl)-amino]-succinic acid, (S)-2-[(1-chloro-4-hydroxy-6-isopropoxy-isoquinoline-3-carbonyl)-amino]-succinic acid, (R)-2-[(1-chloro-4-hydroxy-7-isopropoxy-isoquinoline-3-carbonyl)-amino]-succinic acid, (R)-2-[(6-benzyloxy-1-chloro-4-hydroxy-isoquinoline-3-carbonyl)-amino]-propionic acid, (S)-2-[(7-benzyloxy-1-chloro-4-hydroxy-isoquinoline-3-carbonyl)-amino]-propionic acid, (R)-2-[(7-benzyloxy-1-chloro-4-hydroxy-isoquinoline-3-carbonyl)-amino]-propionic acid, (S)-2-[(1-chloro-4-hydroxy-isoquinoline-3-carbonyl)-amino]-propionic acid, (R)-2-[(1-chloro-4-hydroxy-isoquinoline-3-carbonyl)-amino]-propionic acid, (S)-2-[(6-isopropoxy-1-chloro-4-hydroxy-isoquinoline-3-carbonyl)-amino]-propionic acid, (R)-2-[6-isopropoxy-1-chloro-4-hydroxy-isoquinoline-3-carbonyl)-amino]-propionic acid, (S)-2-[(7-isopropoxy-1-chloro-4-hydroxy-isoquinoline-3-carbonyl)-amino-propionic acid, (R)-2-[(7-isopropoxy-1-chloro-4-hydroxy-isoquinoline-3-carbonyl)-amino]propionic acid, {[7-(3,5-difluoro-phenoxy)-4-hydroxy-isoquinoline-3-carbonyl]-amino}-acetic acid, {[6-(3,5-difluoro-phenoxy)-4-hydroxy-isoquinoline-3-carbonyl]-amino}-acetic acid, ({7-[4-(4-fluoro-phenoxy)-phenoxy]4-hydroxy-isoquinoline-3-carbonyl}-amino)-acetic acid, ({6-[4-(4-fluoro-phenoxy)-phenoxy]4-hydroxy-isoquinoline-3-carbonyl}-amino)-acetic acid, {[7-(3-chloro-4-fluoro-phenoxy)-4-hydroxy-isoquinoline-3-carbonyl]-amino}-acetic acid, {[6-(3-chloro-4-fluoro-phenoxy)-4-hydroxy-isoquinoline-3-carbonyl]-amino}-acetic acid, (S)-2-{[7-(3-fluoro-5-methoxy-phenoxy)-4-hydroxy-isoquinoline-3-carbonyl]-amino}-propionic acid, 2-(S)-[(7-cyclohexyloxy-4-hydroxy-isoquinoline-3-carbonyl)-amino]-propionic acid, 2-(S)-{[7-(4-fluoro-phenoxy)-4-hydroxy-1-methyl-isoquinoline-3-carbonyl]-amino}-propionic acid, 2-(S)-{[7-(4-fluoro-phenoxy)-4-hydroxy-isoquinoline-3-carbonyl]-amino}-propionic acid, 2-(S)-[(4-hydroxy-1-methyl-7-phenoxy-isoquinoline-3-carbonyl)-amino]-propionic acid, 2-(S)-[(4-hydroxy-1-methyl-7-phenylsulfanyl-isoquinoline-3-carbonyl)-amino]-propionic acid, 2-(S)-{[4-hydroxy-7-(4-trifluoromethyl-phenoxy)-isoquinoline-3-carbonyl]-amino}-propionic acid, {[7-(4-chloro-phenoxy)-4-hydroxy-1-methyl-isoquinoline-3-carbonyl]-amino}-acetic acid, {[6-(4-chloro-phenoxy)-4-hydroxy-1-methyl-isoquinoline-3-carbonyl]-amino}-acetic acid, {[7-(3,5-difluoro-phenoxy)-4-hydroxy-1-methyl-isoquinoline-3-carbonyl]-amino}-acetic acid, {[4-hydroxy-7-(4-methoxy-phenoxy)-1-methyl-isoquinoline-3-carbonyl]-amino}-acetic acid, {[4-hydroxy-6-(4-methoxy-phenoxy)-1-methyl-isoquinoline-3-carbonyl]-amino}-acetic acid, [(6-cyclohexyloxy-4-hydroxy-isoquinoline-3-carbonyl)-amino]-acetic acid, [(7-cyclohexyloxy-4-hydroxy-isoquinoline-3-carbonyl)-amino]-acetic acid, [(7-cyclohexyloxy-4-hydroxy-1-methyl-isoquinoline-3-carbonyl)-amino]-acetic acid, [(7-cyclohexylsulfanyl-4-hydroxy-isoquinoline-3-carbonyl)-amino]-acetic acid, [(7-cyclohexanesulfonyl-4-hydroxy-isoquinoline-3-carbonyl)-amino]-acetic acid, [(4-hydroxy-1-isobutyl-isoquinoline-3-carbonyl)-amino]-acetic acid, [(1-ethyl-4-hydroxy-7-phenoxy-isoquinoline-3-carbonyl)-amino]-acetic acid, [(1-dimethylaminomethyl-4-hydroxy-7-phenylsulfanyl-isoquinoline-3-carbonyl)-amino]-acetic acid, [(4-hydroxy-1-methyl-7-phenylsulfanyl-isoquinoline-3-carbonyl)-amino]-acetic acid, {[4-hydroxy-1-methyl-7-(4-trifluoromethyl-phenoxy)-isoquinoline-3-carbonyl]-amino}-acetic acid.

In certain aspects, compounds of the present invention include 4-oxo-[1,10]-phenanthrolines. Exemplary 4-oxo-[1, 10]-phenanthrolines are disclosed in, e.g., International Publication No. WO 03/049686 and International Publication No. WO 03/053997, and include compounds of Formula II

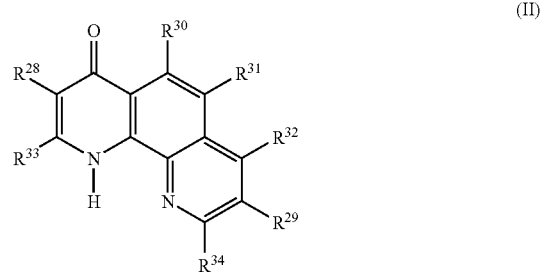

(II)

where $R^{28}$ is hydrogen, nitro, amino, cyano, halogen, $(C_1-C_4)$-alkyl, carboxy or a metabolically labile ester derivative thereof, $(C_1-C_4)$-alkylamino, di-$(C_1-C_4)$-alkylamino, $(C_1-C_6)$-alkoxycarbonyl, $(C_2-C_4)$-alkanoyl, hydroxy-$(C_1-C_4)$-alkyl, carbamoyl, N—$(C_1-C_4)$-alkylcarbamoyl, $(C_1-C_4)$-alkylthio, $(C_1-C_4)$-alkylsulfinyl, $(C_1-C_4)$-alkylsulfonyl, phenylthio, phenylsulfinyl, phenylsulfonyl, said phenyl or phenyl groups being optionally substituted with 1 to 4 identical or different halogen, $(C_1-C_4)$-alkyoxy, $(C_1-C_4)$-alkyl, cyano, hydroxy, trifluoromethyl, fluoro-$(C_1-C_4)$-alkylthio, fluoro-$(C_1-C_4)$-alkylsulfinyl, fluoro-$(C_1-C_4)$-alkylsulfonyl, $(C_1-C_4)$-alkoxy-$(C_2-C_4)$-alkoxycarbonyl, N,N-di-[$(C_1-C_4)$-alkyl]carbamoyl-$(C_1-C_4)$-alkoxycarbonyl, $(C_1-C_4)$-alkylamino-$(C_2-C_4)$-alkoxycarbonyl, di-$(C_1-C_4)$-alkylamino-$(C_2-C_4)$-alkoxycarbonyl, $(C_1-C_4)$-alkoxy-$(C_2-C_4)$-alkoxy-$(C_2-C_4)$-alkoxycarbonyl, $(C_2-C_4)$-alkanoyloxy-$C_1-C_4$)-alkyl, or N-[amino-$(C_2-C_8)$-alkyl]-carbamoyl;

$R^{29}$ is hydrogen, hydroxy, amino, cyano, halogen, $(C_1-C_4)$-alkyl, carboxy or metabolically labile ester derivative thereof, $(C_1-C_4)$-alkylamino, di-$(C_1-C_4)$-alkylamino, $(C_1-C_6)$-alkoxycarbonyl, $(C_2-C_4)$-alkanoyl, $(C_1-C_4)$-alkoxy, carboxy-$(C_1-C_4)$-alkoxy, $(C_1-C_4)$-alkoxycarbonyl-($C_1$-$C_4$)-alkoxy, carbamoyl, N—($C_1$-$C_8$)-alkylcarbamoyl, N,N-di-($C_1$-$C_8$)-alkylcarbamoyl, N-[amino-($C_2$-$C_8$)-alkyl]-carbamoyl, N—[($C_1$-$C_4$)-alkylamino-($C_1$-$C_8$)-alkyl]-carbamoyl, N-[di-($C_1$-$C_4$)-alkylamino-($C_1$-$C_8$)-alkyl]]-carbamoyl, N-cyclohexylcarbamoyl, N-[cyclopentyl]-carbamoyl, N—($C_1$-$C_4$)-alkylcyclohexylcarbamoyl, N—($C_1$-$C_4$)-alkylcyclopentylcarbamoyl, N-phenylcarbamoyl, N—($C_1$-$C_4$)-alkyl-N-phenylcarbamoyl, N,N-diphenylcarbamoyl, N-[phenyl-($C_1$-$C_4$)-alkyl]-carbamoyl, N—($C_1$-$C_4$)-alkyl-N-[phenyl-($C_1$-$C_4$)-alkyl]-carbamoyl, or N,N-di-[phenyl-($C_1$-$C_4$)-alkyl]-carbamoyl, said phenyl or phenyl groups being optionally substituted with 1 to 4 identical or different halogen, ($C_1$-$C_4$)-alkyoxy, ($C_1$-$C_4$)-alkyl, cyano, hydroxy, trifluoromethyl, N—[($C_2$-$C_4$)-alkanoyl]-carbamoyl, N—[($C_1$-$C_4$)-alkoxycarbonyl]-carbamoyl, N-[fluoro-($C_2$-$C_6$)-alkyl]-carbamoyl, N,N-[fluoro-($C_2$-$C_6$)-alkyl]-N—($C_1$-$C_4$)-alkylcarbamoyl, N,N-[difluoro-($C_2$-$C_6$)-alkyl]carbamoyl, pyrrolidin-1-ylcarbonyl, piperidinocarbonyl, piperazin-1-ylcarbonyl, morpholinocarbonyl, wherein the heterocyclic group, is optionally substituted with 1 to 4, ($C_1$-$C_4$)-alkyl, benzyl, 1,2,3,4-tetrahydro-isoquinolin-2-ylcarbonyl, N,N-[di-($C_1$-$C_4$)-alkyl]-thiocarbamoyl, N—($C_2$-$C_4$)-alkanoylamino, or N—[($C_1$-$C_4$)-alkoxycarbonyl]-amino;

$R^{30}$ is hydrogen, ($C_1$-$C_4$)-alkyl, ($C_2$-$C_4$)-alkoxy, halo, nitro, hydroxy, fluoro-(1-4C)alkyl, or pyridinyl;

$R^{31}$ is hydrogen, ($C_1$-$C_4$)-alkyl, ($C_2$-$C_4$)-alkoxy, halo, nitro, hydroxy, fluoro-($C_1$-$C_4$)-alkyl, pyridinyl, or methoxy;

$R^{32}$ is hydrogen, hydroxy, amino, ($C_1$-$C_4$)-alkylamino, di-($C_1$-$C_4$)-alkylamino, halo, ($C_1$-$C_4$)-alkoxy-($C_2$-$C_4$)-alkoxy, fluoro-($C_1$-$C_6$)-alkoxy, pyrrolidin-1-yl, piperidino, piperazin-1-yl, or morpholino, wherein the heterocyclic group is optionally substituted with 1 to 4 identical or different ($C_1$-$C_4$)-alkyl or benzyl; and $R^{33}$ and $R^{34}$ are individually selected from hydrogen, ($C_1$-$C_4$)-alkyl, and ($C_1$-$C_4$)-alkoxy; including pharmaceutically-acceptable salts, esters, and pro-drugs derived therefrom.

Exemplary compounds of Formula II are described in U.S. Pat. Nos. 5,916,898 and 6,200,974, and International Publication No. WO 99/21860. All compounds listed in the foregoing patents and publication, in particular, those listed in the compound claims and the final products of the working examples, are hereby incorporated into the present application by reference herein. Exemplary compounds of Formula II include 4-oxo-1,4-dihydro-[1,10]phenanthroline-3-carboxylic acid (Compound F; see, e.g., Seki et al. (1974) Chem Abstracts 81:424, No. 21), 3-carboxy-5-hydroxy-4-oxo-3,4-dihydro-1,10-phenanthroline, 3-carboxy-5-methoxy-4-oxo-3,4-dihydro-1,10-phenanthroline, 5-methoxy-4-oxo-1,4-dihydro-[1,10]phenanthroline-3-carboxylic acid ethyl ester, 5-methoxy-4-oxo-1,4-dihydro-[1,10]phenanthroline-3-carboxylic acid, and 3-carboxy-8-hydroxy-4-oxo-3,4-dihydro-1,10-phenanthroline.

In certain aspects, compounds of the present invention include aryl-sulfono-amino-hydroxamates. Exemplary aryl-sulfono-amino-hydroxamates are disclosed in, e.g., International Publication No. WO 03/049686, International Publication No. WO 03/053997, and International Publication No. WO 04/108121. Such compounds include compounds of Formula III

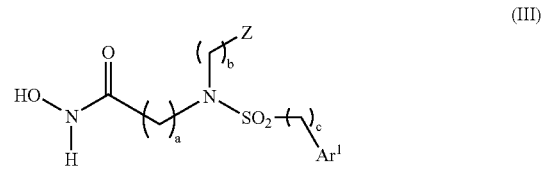

(III)

or pharmaceutically acceptable salts thereof, wherein:
a is an integer from 1 to 4;
b is an integer from 0 to 4;
c is an integer from 0 to 4;
Z is selected from the group consisting of ($C_3$-$C_{10}$) cycloalkyl, ($C_3$-$C_{10}$) cycloalkyl independently substituted with one or more $Y^1$, 3-10 membered heterocycloalkyl and 3-10 membered heterocycloalkyl independently substituted with one or more $Y^1$; ($C_5$-$C_{20}$) aryl, ($C_5$-$C_{20}$) aryl independently substituted with one or more $Y^1$, 5-20 membered heteroaryl and 5-20 membered heteroaryl independently substituted with one or more $Y^1$;
$Ar^1$ is selected from the group consisting of ($C_5$-$C_{20}$) aryl, ($C_5$-$C_{20}$) aryl independently substituted with one or more $Y^2$, 5-20 membered heteroaryl and 5-20 membered heteroaryl independently substituted with one or more $Y^2$;
each $Y^1$ is independently selected from the group consisting of a lipophilic functional group, ($C_5$-$C_{20}$) aryl, ($C_6$-$C_{26}$) alkaryl, 5-20 membered heteroaryl and 6-26 membered alk-heteroaryl;
each $Y^2$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)— NR'R', tetrazol-5-yl, —NR'—C(O)—OR', —C(NR'R')=NR', —S(O)—R', —S(O)—R", and —NR'—C(S)—NR'R'; and
each R' is independently selected from the group consisting of —H, ($C_1$-$C_8$) alkyl, ($C_2$-$C_8$) alkenyl, and ($C_2$-$C_8$) alkynyl; and
each R" is independently selected from the group consisting of ($C_5$-$C_{20}$) aryl and ($C_5$-$C_{20}$) aryl independently substituted with one or more —OR', —SR', —NR'R', —NO$_2$, —CN, halogen or trihalomethyl groups,
or wherein c is 0 and $Ar^1$ is an N' substituted urea-aryl, the compound has the structural Formula IIIa:

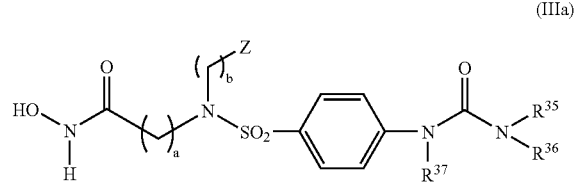

(IIIa)

or pharmaceutically acceptable salts thereof, wherein:
a, b, and Z are as defined above; and
$R^{35}$ and $R^{36}$ are each independently selected from the group consisting of hydrogen, ($C_1$-$C_8$) alkyl, ($C_2$-$C_8$) alkenyl, ($C_2$-$C_8$) alkynyl, ($C_3$-$C_{10}$) cycloalkyl, ($C_5$-$C_{20}$) aryl, ($C_5$-$C_{20}$) substituted aryl, ($C_6$-$C_{26}$) alkaryl, ($C_6$-$C_{26}$) substituted alkaryl, 5-20 membered heteroaryl, 5-20 membered substituted heteroaryl, 6-26 membered alk-heteroaryl, and 6-26 membered substituted alk-heteroaryl; and $R^{37}$ is independently selected from the group consisting of hydrogen, $(C_1-C_8)$ alkyl, $(C_2-C_8)$ alkenyl, and $(C_2-C_8)$ alkynyl.

Exemplary compounds of Formula III are described in International Publication No. WO 00/50390. All compounds listed in WO 00/50390, in particular, those listed in the compound claims and the final products of the working examples, are hereby incorporated into the present application by reference herein. Exemplary compounds of Formula III include 3-{[4-(3,3-dibenzyl-ureido)-benzenesulfonyl]-[2-(4-methoxy-phenyl)-ethyl]-amino}-N-hydroxy-propionamide (Compound G), 3-{{4-[3-(4-chloro-phenyl)-ureido]-benzenesulfonyl}-[2-(4-methoxy-phenyl)-ethyl]-amino}-N-hydroxy-propionamide, and 3-{{4-[3-(1,2-diphenyl-ethyl)-ureido]-benzenesulfonyl}-[2-(4-methoxy-phenyl)-ethyl]-amino}-N-hydroxy-propionamide.

In certain embodiments, a 2-oxoglutarate mimetic of the present invention is selected from a compound of the Formula IV

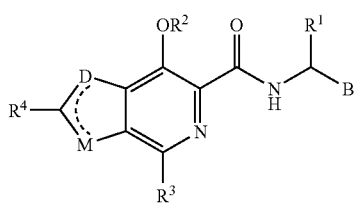

(IV)

wherein $R^1$ are selected from the group consisting of hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of $(C_1-C_{20})$-alkyl radical, $(C_3-C_8)$ cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkenynyl radical;

$R^2$ is selected from the group consisting of hydrogen, $(C_1-C_{10})$-alkyl, $(C_2-C_{10})$-alkenyl, $(C_2-C_{10})$-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and $(C_7-C_{11})$-aralkyl;

one of D or M is —S—, and the other is =$C(R^5)$—;

$R^3$, $R^4$, and $R^5$ are identical or different and are selected from the group consisting of hydrogen, hydroxyl, halogen, cyano, trifluoromethyl, nitro, carboxyl; $(C_1-C_{20})$-alkyl, $(C_3-C_8)$-cycloalkyl, $(C_3-C_8)$-cycloalkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_6-C_{12})$-aryloxy, $(C_7-C_{16})$-aralkyloxy, $(C_1-C_{16})$-hydroxyalkyl, —O—$[CH_2]_xC_fH_{(2f+1-g)}F_g$, —$OCF_2Cl$, —$OCF_2$—$CHFCl$, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N—$(C_1-C_{10})$-alkyl-N—$(C_7-C_{16})$-aralkylcarbamoyloxy, N—$((C_1-C_{10})$-alkyl)-carbamoyloxy, N—$(C_1-C_{10})$-alkyl-N—$((C_7-C_{16})$-aralkyloxy-$(C_1-C_{10})$-alkyl)-carbamoyloxyamino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, amino-$(C_1-C_{10})$-alkyl, $(C_1-C_{20})$-alkylmercapto, $(C_1-C_{20})$-alkylsulfinyl, $(C_1-C_{20})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N—$(C_1-C_{10})$-alkylsulfamoyl, N,N-di-$(C_1-C_{10})$-alkylsulfamoyl, $(C_3-C_8)$-cycloalkylsulfamoyl, N—$(C_6-C_{12})$-arylsulfamoyl, N—$(C_7-C_{16})$-aralkylsulfamoyl, N—$(C_1-C_{10})$-alkyl-N—$(C_6-C_{12})$-arylsulfamoyl, N—$(C_1-C_{10})$-alkyl-N—$(C_7-C_{16})$-aralkylsulfamoyl, $(C_1-C_{10})$-alkylsulfonamido, $(C_7-C_{16})$-aralkylsulfonamido, and N—$((C_1-C_{10})$-alkyl-$(C_7-C_{16})$-aralkylsulfonamido; where an aryl radical may be substituted by 1 to 5 substituents selected from hydroxyl, halogen, cyano, trifluoromethyl, nitro, carboxyl, $(C_2-C_{16})$-alkyl, $(C_3-C_8)$-cycloalkyl, $(C_3-C_8)$-cycloalkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkenyloxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, and —$OCF_2$—$CHFCl$;

x is 0 to 3;

f is 1 to 8; and g is 0 or 1 to (2f+1);

including the physiologically active salts, esters, and prodrugs derived therefrom.

Compounds of Formula IV include, but are not limited to, [(2-bromo-4-hydroxy-thieno[2,3-c]pyridine-5-carbonyl)- amino]-acetic acid, [(2-bromo-7-hydroxy-thieno[3,2-c]pyridine-6-carbonyl)-amino]-acetic acid, {[4-hydroxy-2-(4-methoxy-phenyl)-thieno[2,3-c]pyridine-5-carbonyl]-amino}-acetic acid, {[7-hydroxy-2-(4-methoxy-phenyl)-thieno[3,2-c]pyridine-6-carbonyl]-amino}-acetic acid, [(4-hydroxy-2,7-dimethyl-thieno[2,3-c]pyridine-5-carbonyl)-amino]-acetic acid, [(7-hydroxy-2,4-dimethyl-thieno[3,2-c]pyridine-6-carbonyl)-amino]-acetic acid, {[7-hydroxy-4-methyl-2-(4-phenoxy-phenyl)-thieno[3,2-c]pyridine-6-carbonyl]-amino}-acetic acid, {[4-hydroxy-2-(4-phenoxy-phenyl)-7-methyl-thieno[2,3-c]pyridine-5-carbonyl]-amino}-acetic acid, {[4-hydroxy-2-(4-phenoxy-phenyl)-thieno[2,3-c]pyridine-5-carbonyl]-amino}-acetic acid, {[7-hydroxy-2-(4-phenoxy-phenyl)-thieno[3,2-c]pyridine-6-carbonyl]-amino}-acetic acid, [(2,7-dibromo-4-hydroxy-thieno[2,3-c]pyridine-5-carbonyl)-amino]-acetic acid, [(2-bromo-7-chloro-4-hydroxy-thieno[2,3-c]pyridine-5-carbonyl)-amino]-acetic acid, [(7-hydroxy-thieno[3,2-c]pyridine-6-carbonyl)-amino]-acetic acid, [(4-hydroxy-thieno[2,3-c]pyridine-5-carbonyl)-amino]-acetic acid, [(2-bromo-4-chloro-7-hydroxy-thieno[3,2-c]pyridine-6-carbonyl)-amino]-acetic acid, [(2,4-dibromo-7-hydroxy-thieno[3,2-c]pyridine-6-carbonyl)-amino]-acetic acid, [(7-hydroxy-2-phenylsulfanyl-thieno[3,2-c]pyridine-6-carbonyl)-amino]-acetic acid, [(4-hydroxy-2-phenylsulfanyl-thieno[2,3-c]pyridine-5-carbonyl)-amino]-acetic acid, [(4-hydroxy-2,7-diphenyl-thieno[2,3-c]pyridine-5-carbonyl)-amino]-acetic acid, [(7-hydroxy-2,4-diphenyl-thieno[3,2-c]pyridine-6-carbonyl)-amino]-acetic acid, [(7-hydroxy-2-styryl-thieno[3,2-c]pyridine-6-carbonyl)-amino]-acetic acid, [(7-hydroxy-2-phenoxy-thieno[3,2-c]pyridine-6-carbonyl)-amino]-acetic acid, [(7-hydroxy-2-phenethyl-thieno[3,2-c]pyridine-6-carbonyl)-amino]-acetic acid, {[7-hydroxy-2-(3-trifluoromethyl-phenyl)-thieno[3,2-c]pyridine-6-carbonyl]-amino}-acetic acid, {[4-bromo-7-hydroxy-2-(3-trifluoromethyl-phenyl)-thieno[3,2-c]pyridine-6-carbonyl]-amino}-acetic acid, {[4-cyano-7-hydroxy-2-(3-trifluoromethyl-phenyl)-thieno[3,2-c]pyridine-6-carbonyl]-amino}-acetic acid, [(2-cyano-7-hydroxy-thieno[3,2-c]pyridine-6-carbonyl)-amino]-acetic acid, {[7-hydroxy-2-(4-trifluoromethyl-phenyl)-thieno[3,2-c]pyridine-6-carbonyl]-amino}-acetic acid, {[7-hydroxy-2-(2-trifluoromethyl-phenyl)-thieno[3,2-c]pyridine-6-carbonyl]-amino}-acetic acid, {[4-bromo-3-(4-fluoro-phenyl)-7-hydroxy-thieno[3,2-c]pyridine-6-carbonyl]-amino}-acetic acid, {[3-(4-fluoro-phenyl)-7-hydroxy-thieno[3,2-c]pyridine-6-carbonyl]-amino}-acetic acid, {[3-(4-fluoro-phenyl)-7-hydroxy-4-methyl-thieno[3,2-c]pyridine-6-carbonyl]-amino}-acetic acid, {[4-cyano-3-(4-fluoro-phenyl)-7-hydroxy-thieno[3,2-c]pyridine-6-carbonyl]-amino}-acetic acid, {[2-(4-fluoro-phenyl)-7-hydroxy-thieno[3,2-c]pyridine-6-carbonyl]-amino}-acetic acid, {[2-(4-fluoro-phenyl)-7-hydroxy-4-methyl-thieno[3,2-c]pyridine-6-carbonyl]-amino}-acetic acid, {[2,3-bis-(4-fluoro-phenyl)-7-hydroxy-thieno[3,2-c]pyridine-6-carbonyl]-amino}-acetic acid, {[7-bromo-3-(4-fluoro-phenyl)-4-hydroxy-thieno[2,3-c]pyridine-5-carbonyl]-amino}-acetic acid, {[3-(4-fluoro-phenyl)-4-hydroxy-thieno[2,3-c]pyridine-5-carbonyl]-amino}-acetic acid, {[2-(4-fluoro-phenyl)-4-hydroxy-thieno[2,3-c]pyridine-5-carbonyl]-amino}-acetic acid, {[2-(4-fluoro-phenyl)-4-hydroxy-7-methyl-thieno[2,3-c]pyridine-5-carbonyl]-amino}-acetic acid, [(7-chloro-4-hydroxy-thieno[2,3-c]pyridine-5-carbonyl)-amino]-acetic acid, [(4-chloro-7-hydroxy-thieno[3,2-c]pyridine-6-carbonyl)-amino]-acetic acid, [(7-bromo-4-hydroxy-thieno[2,3-c]pyridine-5-carbonyl)-amino]-acetic acid, [(4-bromo-7-hydroxy-thieno[3,2-c]pyridine-6-carbonyl)-amino]-acetic acid, [(4-hydroxy-7-phenyl-thieno[2,3-c]pyridine-5-carbonyl)-amino]-acetic acid, [(7-hydroxy-4-phenyl-thieno[3,2-c]pyridine-6-carbonyl)-amino]-acetic acid, {[7-(4-fluoro-phenyl)-4-hydroxy-thieno[2,3-c]pyridine-5-carbonyl]-amino}-acetic acid, {[4-(4-fluoro-phenyl)-7-hydroxy-thieno[3,2-c]pyridine-6-carbonyl]-amino}-acetic acid, 2-(7-(furan-2-yl)-4-hydroxythieno[2,3-c]pyridine-5-carboxamido)acetic acid, [(4-furan-2-yl-7-hydroxy-thieno[3,2-c]pyridine-6-carbonyl)-amino]-acetic acid, [(7-furan-3-yl-4-hydroxy-thieno[2,3-c]pyridine-5-carbonyl)-amino]-acetic acid, [(4-furan-3-yl-7-hydroxy-thieno[3,2-c]pyridine-6-carbonyl)-amino]-acetic acid, 2-(4-hydroxy-7-(thiophen-2-yl)thieno[2,3-c]pyridine-5-carboxamido)acetic acid, [(7-hydroxy-4-thiophen-2-yl-thieno[3,2-c]pyridine-6-carbonyl)-amino]-acetic acid, [(4-hydroxy-7-thiophen-3-yl-thieno[2,3-c]pyridine-5-carbonyl)-amino]-acetic acid, [(7-hydroxy-4-thiophen-3-yl-thieno[3,2-c]pyridine-6-carbonyl)-amino]-acetic acid, [(4-hydroxy-7-methyl-thieno[2,3-c]pyridine-5-carbonyl)-amino]-acetic acid, [(7-hydroxy-4-methyl-thieno[3,2-c]pyridine-6-carbonyl)-amino]-acetic acid, [(7-ethynyl-4-hydroxy-thieno[2,3-c]pyridine-5-carbonyl)-amino]-acetic acid, [(4-ethynyl-7-hydroxy-thieno[3,2-c]pyridine-6-carbonyl)-amino]-acetic acid, [(7-cyano-4-hydroxy-thieno[2,3-c]pyridine-5-carbonyl)-amino]-acetic acid, and [(4-cyano-7-hydroxy-thieno[3,2-c]pyridine-6-carbonyl)-amino]-acetic acid.

Exemplary compounds for use in the present methods include Compound A (1-Chloro-4-hydroxy-isoquinoline-3-carbonyl)-amino]-acetic acid; Compound B (S)-2-[(4-Hydroxy-7-phenoxy-isoquinoline-3-carbonyl)-amino]-propionic acid; Compound C {[4-Hydroxy-7-(4-methoxy-phenoxy)-isoquinoline-3-carbonyl]-amino}-acetic acid; Compound D [(4-Hydroxy-1-methyl-7-phenoxy-isoquinoline-3-carbonyl)-amino]-acetic acid, Compound E [7-(4-Fluoro-phenoxy)-4-hydroxy-isoquinoline-3-carbonyl]-amino-acetic acid, Compound F [4-Oxo-1,4-dihydro-[1,10] phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid.

Unless otherwise specified, the term "alkyl" as used herein refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

The term "substituted alkyl" unless otherwise specified is used herein to refer to an alkyl group, of from 1 to 10 carbon atoms, preferably, 1 to 5 carbon atoms, having from 1 to 5 substituents, preferably 1 to 3 substituents, independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{40}$R$^{40}$ where each R$^{40}$ is hydrogen or alkyl, —NR$^{40}$S(O)$_2$-alkyl, —NR$^{40}$S(O)$_2$-substituted alkyl, —NR$^{40}$S(O)$_2$-aryl, —NR$^{40}$S(O)$_2$-substituted aryl, —NR$^{40}$S(O)$_2$-heteroaryl, —NR$^{40}$S(O)$_2$-substituted heteroaryl, —NR$^{40}$S(O)$_2$-heterocyclic, —NR$^{40}$S(O)$_2$-substituted heterocyclic, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic where each R$^{40}$ is hydrogen or alkyl.

"Alkoxy" unless otherwise specified is used herein to refer to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" unless otherwise specified is used herein to refer to the group "substituted alkyl-O—".

"Acyl" unless otherwise specified is used herein to refer to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The terms "aminoacyl" or, as a prefix, "carbamoyl" or "carboxamide," or "substituted carbamoyl," or "substituted carboxamide," are used herein unless otherwise specified to refer to the group —C(O)NR$^{142}$R$^{142}$ where each R$^{142}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{142}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" unless otherwise specified is used herein to refer to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" unless otherwise specified is used herein to refer to alkenyl group preferably having from 2 to 6 carbon atoms and more preferably 2 to 4 carbon atoms and having at least 1 and preferably from 1 to 2 sites of alkenyl unsaturation.

"Substituted alkenyl" unless otherwise specified is used herein to refer to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkynyl" unless otherwise specified is used herein to refer to alkynyl group preferably having from 2 to 6 carbon atoms and more preferably 2 to 3 carbon atoms and having at least 1 and preferably from 1-2 sites of alkynyl unsaturation.

"Substituted alkynyl" unless otherwise specified is used herein to refer to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group —NH$_2$.

"Substituted amino" unless otherwise specified is used herein to refer to the group —NR$^{141}$R$^{141}$, where each R$^{141}$ group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R$^{141}$ groups are not hydrogen; or the R$^{141}$ groups can be joined together with the nitrogen atom to form a heterocyclic or substituted heterocyclic ring.

"Acylamino" unless otherwise specified is used herein to refer to the groups —NR$^{145}$C(O)alkyl, —NR$^{145}$C(O) substituted alkyl, —NR$^{145}$C(O)cycloalkyl, —NR$^{145}$C(O) substituted cycloalkyl, —NR$^{145}$C(O)alkenyl, —NR$^{145}$C(O) substituted alkenyl, —NR$^{145}$C(O)alkynyl, —NR$^{145}$C(O) substituted alkynyl, —NR$^{145}$C(O)aryl, —NR$^{145}$C(O) substituted aryl, —NR$^{145}$C(O)heteroaryl, —NR$^{145}$C(O) substituted heteroaryl, —NR$^{145}$C(O)heterocyclic, and —NR$^{145}$C(O) substituted heterocyclic where R$^{145}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

"Carbonyloxyamino" unless otherwise specified is used herein to refer to the groups —NR$^{146}$C(O)O-alkyl, —NR$^{146}$C(O)O-substituted alkyl, —NR$^{146}$C(O)O-alkenyl, —NR$^{146}$C(O)O-substituted alkenyl, —NR$^{146}$C(O)O-alkynyl, —NR$^{146}$C(O)O-substituted alkynyl, —NR$^{146}$C(O)O-cycloalkyl, NR$^{146}$C(O)O-substituted cycloalkyl, —NR$^{146}$C(O)O-aryl, —NR$^{146}$C(O)O-substituted aryl, —NR$^{146}$C(O)O-heteroaryl, —NR$^{146}$C(O)O-substituted heteroaryl, —NR$^{146}$C(O)O-heterocyclic, and —NR$^{146}$C(O)O-substituted heterocyclic where $R^{146}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy," or, as a prefix, "carbamoyloxy," or "substituted carbamoyloxy," are used herein unless otherwise specified to refer to the groups —OC(O)NR$^{147}$R$^{147}$ where each $R^{147}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each $R^{147}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" unless otherwise specified is used herein to refer to the group —NR$^{149}$C(O)NR$^{149}$— where $R^{149}$ is selected from the group consisting of hydrogen and alkyl.

"Aryl" or "Ar" unless otherwise specified are used herein to refer to a monovalent aromatic carbocyclic group of from 6 to 14 carbon atoms having a single ring (e.g., phenyl) or multiple condensed rings (e.g., naphthyl or anthryl), which condensed rings may or may not be aromatic (e.g., 2-benzoxazolinone, 2H-1,4-benzoxazin-3(4H)-one-7-yl, and the like), provided that the point of attachment is the aryl group. Preferred aryls include phenyl and naphthyl.

"Substituted aryl" unless otherwise specified is used herein to refer to aryl groups, as defined herein, which are substituted with from 1 to 4, preferably 1-3, substituents selected from the group consisting of hydroxy, acyl, acylamino, carbonylaminothio, acyloxy, alkyl, substituted alkyl, alkoxy, substituted alkoxy, alkenyl, substituted alkenyl, alkynyl, substituted alkynyl, amidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{151}$R$^{151}$ where each $R^{151}$ is hydrogen or alkyl, —NR$^{151}$S(O)$_2$-alkyl, —NR$^{151}$S(O)$_2$-substituted alkyl, —NR$^{151}$S(O)$_2$-aryl, —NR$^{151}$S(O)$_2$-substituted aryl, —NR$^{151}$S(O)$_2$-heteroaryl, —NR$^{151}$S(O)$_2$-substituted heteroaryl, —NR$^{151}$S(O)$_2$-heterocyclic, —NR$^{151}$S(O)$_2$-substituted heterocyclic, —NR$^{151}$S(O)$_2$—NR$^{151}$-alkyl, —NR$^{151}$S(O)$_2$—NR$^{151}$-substituted alkyl, —NR$^{151}$S(O)$_2$—NR$^{151}$-aryl, —NR$^{151}$S(O)$_2$—NR$^{151}$-substituted aryl, —NR$^{151}$S(O)$_2$—NR$^{151}$-heteroaryl, —NR$^{151}$S(O)$_2$—NR$^{151}$-substituted heteroaryl, —NR$^{151}$S(O)$_2$—NR$^{151}$-heterocyclic, —NR$^{151}$S(O)$_2$—NR$^{151}$-substituted heterocyclic where each $R^{151}$ is hydrogen or alkyl, wherein each of the terms is as defined herein.

"Aryloxy" unless otherwise specified is used herein to refer to the group aryl-O— that includes, by way of example, phenoxy, naphthoxy, and the like.

"Substituted aryloxy" unless otherwise specified is used herein to refer to substituted aryl-O— groups.

"Aryloxyaryl" unless otherwise specified is used herein to refer to the group -aryl-O-aryl.

"Substituted aryloxyaryl" unless otherwise specified is used herein to refer to aryloxyaryl groups substituted with from 1 to 3 substituents on either or both aryl rings as defined above for substituted aryl.

"Carboxyl" refers to —COOH or salts thereof.

"Carboxyl esters" unless otherwise specified is used herein to refer to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cycloalkyl" unless otherwise specified is used herein to refer to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" unless otherwise specified is used herein to refer to a cycloalkyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" unless otherwise specified is used herein to refer to —O-cycloalkyl groups.

"Substituted cycloalkoxy" unless otherwise specified is used herein to refer to —O-substituted cycloalkyl groups.

"Halo" or "halogen" refer to fluoro, chloro, bromo and iodo and, preferably, fluoro or chloro.

"Heteroaryl" unless otherwise specified is used herein to refer to an aromatic group of from 1 to 15 carbon atoms, preferably from 1 to 10 carbon atoms, and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl). Preferred heteroaryls include pyridinyl, pyrrolyl, indolyl, thiophenyl, and furyl.

"Substituted heteroaryl" unless otherwise specified is used herein to refer to heteroaryl groups that are substituted with from 1 to 3 substituents selected from the same group of substituents defined for substituted aryl.

"Heteroaryloxy" unless otherwise specified is used herein to refer to the group —O-heteroaryl and "substituted heteroaryloxy" refers to the group —O-substituted heteroaryl.

"Heterocycle" or "heterocyclic" unless otherwise specified are used herein to refer to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl provided that the point of attachment is at the heterocycle.

"Substituted heterocyclic" unless otherwise specified is used herein to refer to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" unless otherwise specified is used herein to refer to the group —O-heterocyclic and "substituted heterocyclyloxy" refers to the group —O-substituted heterocyclic.

"Thiol" or "mercapto" refer to the group —SH.

"Alkylsulfanyl" and "alkylthio" unless otherwise specified are used herein to refer to the groups —S-alkyl where alkyl is as defined above.

"Substituted alkylthio" and "substituted alkylsulfanyl" unless otherwise specified are used herein to refer to the group —S-substituted alkyl is as defined above.

"Cycloalkylthio" or "cycloalkylsulfanyl" unless otherwise specified are used herein to refer to the groups —S-cycloalkyl where cycloalkyl is as defined above.

"Substituted cycloalkylthio" unless otherwise specified is used herein to refer to the group —S-substituted cycloalkyl where substituted cycloalkyl is as defined above.

"Arylthio" unless otherwise specified is used herein to refer to the group —S-aryl and "substituted arylthio" unless otherwise specified is used herein to refer to the group —S-substituted aryl where aryl and substituted aryl are as defined above.

"Heteroarylthio" unless otherwise specified is used herein to refer to the group —S-heteroaryl and "substituted heteroarylthio" unless otherwise specified is used herein to refer to the group —S-substituted heteroaryl where heteroaryl and substituted heteroaryl are as defined above.

"Heterocyclicthio" unless otherwise specified is used herein to refer to the group —S-heterocyclic and "substituted heterocyclicthio" unless otherwise specified is used herein to refer to the group —S-substituted heterocyclic where heterocyclic and substituted heterocyclic are as defined above.

The term "amino acid" refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active .alpha.-Amino Acids, Pergamon Press (1989); Evans et al., J. Amer. Chem. Soc., 112:4011-4030 (1990); Pu et al, J. Amer. Chem. Soc., 56:1280-1283 (1991); Williams et al., J. Amer. Chem. Soc., 113:9276-9286 (1991); and all references cited therein. The present invention includes the side chains of unnatural amino acids as well.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "prodrug" refers to compounds of this invention which have been modified to include a physiologically and biocompatible removable group which group is removed in vivo to provide for the active drug, a pharmaceutically acceptable salt thereof or a biologically active metabolite thereof. Suitable removable groups are well known in the art and particularly preferred removable groups include esters of the carboxylic acid moiety on the glycine substituent. Preferably such esters include those derived from alkyl alcohols, substituted alkyl alcohols, hydroxy substituted aryls and heteroaryls and the like. Another preferred removable group are the amides formed from the carboxylic acid moiety on the glycine substituent. Suitable amides are derived from amines of the formula $HNR^{20}R^{21}$ where $R^{20}$ and $R^{21}$ are independently hydrogen, alkyl, substituted alkyl, aryl, substituted aryl, and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Methods for Identifying Compounds

Methods for identifying compounds of the invention are also provided. In certain aspects, a compound of the invention is one that stabilizes HIFα. The ability of a compound to stabilize or activate HIFα can be measured, for example, by direct measurement of HIFα in a sample, indirect measurement of HIFα, e.g., by measuring a decrease in HIFα associated with the von Hippel Lindau protein (see, e.g., International Publication No. WO 00/69908), or activation of HIF responsive target genes or reporter constructs (see, e.g., U.S. Pat. No. 5,942,434). Measuring and comparing levels of HIF and/or HIF-responsive target proteins in the absence and presence of the compound will identify compounds that stabilize HIFα and/or activate HIF.

In other aspects, a compound of the invention is one that inhibits HIF hydroxylase activity. Assays for hydroxylase activity are standard in the art. Such assays can directly or indirectly measure hydroxylase activity. For example, an assay can measure hydroxylated residues, e.g., proline, asparagine, etc., present in the enzyme substrate, e.g., a target protein, a synthetic peptide mimetic, or a fragment thereof.

(See, e.g., Palmerini et al. (1985) J Chromatogr 339:285-292.) A reduction in hydroxylated residue, e.g., proline or asparagine, in the presence of a compound is indicative of a compound that inhibits hydroxylase activity. Alternatively, assays can measure other products of the hydroxylation reaction, e.g., formation of succinate from 2-oxoglutarate. (See, e.g., Cunliffe et al. (1986) Biochem J 240:617-619.) Kaule and Gunzler (1990; Anal Biochem 184:291-297) describe an exemplary procedure that measures production of succinate from 2-oxoglutarate.

Procedures such as those described above can be used to identify compounds that modulate HIF hydroxylase activity. Target protein may include HIFα or a fragment thereof, e.g., HIF(556-575). Enzyme may include, e.g., HIF prolyl hydroxylase (see, e.g., GenBank Accession No. AAG33965, etc.) or HIF asparaginyl hydroxylase (see, e.g., GenBank Accession No. AAL27308, etc.), obtained from any source. Enzyme may also be present in a crude cell lysate or in a partially purified form. For example, procedures that measure HIF hydroxylase activity are described in Ivan et al. (2001, Science 292:464-468; and 2002, Proc Natl Acad Sci USA 99:13459-13464) and Hirsila et al. (2003, J Biol Chem 278:30772-30780); additional methods are described in International Publication No. WO 03/049686. Measuring and comparing enzyme activity in the absence and presence of the compound will identify compounds that inhibit hydroxylation of HIFα.

For clarity, an agent for use in the present methods is any compound that stabilizes HIFα. Methods for determining whether or not a particular agent stabilizes HIFα are available in the art and are described, supra. In certain embodiments, an agent for use in the present methods inhibits HIF hydroxylase activity. Methods for determining whether or not a particular agent inhibits HIF hydroxylase activity are described herein, supra.

In additional embodiments, a compound for use in the present methods is a compound that demonstrates the ability to increase expression of HIF-dependent genes corresponding to proteins associated with various anti-cancer, e.g., anti-tumor, effects, including anti-proliferative and pro-apoptotic effects. (See, e.g., Mack et al (2005) Mol Cell Biol 25: 4565-4578; Acker et al (2005) Cancer Cell 8:131-141; Savai et al (2005) Int J Oncol 27:393-400; Box et al (2004) Carcinogenesis 25:2325-2335; Carmeliet et al (1998) Nature 394:485-490; Goda et al (2003) Antioxid. Redox. Signal. 5:467-473; Hanze et al (2003) Biochem Biophys Res Commun 312:571-577; Brusselmans et al (2001) J Biol Chem 276:39192-39196; Shoshani et al (2002) Mol Cell Biol 22:2283-2293; Sowter (2001) Cancer Res 61:6669-6673; Stein et al (2004) J Biol Chem 279:48930-48940; Zhang et al (2003) Apoptosis. 8:229-236; Graham et al (2004) J Exp Biol 207:3189-3200; Webster et al (2000) Adv Exp Med Biol 475:161-175; and Shoshani et al (2002) Mol Cell Biol 22:2283-2293.).

Thus, it is contemplated in certain embodiments that a compound of the present invention can be a compound that increases expression of at least one of the following genes: BNIP3 (also known as *Homo sapiens* BCL2/adenovirus E1B 19 kD-interacting protein 3 (BNIP3) and NIP3); BNIP3L (also known as BCL2/adenovirus E1B 19 kDa interacting protein 3-like (BNIP3L) and *Homo sapiens* clone 016a05 My020 protein MRNA); NDRG1 (also known as *Homo sapiens* N-myc downstream regulated gene 1 (NDRG1), differentiation-related gene 1 protein (DRG1), N-myc downstream regulated gene 1 protein (NDR1), protein regulated by oxygen-1 (PROXY-1), etc); CDKN1C (also known as p57KIP2); and REDD1 (also known as RTP801). REDD1 is a negative regulator of mammalian target of rapamycin (mTOR) signaling. (See, e.g., Brugarolas et al (2004) Genes Dev 18:2893-2904.) mTOR is a key factor in determining the proliferative state of various cell types and elevated mTOR signaling is common to many tumors. Therefore, it is contemplated that a compound of the present invention can be a compound mTOR expression and/or activity.

That a particular compound increases expression of a HIF-dependent gene associated with anti-cancer effects can be determined by any of a number of methods available in the art. For example, the ability of a compound to increase expression of a HIF-dependent anti-cancer gene can be measured in vitro. In one exemplary method, cells are treated with the candidate compound, and the effects on expression of the HIF-dependent genes in question are measured. See, e.g., Example 8, in which various cell lines were treated with each of Compounds A, B, C, D, E, F, G, H, I, J, K, L, M, and N, and increased expression of BNIP3, BNIP3L, NDRG1, CDKN1C, and REDD1/RTP801 was observed. (See Table 14, Table 15, Table 16, Table 17, and Table 18.)

To select a compound for use in the present methods, the ability of the candidate compound to increase expression of HIF-dependent anti-cancer genes in vivo can also be measured. Methods for making such a determination are various and well-known in the art. For example, a test compound can be administered to an animal, and, subsequently, various tissues can be analyzed for levels of expression of the genes of interest. See, e.g., Example 9, in which Swiss Webster mice were administered intravenously a single dose of one of Compounds A, B, C, D, E, F, J, L, and N. Subsequently, kidney and liver tissues were analyzed and increased expression of BNIP3, BNIP3L, and NDRG1 was observed. (See Table 19 and Table 20.)

In particular embodiments, a compound suitable for use in the present methods is identified by the ability of the compound to achieve specific therapeutic effects in a validated in vivo animal model of cancer. For example, a test compound can be administered in an animal model of the human cancer of interest, and the ability of the compound to inhibit tumor growth, reduce tumor volume, reduce tumor weight, inhibit tumor progression, reduce metastatic frequency, and/or improve survival is measured. See, e.g., Examples 1 through 7, in which compounds of the present invention, Compounds A, B, C, D, and E, were administered in mouse xenograft models of lung, breast, colon, and ovarian cancer, and inhibition of tumor growth, tumor volume, tumor weight, tumor progression, metastatic frequency, as well as improvement in survival, were observed.

Combinatorial Therapies

In some embodiments, the methods of the present invention further comprise administering to the subject one or more chemotherapeutics. Accordingly, the present invention provides alternative or improved methods for the treatment or prevention of cancer. In particular, the present inventors have discovered that such combinatorial therapies may result in greater inhibition of tumor progression compared to the corresponding monotherapies. Moreover, the present inventors have discovered that such combinatorial therapies may result in improved morbidity compared to the chemotherapeutic monotherapy. In this way, the combinatorial therapies of the present invention may decrease the toxic effects of the chemotherapeutic monotherapy.

Accordingly, in some embodiments, the methods of the invention further comprise administering to the subject one or more chemotherapeutics. The administration of the one or more chemotherapeutics in combination with one or more compounds of the present may be simultaneous, separate, or sequential administration, and administration may be in any order. Suitable chemotherapeutics will be well known to the skilled person in the art. For example, the chemotherapeutics may be selected from the group consisting of alkylating agents; nitrosoureas; antimetabolites; anthracyclines and related drugs; topoisomerase II inhibitors; mitotic inhibitors and corticosteroid hormones. Known alkylating agents include busulfan, cisplatin, carboplatin, chlorambucil, cyclophosphamide, ifosfamide, dacarbazine (DTIC), mechlorethamine (nitrogen mustard), melphalan and temozolomide. Known nitrosoureas include carmustine (BCNU) and lomustine (CCNU). Known antimetabolites include 5-fluorouracil, capecitabine, 6-mercaptopurine, methotrexate, gemcitabine, cytarabine (ara-C), fludarabine and pemetrexed. Known anthracyclines and related drugs include daunorubicin, doxorubicin (Adriamycin), epirubicin, idarubicin and mitoxantrone. Known topoisomerase II inhibitors include topotecan, irinotecan, etoposide (VP-16) and teniposide. Known mitotic inhibitors include taxanes (paclitaxel, docetaxel) and the vinca alkaloids (vinblastine, vincristine and vinorelbine). Known corticosteroid hormones include prednisone and dexamethasone.

The chemotherapeutics may also be selected from other known chemotherapeutics, e.g. L-asparaginase, dactinomycin, thalidomide, tretinoin, imatinib (Gleevec), gefitinib (Iressa), erlotinib (Tarceva), rituximab (Rituxan), bevacizumab (Avastin), anti-estrogens (tamoxifen, fulvestrant), aromatase inhibitors (anastrozole, exemestane, letrozole), progestins (megestrol acetate), anti-androgens (bicalutamide, flutamide) and LHRH agonists (leuprolide, goserelin).

It is particularly contemplated that the chemotherapeutic agent can be, for example, a microtubule poison, a DNA alkylating agent, etc. Suitable microtubule poisons include, but are not limited to, paclitaxel. Suitable DNA alkylating agents include, e.g., carboplatin, etc.

Modes of Administration

The compositions of the present invention can be delivered directly or in pharmaceutical compositions containing excipients, as is well known in the art. The present methods of treatment involve administration of an effective amount of a compound of the present invention to a subject having or at risk for having cancer.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

In preferred embodiments, the compounds of the present invention are administered orally. For example, in certain embodiments, the invention provides for oral administration of a compound selected from the group consisting of: Compound A [(1-Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page, Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro)-emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons dervided from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician, e.g., treatment of cancer, including induction of anti-tumor effects, etc.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

In some embodiment of the present invention, effective doses for preferred compounds of the invention (e.g., Compound A [(1-Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10] phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid) include 3 mg/kg, 6 mg/kg, 10 mg/kg, 15 mg/kg, 20 mg/kg and 30 mg/kg. These doses are therefore particularly preferred for use in the present invention.

In additional embodiments, effective treatment regimes for preferred compounds of the invention (e.g., Compound A [(1-Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid) include administration two or three times weekly. These regimes are therefore particularly preferred for use in the present invention.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1

Compounds and Methods of the Invention Limit Progression of Subcutaneously Implanted Human H-460 Lung Tumors in a Mouse Xenograft Model Immuno-compromised athymic CD-1 nu/nu nude mice males (5-6 weeks old) were used in this study (Charles River Laboratories, Wilmington, Mass.). Animals were maintained in a HEPA-filtered environment during the experimental period. Cages, food, and bedding were autoclaved. Animal diets were obtained from Harlan Teklad (Madison, Wis.). Hydrochloric acid, 0.15% (v/v), was added to the drinking water.

Compounds of the invention were pre-formulated in an aqueous vehicle consisting of 0.1% (w/w) Polysorbate 80 (J T Baker) and 0.5% (w/w) high viscosity carboxymethyl cellulose sodium (Spectrum) to achieve a final 10 ml/kg dosing (oral gavage). The stock solution for Taxol (Florida Infusion) was diluted to proper concentration with sterile saline for i.v. injection before use.

The human H460 lung cancer cell line used was obtained from the National Cancer Institute. (Brower et al., (1986) Cancer Res 46:798-806.) Xenografted H-460 tumors are sensitive to chemotherapeutics commonly used in treatment of lung cancer. (See, e.g., Kraus-Berthier et al., (2000) Clin Cancer Res 6:297-304 and Lai et al., J Biomed Sci (2000) 7:64-70.)

A stock tumor was established by subcutaneously injecting a cell suspension into nude mice. The resulting tumor was maintained in nude mice subcutaneously as tumor stock prior to use. Tumor implantation was performed when the stock tumors were in log phase of growth. Before implantation, tumor tissue was harvested from stock mice and placed in RPMI-1640 medium. Necrotic tissues were dissected away and viable tissues were cut into 1-2 mm² pieces. Tumor fragments were then transplanted subcutaneously to the right flank of the nude mice.

Treatment (administration of compounds of the present invention) was started when the inoculated tumors reached approximately 100 mm³, and continued for four weeks. Table 1 below shows the study design and treatments used in each group.

TABLE 1

| Group number | Agent | Dose | Schedule | Route | n |
|---|---|---|---|---|---|
| 1 | CMC Vehicle | 10 ml/kg | M, W, F × 4 | PO | 10 |
| 2 | Taxol | 15 mg/kg | Every 3D × 4 | i.v. | 10 |
| 3 | Cmpd A | 20 mg/kg | M, W, F × 4 | PO | 10 |
| 4 | Cmpd A | 60 mg/kg | M, W, F × 4 | PO | 10 |
| 5 | Cmpd B | 6 mg/kg | M, W, F × 4 | PO | 10 |
| 6 | Cmpd B | 20 mg/kg | M, W, F × 4 | PO | 10 |
| 7 | Cmpd C | 20 mg/kg | M, W, F × 4 | PO | 10 |

PO, oral gavage;
i.v., intravenous infusion;
s.c., subcutaneous injection.

Sizes of the primary tumors were measured through the skin with calipers once per week. Tumor volumes were calculated by the formula $V=(W^2 \ast L)/2$. Body weight of the mice in each group was also measured once per week during the experimental period. All animals were sacrificed following thirty-two days of treatment. Primary tumors were excised and weighed on an electronic balance. Blood samples were taken during terminal sacrifice and placed in microhematocrit tubes containing EDTA. Complete Blood Counts (CBC) and reticulocyte analysis were performed with the Cell Dyn 3700 analyzer (Abbott Diagnostics), as described by the manufacturer.

Table 2 below shows the effect of various compounds of the present invention on mean tumor volumes (mm³, as measured with calipers). As shown in Table 2 below, administration of compounds of the invention resulted in reduced mean tumor volumes compared to that of vehicle controls as determined at the earliest measurement following initiation of dosing (10 days), and continuing at subsequent time points. As the study progressed, three treatment groups (Compound A, 20 mg/kg, 60 mg/kg; Compound B, 6 mg/kg, 20 mg/kgl Compound C, 20 mg/kg) consisting of compounds of the invention met statistical significance cutoffs for change vs. matched controls ($p<0.05$ repeat measures ANOVA; Sigmastat, SPSS Inc.). Taxol, included as a positive control, also produced a statistically significant inhibition of tumor progression. As shown in Table 2 below, mean tumor volumes in animals administered compounds of the present invention were reduced compared to mean tumor volumes in vehicle control animals. The observation of reduced mean tumor volumes in all groups treated with compound of the invention (compared to control) indicated that inhibition of tumor progression and growth is obtained by methods and compounds of the present invention.

TABLE 2

| Days treatment | Vehicle control | Taxol 15 mg/kg | Cmpd A 20 mg/kg | Cmpd A 60 mg/kg | Cmpd B 6 mg/kg | Cmpd B 20 mg/kg | Cmpd C 20 mg/kg |
|---|---|---|---|---|---|---|---|
| 0 | 97 | 83 | 88 | 105 | 101 | 108 | 91 |
| 10 | 1547 | 387 | 730 | 895 | 884 | 914 | 638 |
| 17 | 3065 | 813** | 1376 | 1742 | 1949 | 1858 | 1365 |
| 24 | 4476 | 1160** | 2499** | 2662* | 3131 | 3074 | 2239** |
| 31 | 4746 | 1292** | 2670** | 2968* | 3343 | 3229 | 2373** |

Values represent means (n = 10).
One death was observed in the control group (day 17; tumor at 7,000 mm³).
* = $p < 0.05$ vs. matched control,
** = $p < 0.01$ vs. matched control, repeated measures ANOVA.

Table 3 below shows the effect of various compounds of the present invention on mean animal body weights (grams). As shown in Table 3, animal body weights were similar across different treatment groups and throughout the course of the study, with some increase observed over time but not specific to any treatment group. Differences in animal body weights between treatment groups did not meet statistical significance cutoffs for change (repeated measures ANOVA). Thus, differences in tumor progression as measured by mean tumor volumes could not be attributed to any generalized toxicity or suppression of normal metabolism that might have been detected by changes in body weights.

TABLE 3

| Days treatment | Vehicle control | Taxol 15 mg/kg | Cmpd A 20 mg/kg | Cmpd A 60 mg/kg | Cmpd B 6 mg/kg | Cmpd B 20 mg/kg | Cmpd C 20 mg/kg |
|---|---|---|---|---|---|---|---|
| 0 | 25.2 | 26.6 | 25.2 | 24.5 | 26.3 | 25.7 | 25.7 |
| 10 | 29.1 | 29.5 | 30.1 | 30.0 | 27.9 | 27.8 | 29.4 |
| 17 | 29.5 | 30.6 | 30.5 | 30.5 | 29.1 | 29.0 | 29.9 |
| 24 | 30.7 | 31.1 | 30.6 | 30.6 | 29.3 | 29.3 | 31.0 |
| 31 | 31.3 | 30.9 | 30.3 | 29.9 | 29.3 | 29.3 | 30.9 |

Table 4 shows the effect of various compounds of the present invention on mean tumor weights (grams) measured at necropsy. As shown in Table 4, compounds of the invention also resulted in consistently reduced mean tumor weights at the study endpoint (day 32). One treatment group (Compound C, 20 mg/kg) met statistical significance cutoffs for change vs. the vehicle control group (p<0.05, Dunnett's ANOVA). Results from two additional groups (Compound A, 20 mg/kg; Compound A, 60 mg/kg) showed P-values of 0.07 and 0.09, respectively. The decreased number of groups meeting the statistical cutoffs for mean tumors weights at necropsy as compared to progressive measurement of tumor volumes by caliper was most likely associated with cessation of growth observed in exceptionally large tumors at late time points in the vehicle control animals. Taxol, included as a positive control, also produced a statistically significant inhibition of tumor progression, reflected in reduced mean tumor weights at the study endpoint.

Table 5 below shows complete blood counts and reticulocyte analysis in animals administered various compounds of the present invention. As shown in Table 5, blood parameters determined at the study endpoint were affected by treatment with compounds of the invention as well. Key markers of erythropoiesis were consistently increased in treated animals compared to that in control animals by treatment with the compounds of invention; including red blood cell counts (RBC), hemoglobin content (HGB), and hematocrit (HCT). One treatment group (Compound C, 20 mg/kg) met statistical significance cutoffs for change vs. the vehicle control group for both RBC and HGB (p<0.05, Dunnett's ANOVA). These results demonstrated that methods and compounds of the present invention affected both tumor progression and growth and erythropoiesis.

TABLE 4

| | Vehicle control | Taxol 15 mg/kg | Cmpd A 20 mg/kg | Cmpd A 60 mg/kg | Cmpd B 6 mg/kg | Cmpd B 20 mg/kg | Cmpd C 20 mg/kg |
|---|---|---|---|---|---|---|---|
| Mean Tumor Weight at Necropsy (g), +/−SD | 5.30 +/−2.58 | 1.59 +/−0.86 | 3.05 +/−2.48 | 3.09 +/−2.75 | 4.27 +/−3.60 | 3.60 +/−2.30 | 2.35 +/−2.54 |
| Pval (vs. control; Dunnett's ANOVA) | — | 0.002 | 0.07 | 0.09 | 0.48 | 0.15 | 0.02 |

TABLE 5

| | Vehicle control | Taxol 15 mg/kg | Cmpd A 20 mg/kg | Cmpd A 60 mg/kg | Cmpd B 6 mg/kg | Cmpd B 20 mg/kg | Cmpd C 20 mg/kg |
|---|---|---|---|---|---|---|---|
| WBC (×$10^3$/ul) | 30.9 | 10.4 | 23.2 | 19.4 | 27.3 | 20.8 | 14.9 |
| RBC (×$10^6$/ul) | 8.11 | 9.03 | 8.84 | 8.60 | 8.71 | 8.78 | 9.36 |
| HGB (g/dl) | 12.1 | 14.1 | 13.3 | 13.5 | 12.7 | 12.7 | 14.0 |
| HCT (%) | 35.5 | 41.5 | 40.4 | 39.5 | 37.7 | 37.7 | 41.1 |
| MCV (fl) | 43.8 | 45.9 | 45.6 | 45.8 | 43.2 | 43.0 | 43.8 |
| MCH (pg) | 15.0 | 15.6 | 15.1 | 15.6 | 14.6 | 14.5 | 14.9 |
| MCHC (g/dl) | 34.3 | 33.9 | 33.1 | 34.2 | 33.8 | 33.7 | 34.1 |
| RDW (%) | 21.3 | 21.8 | 21.3 | 23.6 | 21.4 | 21.7 | 22.3 |
| PLAT (×$10^3$/ul) | 1699 | 1943 | 1737 | 1858 | 1536 | 1767 | 1707 |
| RET (%) | 9.0 | 5.1 | 6.4 | 6.5 | 7.5 | 6.3 | 4.9 |
| Abs Retic | 707 | 462 | 559 | 539 | 653 | 552 | 457 |
| IRF | 0.65 | 0.56 | 0.63 | 0.65 | 0.64 | 0.56 | 0.56 |
| Neut (×$10^3$/ul) | 27.4 | 7.4 | 15.7 | 15.7 | 18.4 | 16.5 | 11.4 |
| Lymph (×$10^3$/ul) | 3.0 | 2.6 | 5.0 | 3.2 | 4.7 | 2.7 | 3.0 |
| Mono (×$10^3$/ul) | 0.3 | 0.3 | 1.48 | 0.32 | 2.37 | 0.85 | 0.32 |
| Eos (×$10^3$/ul) | 0.1 | 0.07 | 0.15 | 0.09 | 0.08 | 0.07 | 0.04 |
| Baso (×$10^3$/ul) | 0.1 | 0.07 | 0.9 | 0.06 | 1.84 | 0.78 | 0.15 |
| Neut % | 87.3 | 70.8 | 68.6 | 79.8 | 67.5 | 75.6 | 70.2 |
| Lymph % | 11.2 | 24.7 | 21.4 | 17.0 | 18.3 | 14.6 | 25.2 |
| Mono % | 0.73 | 2.97 | 5.75 | 2.04 | 7.61 | 4.88 | 2.67 |
| EOS % | 0.50 | 0.83 | 1.03 | 0.67 | 0.49 | 0.44 | 0.47 |
| Baso % | 0.30 | 0.67 | 3.34 | 0.52 | 6.35 | 4.52 | 1.47 |

Abbreviations:
WBC indicates white blood cells;
RBC, red blood cells;
HGB, hemoglobin;
HCT, hematocrit;
MCV, mean corpuscular volume;
MCH, mean corpuscular hemoglobin;
MCHC, MCH concentration;
PLAT, platelets;
RDW, RBC distribution width;
RET, reticulocytes;
Abs Retic, reticulocyte count;
IRF, immature RET fraction;
Neut, neutrophils;

TABLE 5-continued

| | Vehicle control | Taxol 15 mg/kg | Cmpd A 20 mg/kg | Cmpd A 60 mg/kg | Cmpd B 6 mg/kg | Cmpd B 20 mg/kg | Cmpd C 20 mg/kg |
|---|---|---|---|---|---|---|---|

Lymph, lymphocytes;
Mono, monocytes;
Eos, eosinophil count;
Baso, basophils.
All treatment group means were determined from 10 animals, except controls (n = 8; 1 death and 1 lost sample).

In a separate study, non-xenografted CD-1 nude animals had adjusted resting HGB and HCT values of 13.9 g/dl and 42%, respectively, as compared to 12.1 g/dl and 35% observed in the vehicle-treated xenograft animal group in the study described here. Anemia is a common side affect of cancer, thus the consistent improvements in key markers of erythropoiesis as observed following treatment with compounds of the invention reflect correction of an anemic state induced by tumor xenografts, and indicate restoration of normal blood parameters. Thus, simultaneous improvements in key blood parameters related to anemia and suppression of tumor development can be obtained with compounds and methods of the present invention. Study endpoint tumors were fixed for H&E histological assessment. These fixed tumor samples are also examined for markers of tumor vascularity, tumor apoptosis, and tumor cell proliferation.

Example 2

Compounds and Methods of the Invention Limit Progression of Subcutaneously Implanted Human A549 Lung Tumors in a Mouse Xenograft Model Procedures were carried out as described above for Example 1, with the following changes. The human H-460 lung cancer cell line was replaced by the human A549 lung cancer cell line. Xenografted H460 tumors are characterized by a high growth rate, while xenografted A549 tumors progress substantially more slowly. A549 has been characterized extensively. (See, e.g., (Kraus-Berthier et al., (2000) Clin Cancer Res 6:297-304; Hanze et al., (2003) Biochem Biophys Res Commun 312:571-577; Wedge et al., (2002) Cancer Res 62:4645-4655; and Abdollahi et al., (2003) Cancer Res 63:8890-8898.) Compound B treatment groups (6 mg/kg, 20 mg/kg) were replaced by compound D treatment groups (6 mg/kg, 20 mg/kg). Other experimental parameters were identical to those described in Example 1 above.

Table 6 below shows the effect of various compounds of the present invention on A549 mean tumor volumes (mm$^3$, calipers) in a mouse xenograft model. As shown in Table 6, administration of compounds of the invention resulted in reduced mean tumor volumes vs. controls as determined 7 days (1 week) through 9 weeks following initiation of compound dosing. Within 1 week (7 days) from the start of this study, mean tumor volumes increased 45% in the vehicle control group. Increases in mean tumor volumes in the 20 mg/kg Compound D and Compound C groups were limited to 20% and 22%, respectively. Taxol, included as a positive control, also produced a statistically significant inhibition of tumor progression, reflected by a mean tumor volume increase of 23% in this same time interval. Reduced tumor volumes were observed in animals administered compounds of the present invention. These data indicated that administration of compounds of the present invention in a mouse xenograft tumor model resulted in inhibition or reduction of tumor growth and development. Theses results were consistent with results obtained with H-460 xenografted tumors, and indicated that inhibition of tumor progression and growth by compounds of the present invention occurred in independent xenografted lung tumor models having varying rates of tumor development.

TABLE 6

| Weeks treatment | Vehicle | Taxol 15 mg/kg | Cmpd A 20 mg/kg | Cmpd A 60 mg/kg | Cmpd D 6 mg/kg | Cmpd D 20 mg/kg | Cmpd C 20 mg/kg |
|---|---|---|---|---|---|---|---|
| 0 | 98 | 106 | 100 | 105 | 109 | 106 | 102 |
| 1 | 142 | 130 | 138 | 133 | 137 | 126 | 124 |
| 2 | 179 | 152 | 173 | 175 | 178 | 148 | 152 |
| 3 | 258 | 177 | 241 | 234 | 209 | 193 | 180 |
| 4 | 330 | 179 | 328 | 324 | 263 | 227 | 208 |
| 5 | 386 | 186 | 375 | 348 | 292 | 272 | 246 |
| 6 | 454 | 231 | 428 | 425 | 339 | 304 | 304 |
| 7 | 546 | 275 | 523 | 514 | 375 | 373 | 341 |
| 8 | 575 | 347 | 547 | 538 | 431 | 411 | 402 |
| 9 | 629 | 360 | 615 | 597 | 476 | 466 | 429 |

Values in the table represent means (n = 10).

Table 7 below shows methods and compounds of the present invention reduced tumor weights (grams) as determined at necropsy in subcutaneously implanted human A549 lung tumors in a mouse xenograft model. These results indicated that methods and compounds of the present invention are useful for inhibiting or reducing tumor growth and progression.

TABLE 7

| Group | Mean (g) | SD |
|---|---|---|
| Vehicle | 0.89 | 0.43 |
| Taxol 15 mg/kg | 0.45 | 0.29 |
| Cmpd A 20 mg/kg | 0.76 | 0.87 |
| Cmpd A 60 mg/kg | 0.81 | 0.7 |
| Cmpd D 6 mg/kg | 0.51 | 0.3 |

TABLE 7-continued

| Group | Mean (g) | SD |
|---|---|---|
| Cmpd D 20 mg/kg | 0.58 | 0.54 |
| Cmpd C 20 mg/kg | 0.50 | 0.4 |

These results indicated that methods and compounds of the present invention are useful for inhibiting or reducing tumor growth and progression.

Example 3

Compounds and Methods of the Invention Limit Progression of Orthotopically Implanted Human H-460-GFP Lung Tumors in a Mouse Xenograft Model To examine the effect of methods and compounds of the present invention in a metastatic model of tumor progression, compounds of the invention were administered to orthotopically implanted H-460-GFP xenografted animals. Tumor models employing surgical orthotopic implantation (SOI) into the organ of origin of the original tumor are regarded as representative of cancer progression and metastasis in humans. Orthotopic implantation of H-460 increases the rate of tumor metastasis.

This experiment is carried out as described in Example 1 above, with the following modifications. To aid in identification and scoring of metastasis, the human H-460 lung cancer cell line was replaced by genetically-engineered tumors of GFP-transfected H-460 cells. 1-2 mm$^3$ H460-GFP lung tumor fragments were implanted by surgical orthotopic implantation (SOI) and sutured directly into lung tissue. (Yang et al., (1998) Cancer Res 58:4217-4221.) Dosing was initiated immediately after successful confirmation of tumor take by fluorescent GFP imaging (~5 days following tumor implantation). Doxorubicin (DOX, 7.5 mg/kg, i.v. administration) was used as a chemotherapy control, and was administered on treatment days 3, 7, and 11.

In addition to weekly caliper measurement of primary tumor size, GFP imaging was performed on animals to monitor primary tumor progression and metastasis, starting the first day of treatment. Study endpoints were reached when an average tumor size of 2 cc or three morbid mice appear in any one group, whichever occurs first, regardless of treatment duration. Each animal was checked daily for mortality or signs of morbidity. Morbid animals were frozen. All animals, including dead animals, were examined by GFP imaging for primary tumor and metastasis at necropsy. Imaging and caliper measurements were used to determine the effects of treatment. Primary tumors were excised, measured and weighed at necropsy. Blood samples were taken during terminal sacrifice and complete blood counts (CBC) and reticulocyte analysis were performed.

Tumor metastasis is associated with increased morbidity and mortality in humans with metastatic cancer and in animal models of metastatic cancer. As expected, increased morbidity and mortality were observed in these animals prior to termination of the present study. The increased morbidity and mortality were recorded and animals were preserved for subsequent necropsy. The study was terminated after >3 animals were found morbid in the vehicle group on treatment day 14, at which point the remaining animals were sacrificed to evaluate and compare tumor progression in the various treatment groups.

Table 8 below shows the effect of compounds of the present invention on survival in H460-GFP xeongrafted animals in this study. As shown in Table 8, the frequency of deaths or morbidity in this study differed between treatment groups. In the vehicle control group, 50% of animals were determined to be morbid prior to study termination. In treated animals, 10-20% of animals were determined to be morbid prior to study termination. These results suggested that methods and compounds of the present invention are useful for treating cancer and for increasing survival of individuals having cancer.

TABLE 8

| Days Treatment | Vehicle | DOX | Cmpd A 20 mg/kg | Cmpd A 60 mg/kg | Cmpd E 20 mg/kg | Cmpd D 20 mg/kg | Cmpd C 20 mg/kg |
|---|---|---|---|---|---|---|---|
| 9 | 9/10 | 10/10 | 10/10 | 10/10 | 9/10 | 10/10 | 10/10 |
| 11 | 9/10 | 10/10 | 10/10 | 10/10 | 9/10 | 9/10 | 10/10 |
| 12 | 9/10 | 10/10 | 10/10 | 9/10 | 9/10 | 9/10 | 9/10 |
| 13 | 6/10 | 10/10 | 8/10 | 9/10 | 8/10 | 9/10 | 8/10 |
| 14 | 5/10 | 10/10 | 8/10 | 9/10 | 8/10 | 9/10 | 8/10 |

Values represent proportion of surviving animals.
Morbid animals were first identified after 9 days treatment To determine metastatic frequency, the thoracic and abdominal cavities of animals were examined by fluorescent imaging. Table 9 below shows the effect of administration of compounds of the present invention on the incidence of mediastinal lymph node metastasis in orthotopically H-460-GFP xenografted animals. As shown in Table 9, the incidence of mediastinal lymph node metastasis in animals administered compound of the present invention was reduced compared to that in vehicle control animals.

TABLE 9

| | Vehicle | DOX | Cmpd A 20 mg/kg | Cmpd A 60 mg/kg | Cmpd D 20 mg/kg | Cmpd C 20 mg/kg |
|---|---|---|---|---|---|---|
| Metastatic Incidence | 9/10 | 4/10[#] | 8/10 | 7/10 | 9/10 | 5/10 |

Values represent proportion of animals exhibiting mediastinal lymph node metastasis.
[#] = p < 0.1, Fisher's exact test.

Example 4

Compounds and Methods of the Invention Limit Progression of Orthotopically Implanted Human HCT116-GFP in a Mouse Xenograft Model Procedures were carried out as described above for Example 3, except that the tumors of GFP-transfected H-460 cells were replaced with HCT116-GFP colon tumors, and surgical orthotopic implantation was directly into colon tissue.

The HCT116 tumor model used here is a well-characterized representative colon xenograft model. The isolation of the human HCT116 tumor cell line from a human colon carcinoma has been described. (Brattain et al (1981) Cancer Res 41:1751-1756.) To aid in the detection of tumors and metastases, HCT116 cells were transduced with genes directing the expression of fluorescent proteins (e.g., HCT116-GFP). The use of fluorescent HCT116-derived tumors in similar studies has been described previously. (Ross et al (2000) Nat Genet 24:227-235.)

HCT116-GFP tumor fragments harvested from the stock animals were transplanted into animals by surgical orthotopic implantation (SOI) as follows. The animals were anesthetized with isoflurane and the surgical area was sterilized using iodine and alcohol. After proper exposure of the colon following a lower midline abdominal incision, the serosa of the colon was removed and two pieces of 1 mm³ tumor fragments per mouse were implanted. An 8-0 surgical suture was used to penetrate these small tumor pieces and suture them on the wall of the intestine. The intestine was then returned to the abdominal cavity. The incision in the abdominal wall was closed with a 6-0 surgical suture in one layer. The animals were kept under isoflurane anesthesia during surgery. All procedures of the operation described above were performed under a 7× magnification microscope (Olympus). Animals were kept in a barrier facility under HEPA filtration.

Administration of Compound A or 5-FU (5-Flurouracil) to the animals was initiated three days following tumor transplantation. 5-FU, a chemotherapeutic agent used as a positive control, was administered by intraperitoneal injection (60 mg/kg) at four day intervals for a total of three doses. Compound A was administered at either 20 mg/kg or 60 mg/kg three times per week. Tumor volumes were measured at day 15, day 22, and day 29.

As shown in Table 10, mean tumor volumes were reduced in animals administered Compound A. These results showed that methods and compounds of the present invention were effective at reducing tumor volume and inhibiting tumor progression in colon tumors.

TABLE 10

| Agent | Treatment Day 15 | Treatment Day 22 | Treatment Day 29 |
|---|---|---|---|
| CMC Vehicle | 44 +/− 36 | 86 +/− 58 | 227 +/− 173 |
| 5-FU | 0 +/− 0 | 1 +/− 4 | 8 +/− 13 |
| Compound A 20 mg/kg | 39 +/− 27 | 67 +/− 49 | 197 +/− 158 |
| Compound A 60 mg/kg | 24 +/− 23 | 45 +/− 38 | 152 +/− 125 |

(calipers, mean +/− SD, n = 8–10/group)

Example 5

Compounds and Methods of the Invention Limit Progression of Orthotopically Implanted Human MDA-MB-435-GFP Breast Tumors in a Mouse Xenograft Model The experiment was conducted essentially as described above in Example 3, except that the tumors of GFP-transfected H-460 cells were replaced with MDA-MB-435-GFP breast tumors, with surgical orthotopic implantation directly into breast tissue of female CD-1 nude animals. The number of animals in each group was increased to 15. MDA-MB-435 breast tumors have an overall gene expression profile reminiscent of that in malignant melanoma, suggesting that MDA-MB-435 breast tumors are melanoma-derived. (See, e.g., Ross et al (2000) Nat Genet 24:227-235 and Ellison et al. Mol Pathol. (2002) 55:294-299.)

In the present MDA-MB-435-GFP breast cancer orthotopic study, administration of compound A was initiated 21 days after tumor fragment implantation to the mammary fat pad of female nude mice, at time at which the volume of primary tumors reached ~150 mm³. Taxotere, a positive chemotherapeutic agent control, was administered i.v. once weekly (15 mg/kg). After mean tumor volume in the vehicle control group exceeded 1 cm³, animals were sacrificed (33 days of treatment) and primary tumors were excised from all animals and weighed.

As shown in FIG. 1, mean tumor volumes in animals administered Compound A were reduced by approximately 20% compared to mean tumor volumes in animals administered vehicle control. (Data in FIG. 1 is presented as mean tumor volumes +/−SEM; N=15/group.)

These results indicated that compounds and methods of the invention are useful to reduce tumor volume and inhibit progression of breast tumors. The MDA-MB435 breast cancer cell line shares properties with cell lines of malignant melanoma origin; therefore, these results further indicated that methods and compounds of the present invention are useful for reducing tumor volume and inhibiting tumor progression in tumors of melanoma origin.

Example 6

Compounds and Methods of the Invention Limit Progression of Subcutaneously Implanted Human H460 Lung Tumors in a Mouse Xenograft Model in Combination with Chemotherapeutics This study was used to determine the effect of combined treatments where compounds and methods of the invention were combined with conventional anti-tumor therapies. These experiments were performed essentially as described above in Example 3, except that 1×10⁷ H460 tumor cells were implanted subcutaneously to the flanks of female Harlan nude animals. The number of animals in each group was 10. Treatments were initiated when tumors reached an average size of approximately 100 mm³.

The study design was representative of tumor progression studies of the TGD (Tumor Growth Delay) type, using a protocol that required individual animals to be humanely euthanized after reaching a set endpoint of tumor volume greater than or equal to 2 cc.

Animals were administered Compound A (60 mg/kg) with or without additional administration of one of the chemotherapeutic agent paclitaxel or carboplatin. These two chemotherapeutic agents are of two broad classes of conventional anti-tumor therapeutics: microtubule poisons (paclitaxcel); and DNA-directed agents, including the sub-classification of DNA alkylating agents (carboplatin). In tumor-bearing human patients, conventional anti-tumor therapy commonly use of one or both classes of chemotherapeutic agents.

Combined treatment groups (i.e., treatment with both paclitaxel and Compound A or treatment with both carboplatin and Compound A) were administered compound of the present invention and chemotherapeutic agents on different days. The study was initiated with administration of conventional anti-tumor treatment or vehicle control, and followed one day after with administration of Compound A or vehicle control. Treatment was continued over a course of 62 days, until all animals reached a pre-defined endpoint of tumor volume greater than or equal to 2 cc, or died prematurely due to other causes. (See Table 11 and Table 12 for compound and chemotherapeutic agent dosing schedule.)

TABLE 11

1 Drug/Testing Agent

| Agent | mg/kg | Route | Schedule |
|---|---|---|---|
| 5% EC in D5W | — | i.v. | (q.o.d × 3) weekly start Day 1 |
| 5% EC in D5W | — | i.v. | (q.o.d × 3) weekly start Day 1 |
| paclitaxel | 15 | i.v. | (q.o.d × 3) weekly start Day 1 |
| carboplatin | 120 | i.p. | Q7 d to end start Day 1 |
| paclitaxel | 15 | i.v. | (q.o.d × 3) weekly start Day 1 |
| carboplatin | 120 | i.p. | Q7 d to end start Day 1 |

TABLE 12

2 Drug/Testing Agent

| Agent | mg/kg | Route | Schedule |
|---|---|---|---|
| vehicle | — | p.o. | (q.o.d × 3) weekly start Day 2 |
| Cmpd A | 60 | p.o. | (q.o.d × 3) weekly start Day 2 |
| vehicle | — | p.o. | (q.o.d × 3) weekly start Day 2 |
| vehicle | — | p.o. | (q.o.d × 3) weekly start Day 2 |
| Cmpd A | 60 | p.o. | (q.o.d × 3) weekly start Day 2 |
| Cmpd A | 60 | p.o. | (q.o.d × 3) weekly start Day 2 |

5% EC in D5W (5% Ethanol, 5% Cremophor EL, 90% D5W
D5W (Dextrose 5% in water (i.v. vehicle))
QOD (Quaque Other Die, every other day)
Q7D (every seventh day)

Tumor progression was determined for each treatment group and is presented as median Time-to-Endpoint (TTE). The results are shown below in Table 13.

TABLE 13

| Group | Median TTE | T-C | % TGD | % TGD (2) |
|---|---|---|---|---|
| i.v. vehicle and p.o. vehicle | 16.2 | — | — | — |
| i.v. vehicle and Cmpd. A | 17.7 | 1.5 | 9% | — |
| paclitaxel and p.o. vehicle | 33.1 | 16.9 | 104% | — |
| carboplatin and p.o. vehicle | 33.5 | 17.3 | 107% | — |
| paclitaxel and Cmpd A | 34.6 | 18.4 | 114% | 5% |
| carboplatin and Cmpd A | 34.1 | 17.9 | 110% | 2% |

Abbreviations:
TTE, Time-to-Endpoint (days), group median;
T-C, Test-control (days), difference of medians;
% TGD, Percent Tumor Growth Delay (vs. Group control);
% TGD (2), Percent Tumor Growth Delay (vs. respective conventional chemotherapeutic controls).

As shown in Table 13, tumor progression was inhibited by Compound A, resulting in a 9% delay in time to endpoint (greater or equal to 2 cc tumor volume) as compared to the vehicle treated control group. Carboplatin and paclitaxel treatment also resulted in inhibition of tumor progression. When these conventional chemotherapeutics were combined with Compound A treatment, a further inhibition of tumor progression was apparent. (See Table 13, % TGD of 5% and 2% for paclitaxel and Cmpd A and carboplatin and Cmpd A, respectively). These results showed that methods and compounds of the present invention are effective at inhibiting or reducing tumor progression. Additionally, these results provided evidence that compounds of the present invention, when administered in combination with current chemotherapeutics, provides additional benefit for inhibiting tumor growth compared to administration of a chemotherapeutic alone.

Example 7

Compounds and Methods of the Invention Limit the Progression of OVCAR3 Ovarian Tumors The experiment was conducted essentially as described above in Example 3, except that the tumors of GFP-transfected H460 cells were replaced with OVCAR3 ovarian tumors. OVCAR3 tumor fragments (1 mm$^3$) were implanted subcutaneously into the flanks of female CB. 17 SCID mice. The number of animals in each treatment group was 10. Treatment was initiated when tumors reached an approximate average size of 100 mm$^3$. Paclitaxel, a positive chemotherapeutic control, was administered i.v. every other day (20 mg/kg) for a total of 5 doses.

Figure 2:
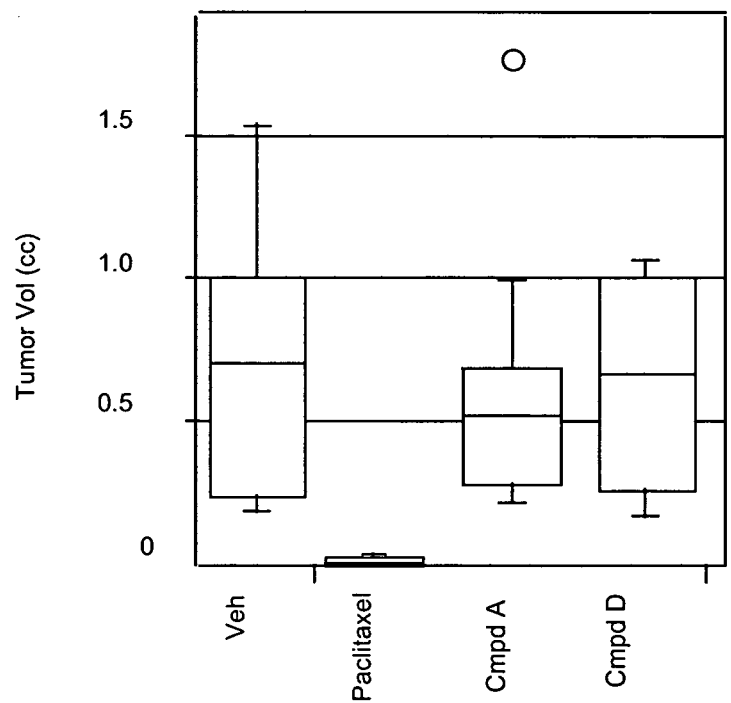
FIG. 2 sets forth data showing compounds and methods of the present invention reduced tumor volume in an animal xenograft model of subcutaneously-implanted ovarian tumors.

As shown in FIG. 2, administration of Compound A (60 mg/kg) or Compound D (60 mg/kg) resulted in decreased tumor volumes at study end (day 29). Specifically, median tumor volumes were reduced by 26% and 5% (compared to that in vehicle-treated control animals) in animals administered Compound A and Compound D, respectively. FIG. 2 is a Kruskal-Wallis box plot. The central bar within each box indicates the median value for the group, the limits of the various boxes and whiskers indicate group quartiles within the total distribution of values determined in this study.

The results indicated that compounds and methods of the present invention are useful for reducing tumor volume and inhibiting tumor progression of ovarian tumors.

Example 8

In vitro Screening and Identification of Compounds Useful For Treating Cancer

To identify compounds useful in the methods of the present invention, the following studies were performed. The effect of compounds of the present invention on expression of various genes associated with anti-tumor activity (e.g., genes having anti-proliferative activity, genes having pro-apoptotic activity, genes having anti-tumor activity, etc.). In these experiments, the effect of compounds on BNIP3, BNIP3L, NDRG1, CDKN1C, and REDD1/RTP801 gene expression in various types of cultured tumor cells line was examined, including Hep3B cells (human hepatocellular carcinoma), Kelly neuroblastoma cells, and MCF7 cells (human breast cancer)

Hep3B Human Hepatocellular Carcinoma Cells

The effects of various compounds of the present invention on the expression of genes associated with tumor growth and progression were examined in Hep3B cells as follows. Hep3B cells (ATCC) were cultured in DMEM containing 8% fetal bovine serum (FBS) and antibiotics. For each experiment, Hep3 cells were added to 6-well tissue culture dishes (approximately 500,000 cells per well). After 8 hours, the media was replaced with DMEM containing 0.5% FBS. Sixteen hours later, various compounds of the present invention were added to the cultured cells to a final concentration of 25 µM. The cells were then harvested and added to RNA extraction buffer (RNeasy, Qiagen). RNA was isolated from cell lysates using RNeasy Mini spin columns (Qiagen) according to the manufacturer's instructions. Changes in expression of various gene transcript levels associated with tumor growth and progression were determined by Affymetrix microarray. Labeled probes were prepared and hybridized to U133A Affymetrix microarrays.

Changes in gene expression levels in vitro following compound addition are presented as fold change relative to gene expression levels observed in control cells treated with DMSO only. Data represents the average of two independent studies.

Kelly Neuroblastoma Cells

The effects of various compounds of the present invention on the expression of genes associated with tumor growth and progression were examined in Kelly neuroblastoma cells as follows. Kelly neuroblastoma cells were grown in RPMI media. For each experiment, Kelly neuroblastoma cells were added to 96-well tissue culture plates (approximately 40,000 cells per well) such that the plated cells reached confluence the following day. On the following day, the cells were washed and the media replaced with RPMI containing 0.5% FBS. Various compounds of the present invention were added to the cultured cells to a final concentration of 20 µM, and the cells cultured for an additional 20-24 hours. DMSO (0.5%) was added to control cell cultures.

RNA was isolated from the Kelly neuroblastoma cells using a commercial kit and used for the preparation of cDNA. BNIP3, CDKN1C, and 18S RNA levels were measured using commercial kits (18S, Applied Biosystems cat#4319413E); BNIP3, Applied Biosystems cat#HS00969293 MH). RNA levels for BNIP3 and CDKN1C were normalized to that of 18S RNA and is presented as fold-change compared to that observed in DMSO control cultures. Kelly cell NDRG1 and BNIP3L mRNA levels were measured by Affymetrix microarray in a separate study. Cells were harvested after 6 hours incubation with 20 µM test compound or DMSO (0.5%) as control. RNA was isolated and labeled probes were prepared and hybridized to U133 Plus 2.0 Affymetrix microarrays. Changes in gene expression levels are presented as fold change compared to that of control (0.5% DMSO-treated) cultures.

MCF7 Human Breast Cancer Cells

The effects of various compounds of the present invention on the expression of genes associated with tumor growth and progression were examined in MCF7 breast cancer cells as follows. In some experiments, MCF7 (ATCC) cells were plated in 96-well tissue culture dishes (approximately 20,000 cells per well) and cultured in DMEM media supplemented with 10% serum. The following day, the cells were washed and the media was replaced with DMEM containing 0.5% FBS. Various compounds of the present invention were added to the cultured cells to a final concentration of 20 µM, and the cells cultured for an additional 20-24 hours. DMSO (0.5%) was added to control cell cultures. RNA was isolated as described above. Changes in gene expression levels are presented as fold change compared to that of control (0.5% DMSO-treated) cultures.

In other experiments, MCF7 cells were plated in 96-well tissue culture dishes as described above. After 24 hours, the cells were washed and the media was replaced with DMEM containing 0.5% FBS. Various compounds of the present invention were added to the cultured cells to a final concentration of 20 µM. DMSO (0.5%) was added to control cell cultures. After 24 hours, changes in gene expression of BNIP3 and 18S RNA were determined directly using one-step quantitative multiplex RT-PCR reactions according to the manufacturer's instructions (QuantiTect Multiplex RT-PCR Kit, Qiagen, catalog no. 204643). Changes in gene expression levels are presented as fold change compared to that of control (0.5% DMSO-treated) cultures.

The effect of compounds of the present invention on expression of various genes associated with anti-tumor activity in various cell types is shown below in Tables 14, 15, 16, 17, and 18.

As shown below in Table 14, compounds of the present invention were effective at increasing BNEP3 gene expression in Hep3B, MCF7, and Kelly cells. (Data in Table 14 is presented as fold-increase in BNIP3 mRNA expression measured in cells treated with compound relative to that in non-treated control cells.) Increased BNIP3 gene expression is associated with pro-apoptotic activity. These results suggested that compounds and methods of the present invention are useful for affecting tumor growth and progression and, thus, for treating cancer. Additionally, these results provide a method to identify compounds useful for the methods of the present invention.

TABLE 14

| Cell | F | G | A | H | I | J | N | K | C | E | B | L | D | M |
|---|---|---|---|---|---|---|---|---|---|---|---|---|---|---|
| Hep3B | 3.5 | 4.2 | 2.1 | 2.0 | 2.1 | ND | 3.6 | 3.0 | ND | ND | ND | ND | ND | ND |
| MCF7 | ND | ND | 3.9 | 3.2 | ND | 3.3 | 4.9 | 7.7 | 5.0 | 5.3 | 4.5 | 4.8 | ND | 0.4 |
| Kelly | ND | ND | 9.5 | 5.9 | ND | 8.9 | 27.1 | ND | 2.6 | 31.8 | 17.2 | 32.8 | 21.9 | 27.6 |

ND (not determined)

As shown below in Table 15, compounds of the present invention were effective at increasing BNIP3L gene expression in Hep3B and Kelly cells. (Data in Table 15 is presented as fold-increase in BNIP3L mRNA expression measured in cells treated with compound relative to that in non-treated control cells.) Increased BNIP3L gene expression is associated with pro-apoptotic activity. These results suggested that compounds and methods of the present invention are useful for affecting tumor growth and progression and, thus, for treating cancer. Additionally, these results provide a method to identify compounds useful for the methods of the present invention.

TABLE 15

| Cell | F | G | A | H | I | J | N | K | C | E | B | L | D | M |
|---|---|---|---|---|---|---|---|---|---|---|---|---|---|---|
| Hep3B | 3.2 | 4.3 | 1.8 | 1.5 | 1.7 | ND | 2.8 | 2.2 | ND | ND | ND | ND | ND | ND |
| Kelly | ND | ND | ND | ND | ND | ND | ND | ND | 5.9 | ND | ND | ND | ND | ND |

ND (not determined)

As shown below in Table 16, compounds of the present invention were effective at increasing CDKN1C gene expression in MCF7 and Kelly cells. (Data in Table 16 is presented as fold-increase in CDKN1C mRNA expression measured in cells treated with compound relative to that in non-treated control cells.) Increased CDKN1C gene expression is associated inhibition of the cell-cycle inhibitor, and decreased expression of CDKN1C is associated with cell cycle progression. These results suggested that compounds and methods of the present invention are useful for affecting tumor growth and progression and, thus, for treating cancer.

Additionally, these results provide a method to identify compounds useful for the methods of the present invention.

TABLE 16

| Cell | F | G | A | H | I | J | N | K | C | E | B | L | D | M |
|------|----|----|------|------|----|-----|-------|----|------|-------|------|-------|-------|-----|
| MCF7 | ND | ND | 0.7 | 0.7 | ND | 0.8 | 0.4 | ND | 0.6 | 0.4 | 0.5 | 0.2 | ND | 2.1 |
| Kelly | ND | ND | 71.8 | 11.6 | ND | 6.9 | 182.8 | ND | 49.0 | 184.2 | 91.0 | 120.2 | 382.2 | 3.4 |

ND (not determined)

As shown below in Table 117, compounds of the present invention were effective at increasing NDRG1 gene expression in Hep3B and Kelly cells. (Data in Table 17 is presented as fold-increase in NDRG1 mRNA expression measured in cells treated with compound relative to that in non-treated control cells.) Increased NDRG1 gene expression is associated with reduced tumor progression and invasiveness. These results suggested that compounds and methods of the present invention are useful for affecting tumor growth and progression and, thus, for treating cancer. Additionally, these results provide a method to identify compounds useful for the methods of the present invention.

TABLE 17

| Cell | F | G | A | H | I | J | N | K | C | E | B | L | D | M |
|------|-----|-----|-----|-----|-----|----|-----|-----|-----|----|----|----|----|----|
| Hep3B | 5.4 | 6.8 | 3.3 | 2.4 | 3.3 | ND | 3.7 | 3.3 | ND | ND | ND | ND | ND | ND |
| Kelly | ND | ND | ND | ND | ND | ND | ND | ND | 7.3 | ND | ND | ND | ND | ND |

ND (not determined)

As shown below in Table 18, compounds of the present invention were effective at increasing REDD1/RTP801 gene expression in Hep3B and Kelly cells. (Data in Table 18 is presented as fold-increase in REDD1/RTP801 mRNA expression measured in cells treated with compound relative to that in non-treated control cells.) Increased REDD1/RTP801 gene expression is associated with anti-proliferative and pro-apoptotic effects. These results suggested that compounds and methods of the present invention are useful for affecting tumor growth and progression and, thus, for treating cancer. Additionally, these results provide a method to identify compounds useful for the methods of the present invention.

Example 9

In Vivo Screening and Identification of Compounds Useful For Treating Cancer

The effects of various compounds of the present invention on the expression of genes associated with tumor growth and progression (e.g., expression of genes associated with anti-proliferative effects) were examined in vivo as follows. In these studies, male Swiss Webster mice (25 g) were administered a single intravenous (i.v.) dose of various compounds (60 mg/kg) of the present invention via the tail vein. Four hours after administration of compound, the kidneys and liver were removed and preserved in RNAlater (Ambion). RNA isolation and cDNA synthesis was carried out as follows. Murine kidney tissue was added to TRIzol (Invitrogen) and homogenized using a 5-mm stainless steel bead for 4 minutes at 25 Hz in a Mixer Mill 300 (Qiagen). Homogenates were extracted with chloroform according to the manufacturer's instructions and aqueous supernatants were isolated. The aqueous supernatants were combined with equal volumes of 70% ethanol and then loaded onto RNeasy Mini spin columns (Qiagen). RNA was isolated according to the manufacturer's instructions.

Synthesis of cDNA from the isolated total RNA was carried out using Omniscript reverse transcriptase (Qiagen) and random primers according to the manufacturer's instructions. Measurement of gene expression levels in compound-treated animals and in vehicle-treated control animals was performed by quantitative PCR using TaqMan Universal PCR Master

TABLE 18

| Cell | F | G | A | H | I | J | N | K | C | E | B | L | D | M |
|------|-----|------|-----|-----|-----|----|-----|-----|-----|----|----|----|----|----|
| Hep3B | 6.3 | 14.1 | 3.1 | 2.4 | 3.8 | ND | 5.7 | 4.8 | ND | ND | ND | ND | ND | ND |
| Kelly | ND | ND | ND | ND | ND | ND | ND | ND | 3.6 | ND | ND | ND | ND | ND |

ND (not determined)

Mix (Applied Biosystems) and TaqMan Assay-on-Demand assays (Applied Biosystems) in a Prism 7000 system instrument (Applied Biosystems), according to manufacturer's instructions. The assays used were as follows: 18S ribosomal RNA, Hs99999901_s1; BNIP3, Mm00833810_g1; BNIP3L, Mm00786306_s1; NDRG1, Mm00440447_m1. Each PCR amplification reaction included a standard curve and a water blank. Data for gene expression levels for BNIP3, BNIP3L, and NDRG1 were normalized to that of 18S ribosomal RNA within each sample. Data is presented as fold change in specific mRNA levels relative to that of non-treated control animals.

As shown in Table 19 and Table 20 below, administration of compounds of the present invention increased expression of genes associated with pro-apoptotic activity and reduced tumor progression and invasiveness in kidney (Table 19) and liver (Table 20).

TABLE 19

| Gene | Cmpd A (n = 12) | Cmpd J (n = 6) | Cmpd N (n = 3) | Cmpd C (n = 3) | Cmpd E (n = 3) | Cmpd B (n = 3) | Cmpd L (n = 3) | Cmpd D (n = 3) | Vehicle (n = 20) |
|---|---|---|---|---|---|---|---|---|---|
| BNIP3 | 2.9 +/− 0.3 | 2.0 +/− 0.2 | 3.1 +/− 0.4 | 1.5 +/− 0.4 | 2.1 +/− 0.4 | 2.1 +/− 0.2 | 2.8 +/− 0.3 | 5.8 +/− 2.9 | 1.0 +/− 0.1 |
| BNIP3L | 2.2 +/− 0.3 | 1.3 +/− 0.1 | 3.4 +/− 0.8 | 0.9 +/− 0.3 | 0.8 +/− 0.2 | 1.2 +/− 0.2 | 3.4 +/− 0.3 | 5.0 +/− 3.5 | 1.0 +/− 0.2 |
| NDRG1 | 1.9 +/− 0.2 | 1.7 +/− 0.3 | 1.2 +/− 0.2 | 1.0 +/− 0.4 | 1.8 +/− 0.2 | 0.9 +/− 0.1 | 1.0 +/− 0.1 | 3.6 +/− 2.5 | 1.0 +/− 0.1 |

TABLE 20

| Gene | Cmpd F | Cmpd A | Cmpd C | Cmpd E | Cmpd D |
|---|---|---|---|---|---|
| BNIP3 | 1.1 | 2.4 | 3.5 | 1.8 | 1.5 |
| BNIP3L | 1.3 | 1.6 | 2.6 | 1.7 | 1.2 |

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for treating cancer in a subject in need, the method comprising the steps of: (a) identifying a subject having cancer; (b) administering to the subject an effective amount of an agent that stabilizes HIFα, wherein the agent is a 2-oxoglutarate mimetic that inhibits HIF prolyl hydroxylase activity, thereby treating cancer in the subject; and (c) monitoring the progression of cancer in the treated subject.

2. The method of claim 1, wherein the subject is a mammalian subject.

3. The method of claim 1, wherein the subject is a human subject.

4. A method for inducing an anti-tumor effect in a subject having a tumor, the method comprising the steps of: (a) administering to the subject an effective amount of an agent that stabilizes HIFα, wherein the agent is a 2-oxoglutarate mimetic that inhibits HIF prolyl hydroxylase activity, thereby inducing an anti-tumor effect in the subject; and (b) measuring the anti-tumor effect in the subject.

5. The method of claim 1, wherein the administering to the subject an effective amount of the agent comprises administering the agent orally, systemically, intravenously, or by injection.

6. The method of claim 1, wherein the method further comprises administering to the subject one or more chemotherapeutic agent.

7. The method of claim 4, wherein the subject is a mammalian subject.

8. The method of claim 4, wherein the subject is a human subject.

9. The method of claim 4, wherein the administering to the subject an effective amount of the agent comprises administering the agent orally, systemically, intravenously, or by injection.

10. The method of claim 4, wherein the method further comprises administering to the subject one or more chemotherapeutic agent.

11. The method of claim 4, wherein the anti-tumor effect is selected from the group consisting of reducing tumor volume, inhibiting tumor growth, inhibiting tumor progression, altering metabolic activity in a tumor, inducing quiescence in a tumor, inhibiting or reducing tumor invasiveness, inhibiting or reducing tumor angiogenesis or tumor neovascularization, and reducing tumor weight.

12. A method for treating cancer in a subject in need, the method comprising the steps of: (a) identifying a subject having cancer; (b) administering to the subject an effective amount of an agent that inhibits HIF prolyl hydroxylase activity, and wherein the agent is a 2-oxoglutarate mimetic, thereby treating cancer in the subject; and (c) monitoring the progression of cancer in the treated subject.

* * * * *